(12) United States Patent
Musallam

(10) Patent No.: US 12,059,385 B2
(45) Date of Patent: Aug. 13, 2024

(54) NEUROMODULATION FOR TREATMENT OF RETINAL, CHOROIDAL AND OPTIC NERVE DISORDERS AND/OR DYSREGULATED REDUCED OCULAR BLOOD FLOW (OBF)

(71) Applicant: Ismail Mohammed Yousif Musallam, Jerusalem (IL)

(72) Inventor: Ismail Mohammed Yousif Musallam, Jerusalem (IL)

( * ) Notice: Subject to any disclaimer, the term of this patent is extended or adjusted under 35 U.S.C. 154(b) by 564 days.

(21) Appl. No.: 16/932,772

(22) Filed: Jul. 19, 2020

(65) Prior Publication Data

US 2021/0022948 A1 Jan. 28, 2021

Related U.S. Application Data

(60) Provisional application No. 62/876,795, filed on Jul. 22, 2019.

(51) Int. Cl.
*A61H 5/00* (2006.01)
*A61H 21/00* (2006.01)
(Continued)

(52) U.S. Cl.
CPC .............. *A61H 5/00* (2013.01); *A61H 21/00* (2013.01); *A61H 23/006* (2013.01); *A61K 9/0048* (2013.01); *A61K 31/375* (2013.01); *A61K 35/16* (2013.01); *A61K 35/19* (2013.01); *A61K 38/17* (2013.01); *A61N 1/0456* (2013.01); *A61N 1/36014* (2013.01); *A61N 1/36034* (2017.08); *A61N 1/36046* (2013.01); *A61N 1/36053* (2013.01); *A61N 5/062* (2013.01); *A61N 5/0622* (2013.01); *A61N 7/00* (2013.01); *A61P 27/02* (2018.01); *A61H 2201/105* (2013.01); *A61N 1/0546* (2013.01); *A61N 2005/0663* (2013.01); *A61N 2007/0026* (2013.01); *A61N 2007/0043* (2013.01)

(58) Field of Classification Search
CPC ........ A61H 5/00; A61H 21/00; A61H 23/006; A61H 23/0245; A61H 23/0263; A61H 2201/0153; A61H 2201/0157; A61H 2201/10; A61H 2201/105; A61H 2201/1635; A61H 2201/1685; A61H 2201/1688; A61H 2201/5025; A61H 2201/5046; A61H 2205/024; A61K 35/16; A61K 35/19; A61K 38/2271; A61K 31/375; G01N 33/48; G01N 33/5002
USPC ......................................... 514/5.2, 802, 803
See application file for complete search history.

(56) References Cited

U.S. PATENT DOCUMENTS 5,099,829 A * 3/1992 Wu .......................... A61N 1/32
606/204.15
7,146,209 B2 * 12/2006 Gross ................. A61N 1/36046
607/2

(Continued)

*Primary Examiner* — Colin W Stuart
*Assistant Examiner* — Matthew D Ziegler

(57) ABSTRACT

A method and/or device for treatment of dysregulated reduced blood (e.g., reduced ocular blood flow) and, more particularly, but not exclusively, to methods and/or devices for treatment retinal, choroidal and optic nerve disorders. The treatment includes application of an effective amount of ONS ophthalmic nerve stimulation alone and/or in combination with peri-ocular administration of substance Neuropeptides/Platelet Rich Plasma (N/PRP) and/or ascorbic acid as a sympatholytic agent.

24 Claims, 17 Drawing Sheets

(51) Int. Cl.
*A61H 23/00* (2006.01)
*A61K 9/00* (2006.01)
*A61K 31/375* (2006.01)
*A61K 35/16* (2015.01)
*A61K 35/19* (2015.01)
*A61K 38/17* (2006.01)
*A61N 1/04* (2006.01)
*A61N 1/05* (2006.01)
*A61N 1/36* (2006.01)
*A61N 5/06* (2006.01)
*A61N 7/00* (2006.01)
*A61P 27/02* (2006.01)

(56) References Cited

U.S. PATENT DOCUMENTS

| | | | |
|---|---|---|---|
| 8,523,791 B2* | 9/2013 | Castel | A61F 7/00 |
| | | | 601/46 |
| 9,440,065 B2* | 9/2016 | Ackermann | A61N 1/0546 |
| 9,895,279 B2* | 2/2018 | Juto | A61H 23/02 |
| 2009/0005713 A1* | 1/2009 | Podrazhansky | A61H 23/0236 |
| | | | 601/2 |
| 2015/0087583 A1* | 3/2015 | Radhakrishnan | A61K 38/12 |
| | | | 604/257 |

* cited by examiner

FIG 10.A

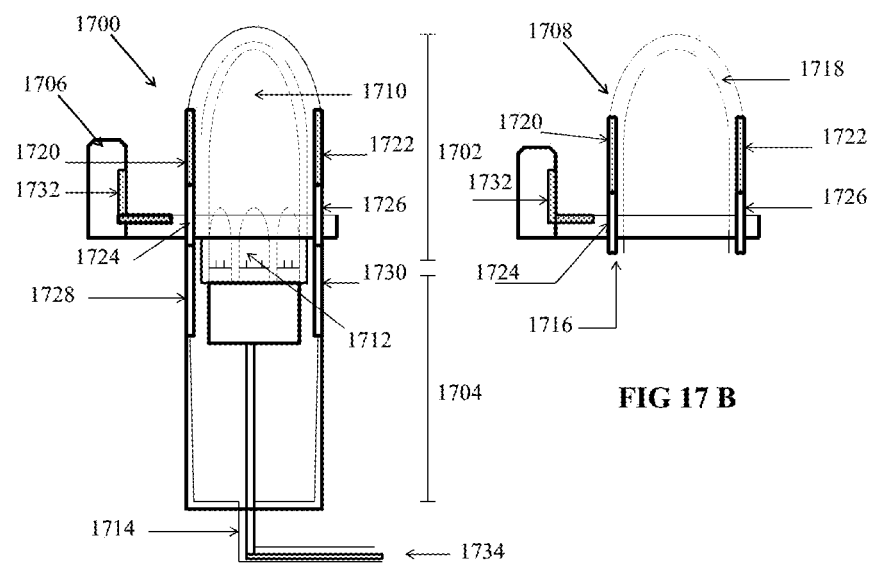
FIG. 17 A
FIG 17 B
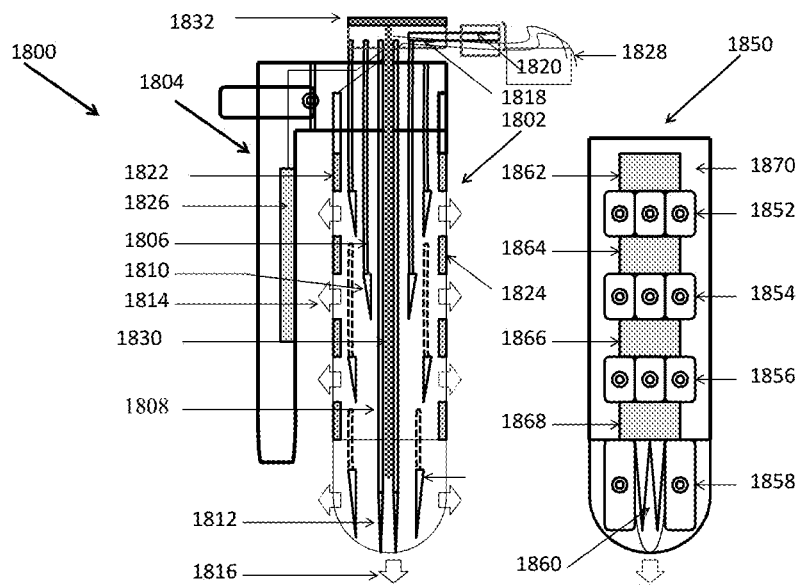
FIG. 18 A
FIG. 18 B

NEUROMODULATION FOR TREATMENT OF RETINAL, CHOROIDAL AND OPTIC NERVE DISORDERS AND/OR DYSREGULATED REDUCED OCULAR BLOOD FLOW (OBF)

FIELD AND/OR BACKGROUND OF THE INVENTION

The present invention, in some embodiments thereof, relates to a method and/or device for treatment of dysregulated reduced ocular blood flow and, more particularly, but not exclusively, to a method and/or device for treatment of retinal, choroidal and optic nerve disorders via application of an effective amount of ophthalmic nerve stimulation alone and/or in combination with sympatholytic agents and/or peri-ocular administration of Neuropeptides/Platelet Rich Plasma derived from external jugular vein after sufficient ophthalmic nerve stimulation. The inventive method described here can be used along with other known therapeutic agents for treatment of clinically developed retinal, choroidal and optic nerve disorders. The inventive method described here can also be used as a preventive treatment for preclinical stage of the disease.

BACKGROUND OF THE INVENTION

Retinal, choroidal and optic nerve disorders are multifactorial and mostly progressive diseases with extremely complex pathogenesis. Age related macular degeneration (AMD), Diabetic retinopathy (DR), retinitis pigmentosa (RP), congenital achromatopsia, central serous chorioretinopathy (CSCR), central retinal vein occlusion (CRVO), and central retinal artery occlusion (CRAO), glaucomatous optic neuropathy, ischemic, inflammatory and traumatic optic neuropathy are leading causes of vision loss worldwide. Currently there is no treatment for RP, congenital achromatopsia geographic dry type of AMD, CRAO, and ischemic, traumatic and glaucomatous optic neuropathy. The treatment of neovascular age-related macular degeneration (AMD) and complications associated with DR and CRVO involve frequent anti-vascular endothelial growth factor (VEGF) intravitreal injections, laser photocoagulation and vitrectomy. Though effective in treating the complications associated with these diseases, they do little to reverse the course of the disease. Additionally, there is no effective preventive treatment for these blinding ocular disorders.

Over the last few years, there has been mounting evidence in the literature on the possible role played by reduced dysregulated OBF both in retina-choroidal and in retroocular vascular system in pathogenesis of the majority of retinal, choroidal and optic nerve diseases such as IRDs, AMD, DR, ischemic optic neuropathy and retinal vascular occlusive diseases. Improving or preserving OBF may assist photoreceptors PRs and retinal ganglion cells RGCs by maintaining the necessary oxygenation and nutrients for cellular survival and preventing secondary degeneration by increasing the clearance of toxic by-products. In turn, various pharmaceutical agents has been tried to more precisely address the pathophysiology underlying specific ocular disorders, more particularly, those ocular disorders whose progression may be attenuated, ameliorated, or reversed by improving ocular circulation. Unfortunately, theses therapeutic agents exhibit a limited success and numerous systemic side effects.

Trigeminovascular system TVS has provided a great opportunity to modulate choroidal, retinal and ONH circulation and to provide an innovative treatment for a number of ischemic diseases of these ocular tissues. The neuropeptides such as SP and calcitonin gen reacting protein (CGRP) are released from ophthalmic nerve (V1) endings have a robust vasodilatory effect. Manipulations of TVS and parasympathetic tone via V1 stimulation have been shown to improve OBF. The question arises whether manipulation of the innervations of the ophthalmic artery and its branches can influence OBF in a way comparable to improvement of choroidal and retinal and ONH blood flow. If these manipulations can indeed influence OBF, then this suggests that these manipulations might form the basis of a therapeutic intervention in patients who suffer retinal, choroidal or optic nerve ischemia and/or dysregulated OBF as a result of genetic or acquired vascular disorder.

Background art includes

Aït-Ali N, Fridlich R, Millet-Puel G et al. (2015) Rod-derived cone viability factor promotes cone survival by stimulating aerobic glycolysis, May 7; 161(4):817-32.

Andersson S E. (1987) Responses to Antidromic Trigeminal Nerve Stimulation, Substance P, Nka, Cgrp and Capsaicin in the Rat Eye. Acta physiologica Scandinavia, 131:371-376.

Beutelspacher S C, Serbecic N, Barash H. et al (2011) "Retinal blood flow velocity measured by retinal function imaging in retinitis pigmentosa," Graefe's Archive for Clinical and Experimental Ophthalmology, vol. 249, no. 12, pp. 1855-1858.

Bill A and G. Sperber O, "Control of retinal and choroidal blood flow," Eye, vol. 4, no. 2, pp. 319-325, 1990.

Byrne, L. C., Dalkara, D., Luna, G., Fisher, S. K., Cle'rin, E., Sahel, J. A., Le'veillard, T., and Flannery, J. G. (2015). Viral-mediated RdCVF and RdCVFL expression protects cone and rod photoreceptors in retinal degeneration. J. Clin. Invest. 125, 105-116

Cellini M, Strobbe E, Gizzi C, and Campos E C. (2010) "ET-1 plasma levels and ocular blood flow in retinitis pigmentosa," Canadian Journal of Physiology and Pharmacology, vol. 88, no. 6, pp. 630-635.

Delaey C and Van De Voorde J. (2000) "Regulatory mechanisms in the retinal and choroidal circulation," Ophthalmic Research, vol. 32, no. 6, pp. 249-256.

Falsini B., Anselmi G M, Marangoni D. et al. (2011) "Subfoveal choroidal blood flow and central retinal function in retinitis pigmentosa," Investigative Ophthalmology & Visual Science, vol. 52, no. 2, pp. 1064-1069.

Flammer J, Konieczka K, and Flammer A J. (2013) "The primary vascular dysregulation syndrome: implications for eye diseases," EPMA Journal, vol. 4, no. 1, article 14.

Goadsby P J, Hoskin K L. (1997) The distribution of trigeminovascular afferents in the nonhuman primate brain Macaca nemestrina: a c-fos immunocytochemical study. J Anat. April; 190 (Pt 3):367-75.

Goadsby P J, Edvinsson L, Ekman R. (1988) Release of vasoactive peptides in the extracerebral circulation of humans and the cat during activation of the trigeminovascular system. Ann Neurol. February; 23(2):193-6.

Goadsby P J, Lambert G A, Lance J W. (1986) Stimulation of the trigeminal ganglion increases flow in the extracerebral but not the cerebral circulation of the monkey. Brain Res., 381(1):63-7.

Grunwald J E, Maguire A M., and Dupont J. (1996) "Retinal hemodynamics in retinitis pigmentosa," American Journal of Ophthalmology, vol. 122, no. 4, pp. 502-508.

Guadagni V, Novelli E, and Strettoi E. (2015) "Environmental enrichment reduces photoreceptor degeneration and retinal inflammation in a mouse model of retinitis pigmentosa," Investigative Ophthalmology & Visual Science, vol. 56, no. 7, pp. 4261-4261.

Hayreh S S, "Segmental nature of the choroidal vasculature," British Journal of Ophthalmology, vol. 59, no. 11, pp. 631-648, 1975.

Hiraba H, Inoue M, Gora K, Sato T, Nishimura S, Yamaoka M, Kumakura A, Ono S, Wakasa H, Nakayama E, Abe K, Ueda K. (2014) Facial vibrotactile stimulation activates the parasympathetic nervous system: study of salivary secretion, heart rate, pupillary reflex, and functional near-infrared spectroscopy activity. Biomed Res Int, 910812.

Jean A (1991). The nucleus tractus solitarius: neuroanatomic, neurochemical and functional aspects]. Arch Int Physiol Biochim Biophys. September; 99(5):A3-52. Review. French.

Kaplan H J, Wang W, Dean D C. Restoration of Cone Photoreceptor Function in Retinitis Pigmentosa. Transl Vis Sci Technol. 2017 Sep. 6; 6(5):5.

Lambert G A, Bogduk N, Goadsby P J, Duckworth J W, Lance J W. (1984) Decreased carotid arterial resistance in cats in response to trigeminal stimulation. J Neurosurg, 61(2):307-15.

Langham M E and Kramer T. (1990), "Decreased choroidal blood flow associated with retinitis pigmentosa," Eye, vol. 4, no. 2, pp. 374-381.

Lonescu E, Rohner-Jeanrenaud F, Berthoud H R, Jeanrenaud B. (1983) Increases in plasma insulin levels in response to electrical stimulation of the dorsal motor nucleus of the vagus nerve. Endocrinology, 112(3):904-10.

Matynia A, Nguyen E, Sun X, Blixt F W, Parikh S, Kessler J, Pérez de Sevilla Müller L, Habib S, Kim P, Wang Z Z, Rodriguez A, Charles A, Nusinowitz S, Edvinsson L, Barnes S, Brecha N C, Gorin M B. (2016) Peripheral Sensory Neurons Expressing Melanopsin Respond to Light. Front Neural Circuits, 10:60.

McDougal D H. and Gamlin P D. Autonomic control of the eye. (2018) The Journal of Headache and Pain. 19:22

Murakami Y, Ikeda Y, Akiyama M et al. (2016) "Correlation between macular blood flow and central visual sensitivity in retinitis pigmentosa," Acta Ophthalmologica, vol. 93, no. 8, pp. e644-e648.

Nakanome Y, Karita K, Izumi H, Tamai M. (1995) Two Types of Vasodilatation in Cat Choroid Elicited by Electrical Stimulation of the Short Ciliary Nerve. Exp Eye Res. 60:37-42.

Punzo C, Kornacker K, and Cepko C L. (2009) "Stimulation of the insulin/mTOR pathway delays cone death in a mouse model of retinitis pigmentosa," Nature Neuroscience, vol. 12, no. 1, pp. 44-52.

Reiner A, Fitzgerald M C, Li C. (2012) Neural Control of Ocular Blood Flow. In: Schmetterer L, Kiel J, editors. Ocular Blood Flow. Berlin Heidelberg: Springer, pp. 243-309.

Sahel, J. A., Le' veillard, T., Picaud, S., Dalkara, D., Marazova, K., Safran, A., Paques, M., Duebel, J., Roska, B., and Mohand-Said, S. (2013). Functional rescue of cone photoreceptors in retinitis pigmentosa. Graefes Arch. Clin. Exp. Ophthalmol. 251, 1669-1677.

Shih Y F, Fitzgerald M E, Cuthbertson S L, Reiner A. (1999) Influence of Ophthalmic Nerve Fibers on Choroidal Blood Flow and Myopic Eye Growth in Chicks. Exp Eye Res. 69:9-20

Venkatesh A, Ma S, Le Y Z, Hall M N, Rüegg M A, Punzo C. (2015) Activated mTORC1 promotes long-term cone survival in retinitis pigmentosa mice. J Clin Invest. 125 (4):1446-58.

Wang W, Lee S J, Scott P A, Lu X, Emery D, Liu Y, Ezashi T, Roberts M R, Ross J W, Kaplan H J, Dean D C. (2016) Two-Step Reactivation of Dormant Cones in Retinitis Pigmentosa. Cell Rep. 15(2):372-85.

Wolf S., Pöstgens H., Bertram B., Teping C., and Reim M. (1991) "Hemodynamic findings of patients with retinitis pigmentosa," Klinische Monatsblätter für Augenheilkunde, vol. 199, no. 5, pp. 325-329.

Zhang Y, Harrison J M, Nateras O S, Chalfin S, and Duong T Q. (2013) "Decreased retinal-choroidal blood flow in retinitis pigmentosa as measured by MRI," Documenta Ophthalmologica, vol. 126, no. 3, pp. 187-197.

Zong-Yi Li,' Ivar J. Kljavin, and Ann H. Milam. (1995) Rod Photoreceptor Neurite Sprouting in Retinitis Pigmentosa. The Journal of Neuroscience, 75(8): 5429-5438

| Publication number | Priority date | Publication Date | Assignee | Title |
|---|---|---|---|---|
| NZ214348A | 1985 Nov. 27 | 1988 Jul. 28 | Walker T H & Sons Ltd | Electrically stunning animals through nose and neck contacts |
| US4926880A | 1988 Nov. 08 | 1990 May 22 | Microcurrents | Method for relieving sinus and nasal congestion utilizing microcurrents |
| RU1799577C | 1989 Aug. 17 | 1993 Mar. 07 | 07Межотраслевой научно-технический комплекс Микрохирургия глаза | "Method for improving vision function affected by ophthalmic nerve and retina disease |
| US5099829A | 1990 Apr. 25 | 1992 Mar. 31 | Wu An Chuan | Massage device good for eyes |
| US5072724A | 1990 Nov. 23 | 1991 Dec. 17 | Joseph Marcus | Vibrational liquid-wave stimulating therapy mask apparatus for facial health and beauty care |
| US5360438A | 1993 Jan. 26 | 1994 Nov. 01 | Fisher Mary R | Method and device for improving cranial nerve function to improve muscle function and thereby overcome visual/perceptual dysfunction |
| US5713833A | 1994 Jan. 26 | 1998 Feb. 03 | Milligan; Lee John | Septum nerve stimulator |
| US5800685A | 1996 Oct. 28 | 1998 Sep. 01 | Cardiotronics Systems, Inc. | Electrically conductive adhesive hydrogels |

-continued

| Publication number | Priority date | Publication Date | Assignee | Title |
|---|---|---|---|---|
| US6458157B1 | 1997 Aug. 04 | 2002 Oct. 01 | Suaning Gregg Joergen | Retinal stimulator |
| US6020445A | 1997 Oct. 09 | 2000 Feb. 01 | Johnson & Johnson Vision Products, Inc | .Silicone hydrogel polymers |
| US6083251A | 1997 Nov. 13 | 2000 Jul. 04 | Shindo; Kohei | Eye treatment method and apparatus |
| US6324429B1 | 1998 May 08 | 2001 Nov. 27 | Massachusetts Eye And Ear Infirmary | Chronically implantable retinal prosthesis |
| US6035236A | 1998 Jul. 13 | 2000 Mar. 07 | Bionergy Therapeutics, Inc | Methods and apparatus for electrical microcurrent stimulation therapy |
| US7146209B2 | 2000 May 08 | 2006 Dec. 05 | Brainsgate, Ltd | .Stimulation for treating eye pathologies |
| US7120489B2 | 2000 May 08 | 2006 Oct. 10 | Brainsgate, Ltd. | Method and apparatus for stimulating the sphenopalatine ganglion to modify properties of the BBB and cerebral blood flow |
| US6526318B1 | 2000 Jun. 16 | 2003 Feb. 25 | Mehdi M. Ansarinia | Stimulation method for the sphenopalatine ganglia, sphenopalatine nerve, or vidian nerve for treatment of medical conditions |
| JP4781576B2 | 2001 Feb. 28 | 2011 Sep. 28 | 株式会社ニデック | Intraocular implantable visual stimulation device |
| US7321795B2 | 2003 Mar. 24 | 2008 Jan. 22 | Les Bogdanowicz | Compositions for electric stimulation of the eye |
| JP2007044323A | 2005 Aug. 11 | 2007 Feb. 22 | Nidek Co Ltd | Eyesight regeneration supporting apparatus |
| US8311634B2 | 2006 Jun. 16 | 2012 Nov. 13 | Second Sight Medical Products Inc | .Apparatus and method for electrical stimulation of human retina |
| US20080183242A1 | 2007 Jan. 29 | 2008 Jul. 31 | Nidek Co., Ltd | Electrical stimulation method for vision improvement |
| JP4970069B2 | 2007 Jan. 30 | 2012 Jul. 04 | 株式会社ニデック | Vision regeneration assisting device |
| SU1560205A1 | 1987 Apr. 27 | 1990 Apr. 30 | Пензенский государственный институт усовершенствования врачей | Device for intranasal vibromassage |
| US4911149A * | 1984 Jun. 18 | 1990 Mar. 27 | Urological Instruments Research, Inc | .Vibratory treatment method and apparatus |
| SU1560205A1 | 1987 Apr. 27 | 1990 Apr. 30 | Пензенский государственный институт усовершенствования врачей | Device for intranasal vibromassage |
| US9872814B2 | 2012 Mar. 20 | 2018 Jan. 23 | Chordate Medical Ag | Vibration pattern for vibration stimulation |
| US9474684B2 | 2012 Mar. 20 | 2016 Oct. 25 | Chordate Medical Ab | Electroactive vibration method |
| US9895279B2 | 2011 Dec. 16 | 2018 Feb. 20 | Chordate Medical Ab | Stimulation of hypothalamus |
| WO2013165697A1 | 2012 Apr. 30 | 2013 Nov. 07 | Vigilant Medical Solutions, Inc | Indirect and non-invasive trigeminal neuromodulation for the treatment of disease |
| US9440065B2 | 2013 Apr. 19 | 2016 Sep. 13 | Oculeve, Inc | Nasal stimulation devices and methods |
| US9687652B2 | 2014 Jul. 25 | 2017 Jun. 27 | Oculeve, Inc | Stimulation patterns for treating dry eye |
| US0195165A1 | 2006 Jan. 25 | 2006 Aug. 31 | Valam Corp, Gertner Michael | Optical therapy devices, systems, kits and methods for providing therapy to the body cavity |
| US7351253B2 | 2005 Jun. 16 | 2008 Apr. 01 | Codman and Shurtleff | Intranasal red light probe for treating Alzheimer's disease |
| US20110022130A1* | 2005 Jun. 16 | 2011 Jan. 27 | Dimauro Thomas MIntranasal | Red Light Probe For Treating Alzheimer's Disease |
| US20170225011A1 * | 2016 Feb. 08 | 2017 Aug. 10 | Ricky A. Frost | Laser device for intracranial illumination via oral or nasal foramina access |
| US9265967B2 * | 2011 Aug. 05 | 2016 Feb. 23 | Lumimed, Llc | Apparatus and method for treating rhinitis |

-continued

| Publication number | Priority date | Publication Date | Assignee | Title |
|---|---|---|---|---|
| US20170087377A1 * | 2015 Sep. 28 | 2017 Mar. 30 | DePuy Synthes Products, LLC | Transnasal Delivery of Low Level Light Via the Sphenoidal Sinus to Irradiate the Substantia Nigra |

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 10.D illustrates exemplary pulse width variations over time.

FIG. 17 A-B illustrates an exemplary construction of the hybrid electro-optical ONSor 1700 with an electrical stimulating sleeve 1708.

FIG. 18 A-B illustrates an exemplary construction of the hybrid electro-optical ONSor 1800

Figure 1:
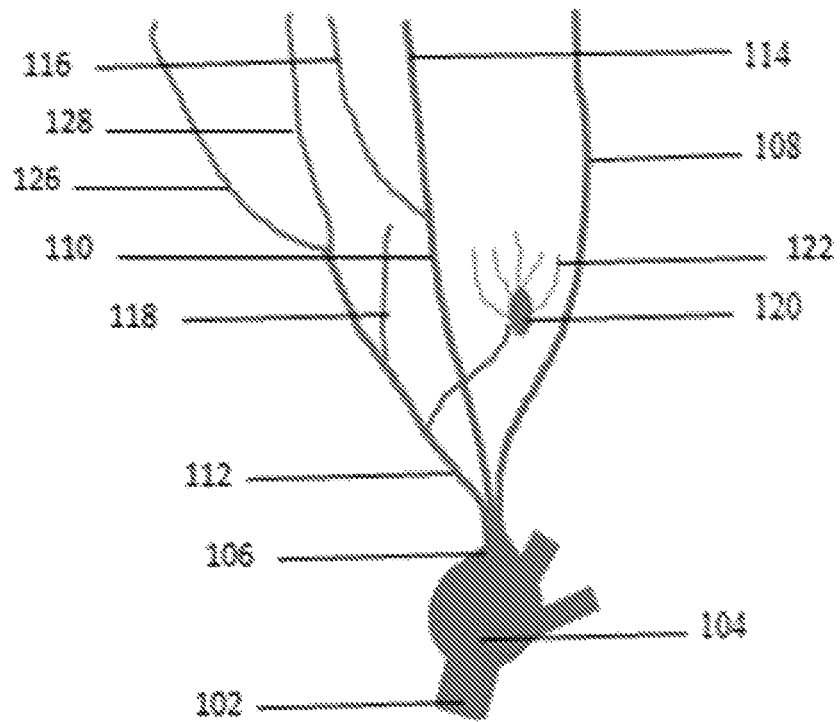
FIG. 1 illustrates ophthalmic division of trigeminal nerve

Unless otherwise defined, all technical and/or scientific terms used herein have the same meaning as commonly understood by one of ordinary skill in the art to which the invention pertains. Although methods and/or materials similar or equivalent to those described herein can be used in the practice or testing of embodiments of the invention, exemplary methods and/or materials are described below. In case of conflict, the patent specification, including definitions, will control. In addition, the materials, methods, and/or examples are illustrative only and/or are not intended to be necessarily limiting.

Implementation of the method and/or system of embodiments of the invention can involve performing or completing selected tasks manually, automatically, or a combination thereof. Moreover, according to actual instrumentation and/or equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Some embodiments of the invention are herein described, by way of example only, with reference to the accompanying drawings. With specific reference now to the drawings in detail, it is stressed that the particulars shown are by way of example and/or for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Overview

An aspect of some embodiments of the current invention relates to treatment method and/or system for treatment of the eye (e.g. improving night vision, central vision and/or color vision, contrast sensitivity and/or restoring vision and/or prevention of loss of vision). In some embodiments, the treatment includes neuromodulation. Optionally the neuromodulation is non-invasive. For example, the treatment may include up-regulation of the trigemino-vascular system TVS and/or activation of parasympathetic circuit of ocular circulation. For example, treatment objective may be achieved using ocular neuromodulation and/or inhibition of sympathetic activity. For example, inhibition of sympathetic activity may be applied when sympathetic activity is increased. Optionally, inhibition of sympathetic activity may be achieved via use of systemic anti-oxidants such as acute administration of intravenous ascorbic acid.

In some embodiment, expression of substance P (SP) and CGRP in the neurovascular tissue of the retina in response to selective stimulation of SP/CGRP-containing afferents small unmyelinated C fibers and medium-sized Aδ fibers of V1 has a number of neuroprotective effects on the retina. In some embodiment, endogenous SP and/or CGRP are involved in vasodilatation and augmentation of OBF. In other embodiment SP enhances RPE proliferation, prevention of apoptosis of neural cells. It has suppressing effects on neuroinflammation of the retina. Still in other embodiments, expressed SP promotes the migration and differentiation of vascular endothelial cells as well as mobilization of EMSCs from the bone marrow to the circulation to accelerate tissue repair.

An aspect of some embodiments of the current invention relates to restoration of a physiological microenvironment that facilitated improved ocular blood flow OBF, washout of waste products and toxic substances. In some embodiments, treatment may be used to improve delivery of oxygen, glucose, vitamin A, antioxidants, hormones, humoral mediators, growth factors, stem cells and/or pharmacological agents to the targeted tissues of the retina, choroid and optic nerve, for example PR's, retinal pigment epithelium RPE, ganglion cells and/or other nerve cells of the retina. For example, the nutrients may be supplied to metabolically very active photoreceptors PRs in retinitis pigmentosa RP. In some embodiments, improved OBF may slow down inherited PRs death, decrease retinal inflammation, improve functional neuroplasticity, reduced neuroinflammation and/or create local conditions favorable to cell survival. In some embodiments, Ophthalmic Nerve Stimulation ONS may be used to target diverse pathophysiologies of retinal, choroidal and optic nerve disorders via the effects of expressed SP.

In some embodiments, ONS is supplied through a central connection with vagal nerve. For example, ONS to the vagal nerve may affect various hormones (for example insulin) for example, to provide better nutrition to neurons and/or the retina. Neuromodulation via sympatholytic effects of AA/NAC might further improve OBF. The invention, in some embodiments thereof, relates to the methods for preparation of ONS induced neuropeptides (SP & CGRP) rich plasma (NRP) for pen-ocular injection.

Taken together, ONS along with systemic administration of antioxidants such as AA and or periocular injection of NRP can orchestrate retinal regeneration by increasing OBF, enhancing oxygen and glucose delivery to the starving PRs, repair of damaged RPE via SP-related proliferation and prevention of TNF-α induced loss of intercellular junction, preservation of healthy competent outer and inner blood retinal barriers, reduction of neuroinflammation of the retina, inhibition of apoptosis, and helped to prepare a better microenvironment for the survival and engraftment of the incoming SP-mobilized reparative endogenous stem cells.

Specific Embodiments

Before explaining at least one embodiment of the invention in detail, it is to be understood that the invention is not necessarily limited in its application to the details of construction and/or the arrangement of the components and/or methods set forth in the following description and/or illustrated in the drawings and/or the Examples. The invention is capable of other embodiments or of being practiced or carried out in various ways.

In some embodiments, a potential subject is identified. For example, a subject may be a person who is identified as affected by and/or at risk for dysregulated reduced OBF and/or inherited retinal disorders wherein said retinal disease include, but are not limited to rod cone dystrophy as retinitis pigmentosa (RP), Usher syndrome, Cone Rod Dystrophy (CRD), or congenital achromatopsia, x-linked choroideraemia. For example, a person may be identified having pigmentosa (RP), congenital achromatopsia (CA) and/or inherited retinal disorders (IRDs). For example, a subject may be identified who is suffering and/or prone to suffering from a disease or condition associated with reduced OBF, particularly the retina and/or choroid.

In some embodiments, a potential subject is identified. For example, a subject may be a person who is identified as affected by and/or at risk for dysregulated reduced OBF and/or acquired acute retinal disorders wherein said retinal disease include, but are not limited to acquired acute retinal disorders wherein said retinal disease include, but are not limited to, ophthalmic artery occlusion, central retinal artery occlusion, branch retinal artery occlusion, central retinal vein occlusion, and branch retinal vein occlusion, retinal capillary ischemia.

In some embodiments, a potential subject is identified. For example, a subject may be a person who is identified as affected by and/or at risk for dysregulated reduced OBF and/or acquired chronic retinal disorders wherein said retinal disease include, but are not limited to diabetic retinopathy, diabetic maculopathy, toxic maculopathy, radiation retinopathy, central serous chorioretinopathy In some embodiments, a potential subject is identified. For example, a subject may be a person who is identified as affected by and/or at risk for dysregulated reduced OBF and/or acquired acute choroidal disorders wherein said choroidal disorders include but not limited to macular drusen, age related macular degeneration (AMD) dry and wet types, non-age related choroidal ischemia, diabetic choroidal ischemia, macular retinal pigment epithelial atrophy, retinal pigment epithelial detachment.

In some embodiments, a potential subject is identified. For example, a subject may be a person who is identified as affected by and/or at risk for dysregulated reduced OBF and/or inherited and acquired optic nerve disorders wherein said optic disorders include, but are not limited to, anterior ischemic optic neuropathy, posterior ischemic optic neuropathy, and ischemic optic neuropathy associated with giant cell arthritis, glaucomatous optic neuropathy associated with high, normotensive and low tension glaucoma, traumatic optic neuropathy, inflammatory optic neuropathy, nutritional optic neuropathy, toxic and drug induced optic neuropathy, radiation optic neuropathy, idiopathic optic neuropathy.

In some embodiments, the subject may be monitored for example, to determine when to treat, whether to treat and/or how to treat his condition. Methods may optionally include monitoring the subject for prophylactic treatment where the patients are at pre-clinical stage of the disease for example early stage of DR, macular drusen of AMD, and preclinical stage of RP. The OBF of subjects who had received neuromodulation treatment may also be monitored for example to determine a need of re-treatment. For example, prophylactic treatment may be applied where the patients are at pre-clinical stage of the disease.

In some embodiment treatment may include nerve stimulation. For example, the ophthalmic division of trigeminal nerve (V1) may be stimulated. Optionally, stimulation may include regulation (for example up regulation) of trigemino-vascular system (TVS) and/or trigeminal autonomic brain reflexes (TABRs) and/or pancreatic Trigemino-vagal reflex (TVR) and/or anti-inflammatory TVR. For example, the site of stimulation of V1 include; mucosa of nasal septum of the vestibule, skin of nasal bridge, forehead, upper eyelids. In some embodiments, the subject's TVS and/or autonomic nervous system (ANS) are modulated in a manner that is effective to treat the subject for retinal, choroidal and/or optic nerve disorders e.g. RP, AMD, and/or ION.

In some embodiments, treatment may include the regulation of the subject's sympathetic nervous system (SNS). For example, the SNS may be is down regulated centrally by pharmacological agents. For example, acute intravenous administration of mega doses of ascorbic acid.

In some embodiments, sufficient ONS is employed to enhance SP/CGRP expression in the external jugular vein EJV. Blood sample from EJV can be used for preparation of N/PRP. For example, subtenon's' injection of freshly prepared N/PRP has regenerative effects on retina and optic nerve.

In some embodiments, the site of stimulation of V1 includes; nasal vestibule (Septal branch of anterior ethmoid nerve AEN), nasal bridge (external nasal nerve and/or infratrochlear nerve), forehead (supraorbital and/or supratrochlear nerve) and upper eye lids.

In some embodiments, treatment may be applied via a handheld device. For example, a treatment device may include a nose supported stimulator probe and/or a near Infrared (NIR) or blue light Delivery system. Optionally a device may have a stimulator body and/or a stimulator probe. For example, the device may include one or more intra-nasal and/or extra-nasal application heads. The signal may include, for example, vibration, chemical, ultrasonic, optical, electrical, hybrid electro-optical and/or a combination of two or more of these types of stimuli.

The treatment optionally increases OBF to the retina and/or choroid and/or optic nerve head. The treatment optionally, improves delivery of oxygen, glucose, vitamin A, insulin, humoral mediators, growth factors, stem cells and/or pharmacological agents to the targeted tissues, choroid and optic nerve and/or the retina. For example, therapeutic compound may target PRs of the retina.

Without limiting the invention to a theoretical framework, in some embodiments, chronic ONS may initiate a glutamate mediated retrograde signaling coupled with spillover of glutamate into choroid. Glutamate release may increase vascular permeability and/or breakdown of blood retinal barriers (BRB). Spillover of glutamate into choriocapillaries, along with breakdown of BRB induced by ONS might increase extracellar glutamate in the outer retina, thereby restoring transduction of signaling in cone photoreceptors through uptake of spilled glutamate e.g. as in cases of congenital achromatopsia CA.

In some embodiments, via stimulation of V1 at one or more sites may cause up regulation of TVS and/or TABRs. For example, up regulation of TVS and/or stimulation of V1, may include V1 sensory fibers innervating ophthalmic artery, ciliary arteries, and/or choroidal blood vessels containing neuropeptides such as SP and/or CGRP. These neuropeptides are potent vasodilating agents will be released from V1 nerve endings in response to ONS causing a robust vasodilator effect and/or increased OBF. Optionally, a specific portion of ANS is modulated causing a robust vasodilator effect and/or increased OBF. Additionally or alternatively, a specific portion of ANS may be modulated. For example, modulation may affect vagal nerve stimulation which affects insulin secretion by beta cells of islets of Langerhans. For example, excess insulin may increase glucose uptake and/or glycolysis by starving PRs promoting their survival. Alternatively or additionally, vagal nerve stimulation may activate anti-inflammatory effects on the retina and/or choroid and optic nerve.

In certain embodiment, selective stimulation of SP/CGRP-containing afferents small unmyelinated C fibers and medium-sized Aδ fibers of V1 may offer a wide range of effects on the retina including those involved in vasodilatation, augmentation of OBF, RPE proliferation, prevention of apoptosis, suppressing neuroinflammation, promoting the migration and differentiation of vascular endothelial cells as well as mobilization of endogenous bone marrow stem cells EBMSCs from the bone marrow to the circulation to accelerate tissue repair In certain embodiment, a targeted autonomic circuit is modulated by increasing the parasympathetic activity. In certain embodiment the targeted autonomic circuit is modulated by increasing the parasympathetic and/or decreasing the sympathetic activity. In certain embodiment the targeted autonomic circuit is modulated by increasing the parasympathetic/sympathetic activity ratio.

In certain embodiment, the targeted autonomic circuit of the eye is modulated by increasing the parasympathetic activity via ONS and/or decreasing the sympathetic activity by pharmacologic neuromodulating agent such as intravenous administration of antioxidants to produce sympatholytic effect on the targeted autonomic circuit and/or to reduce the ocular vasomotor tone In some variations, the devices described here include a Single Module device producing one type of stimulation such as vibration. In some variations, the devices described here are bi-modular devices using two types of stimulation such as vibration and/or chemical stimulation or hybrid electro-optical stimulation. In some variations, the system described here are multi-modular and/or composed of a number of modules which produce various types of stimuli such as vibrotactile, chemical, photic, electrical, ultrasonic, or hybrid electro-optical module. In some variation, the devices are handheld, portable body with nose supported stimulator probe. The multi-modular device is table mounted with a number of modules having stimulating probes.

In some embodiments, treatment is applied using a Single Mode, vibrotactile ophthalmic nerve stimulator (V-ONSor): In some variation, stimulator is handheld vibrotactile devices. In some of these variations, the device includes a portable nose-supported butterfly like frame glasses. In other variations, the stimulator is portable with nasally clipped applicators. Vibrotactile stimulators deliver low magnitude, high frequency vibration (LMHFV) stimulus to branches of V1. The intranasal application head comprises a polycarbonate, or any other material suitable to transmit vibration and/or reduce heat energy produced by vibration. In some variation, the disposable intranasal stimulator probe includes a smooth face of the application head that comes in contact with the mucosa of the nasal septum of the vestibule. In some variations, the application head has V-shaped pattern that rests over the nasal bridge during administration of ONS. In some variations, the head has single or double or multiple heads with a flat faces that rest on one or two sides of the forehead during administration of ONS. In some variations, the device further comprises a user interface. In some of these variations, the user interface comprises one or more operating mechanisms to adjust different parameters of the stimulus such as the frequency of stimulus (between 40 Hz and 90 Hz.), the amplitude (more or less than 1.5 μm, the duty cycle (less or more than 50%) type of waveform (rectangular, sinusoidal, etc.) and/or the duration of session in minutes. In some of these variations, the device has a pre-programmed features designed for patient use at home or by treating doctors in clinics.

In some embodiments, treatment is applied using a Single Mode, chemical ophthalmic nerve stimulator (Ch-ONSor): In some variation, stimulator is handheld devices with a micro pump incorporated in its application head. TRPM8 agonists are used for chemical stimulation of V1. In some of these variations, the device is hand held bi-modalular (vibro-chemical mode). With pre-programmed features designed for patient use at home or by treating doctors in clinics.

In some embodiments, a treatment device may include a Single Mode, handheld, Ultrasonic ONSor with intranasal application head. For example, the device relates to pulsed ultrasonic nerve stimulation device for stimulating V1. Low frequency ultrasound is typically in the range of 0.3 MHz to 8 MHz or above. A rate of 300 Hz (or lower) may cause inhibition (down-regulation). A rate in the range of 500 Hz to 5 MHz may cause excitation (up-regulation). Power is generally applied at a level less than 60 mW/cm$^2$. Under the influence of the ultrasonic frequency DC current, the ultrasound transducer resonates, expands and/or contracts volumetrically, in tune with the frequency supplied by the electronic frequency generator module and/or thereby converting the electronic energy into ultrasonic pressure waves. These ultrasonic pressure waves are impacting nasal septal mucosa and/or stimulate septal branch of AEN.

In some variations, the devices described here includes a Single Mode, portable, optical Op-ONSor. For example an Op-ONSor may include a nose supported stimulator probe, and/or intranasal application head in the form of a tube emitting blue light (e.g. 480 nm) toward the nasal mucosa. In some variation it emit a pulsed blue light with wavelength of about 480 nm (e.g. between 475 to 485 nm and 460 to 470 nm) to stimulate melanopsin containing unmyelinated C nerve fibers of V1. In other variations the tube is emitting pulsed near infrared (NIR) light (for example between 750 to 850 nm and about 810 nm) toward the AEN underneath the mucosa of nasal vestibule. In some variations, the device further comprises a user interface. In some of these variations, the user interface comprises one or more operating mechanisms to adjust different parameters of the stimulus such as the frequency of stimulus (between 10 Hz and 40 Hz.), the energy output (10 mW/cm$^2$-40 mW/cm$^2$), duty cycle (less or more than 50%), and/or the exposure time minutes (5-25 minutes).

In some embodiments, the present invention provides an apparatus and a method for optical, electrical or by hybrid electro-optical stimulation of neurons of V1 in the nasal cavity to obtain a physiological response in a subject (e.g., increased OBF) and to treat retinal choroidal and optic nerve diseases caused by reduced dysregulated OBF. In some embodiments, one or more electrodes are placed adjacent the AEN, a branch of V1 intranasally to provide a sensitizing stimulation signal that, by itself, would not be sufficient to trigger a nerve action potential (NAP), but when combined with an optical stimulation signal applied in temporal proximity, enhances the probability of triggering a desired NAP along the V1

In some embodiments, treatment is applied using a Single Mode, portable, electric ONSor: This invention in some embodiments thereof relates to portable transcutaneous electrical nerve stimulation (TENS) devices for stimulating V1. More specifically, some embodiments of the invention relate to a TENS device that operates in the electrical current range of about 0.7 mA to 3.5 mA, using a frequency ranged from 20-60 Hz. The devices are configured to deliver a pulse-based electrical waveform, which might be biphasic, alternating monophasic, or monophasic or the like. In some variations, the devices described here are a single module, with portable case, and/or disposable intranasal application head. The intranasal application head might be self supported in the form of intranasal septal clip, or extra nasal application heads with nasal bridge clips. In other variations the adhesive electrodes of the E-ONSor were applied to the forehead or upper eyelid of the subject. In some variations, the devices described here are a single module, portable handheld device, comprised a stimulator body, and/or intranasal stimulator probe, with one or two intranasal application heads. The intranasal head carrying one or more electrodes is simple with a smooth face that comes in contact with the mucosa of the nasal septum of the vestibule. A return electrode might be allocated on the application head in contact with skin of nasal opening or incorporated in the body of the stimulator probe In some variations, the device further comprises a user interface. In some of these variations, the user interface comprises one or more operating mechanisms to adjust different parameters of the stimulus such as the frequency of stimulus (between 20 Hz and 60 Hz.), the amplitude (0.7 mA to 3.5 mA), amplitude modulation frequency (2-2.5 Hz), pulse width (0-300 μs) Pulse width Modulation (1 Hz), the duty cycle (less or more than 50%) type of waveform (rectangular, sinusoidal, etc.) and/or the duration of session in minutes (2-5 minutes).

In some embodiments, treatment is applied using an ONSor for generation of N/PRP derived from blood of the external jugular vein. Described here are methods for treating ocular disorders by providing sufficient ONS followed by preparation of N/PRP with high SP/CGRP content from EJV blood samples. The N/PRP, when delivered to the subtenon's space in patients with ocular disorders, for example IRDS such as RP, as described herein, is capable of initiating a diverse set of pathways, including those involved in vasodilatation, augmentation of OBF, RPE proliferation, prevention of apoptosis, suppressing neuroinflammation, promoting the migration and differentiation of vascular endothelial cells as well as mobilization of EBMSCs from the bone marrow to the circulation to accelerate tissue repair of the diseased retina as in RP.

In some embodiments, disclosed are devices, systems and/or methods include a non-invasive neuromodulation system for treating AMD, CRAO, RP, CA and/or IRDs caused by dysregulated reduced OBF by up-regulation of TVS and/or TABRs through stimulation to V1. Additionally or alternatively, the subject's SNS is down-regulated centrally by pharmacological agents such as intravenous administration of ascorbic acid.

In some embodiments, devices and/or systems are used to treat ocular disorders e.g. retinal, choroidal or optic nerve disorders. For example, the methods may comprise stimulating V1 nerve at one more sites to increase OBF, improve the delivery of oxygen, glucose and/or essential nutrient for retinal PRs, and/or enhance insulin secretion from pancreases, and/or improve ocular health. The methods may further comprise treating ocular disorders by regular activation of the TVS and/or TABRs through up regulation of PNS, and/or restoring autonomic balance and/or this aimed to enhance the neural plasticity and/or maintain long term effects.

The methods of the invention in some embodiments thereof may further include identifying a subject prone to or suffering from a disease or condition associated with reduced OBF, for example the retina and/or choroid. Methods of the invention, in some embodiments thereof, may also include monitoring the subject for prophylactic treatment where the patients are at pre-clinical stage of the disease. The OBF of subjects who had received neuromodulation treatment may also be monitored for the need of re-treatment.

In some of these variations, the ONS device may be programmed according to the specific requirement needed for treating retinal/choroidal/optic nerve disorders, as an example RP, AMD, ION. Some or all features ONS can be adjusted, such as duration of session, frequency of stimulation, stimulus power, duty cycle, pulse characters. Programming might include features of each session over the whole treatment period. Day one session might differ regarding the duration of ONS compared to the 7th day of treatment protocol. In some of these variations, the device can be programmed for home use by the patient according to the specific requirement needed for treating RP AMD, and/or ION with dysregulated OBF. In some embodiments, for this type of devices, only the treating doctor has the access for programming these devices.

In some variations, the methods described here comprise methods for treatment of retinal, choroidal and/or optic nerve disorders. In some variations, the standard protocol of ONS is administered once or twice daily for 2 weeks. In some variations, the standard protocol of ONS is administered once or twice daily for 3 weeks. In some variations, the protocol of ONS is administered once or twice daily for 3-6 days as retreatment of RP and/or AMD. In some variations, the protocol of ONS is administered once or twice daily for one week as a preventive treatment of RP and/or DR. In some variations, the protocol of ONS is administered once or twice daily for a specific period that varies according to the type of ONS, the nature and severity of the ocular disease and response of the patient.

In some embodiments, the methods disclosed herein include stimulating V1 by different methods including vibrotactile, chemical, ultrasonic, optical, electrical and/or electro-optical methods. The stimulating agent will stimulate branches of V1 directly, or indirectly providing sensory information back to the CNS and/or ocular blood vessels, pancreas or the nasal mucosa and/or sub-mucosa. With that approach, neural tissue may be activated in some manner.

Figure 2:
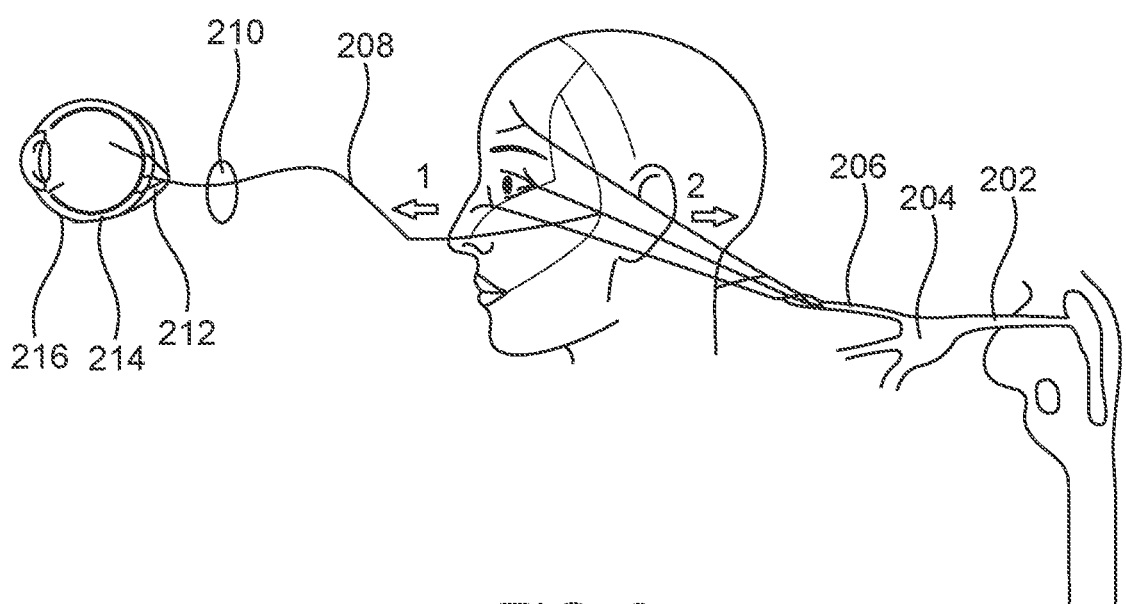
FIG. 2 illustrates a proposed pathway of trigeminovascular system (TVS).
Figure 3:
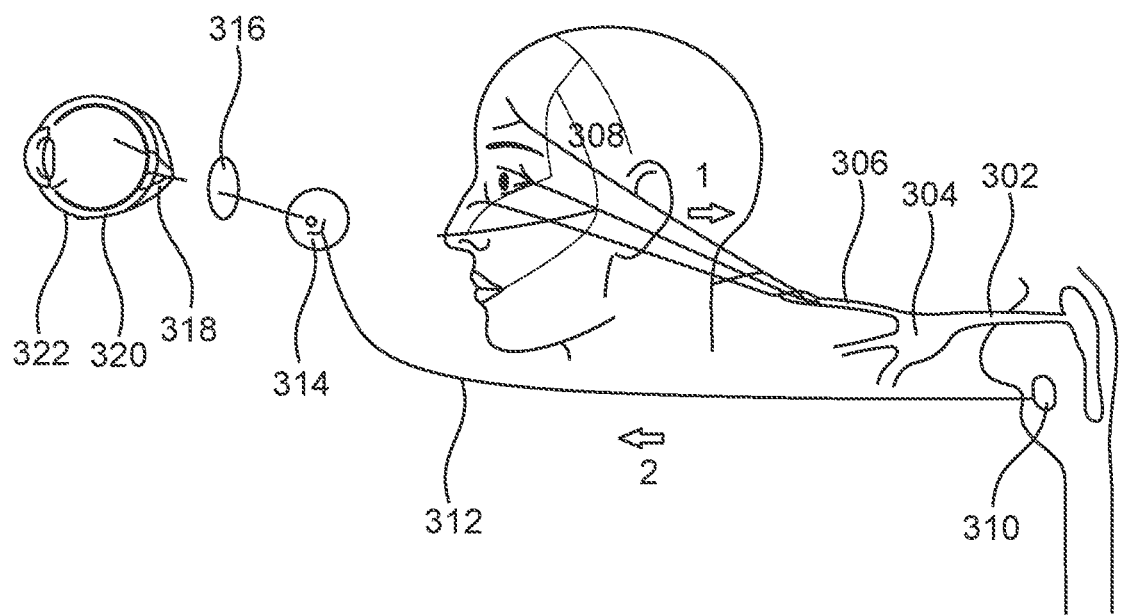
FIG. 3 illustrates a proposed pathway of trigemino-autonomic brain reflex. The facial nerve presented as the efferent limb of the reflex.
Figure 5:
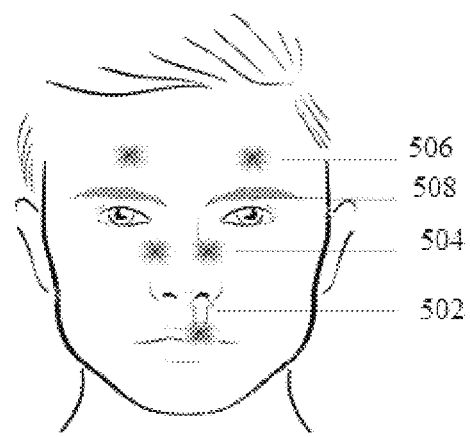
FIG. 5 illustrates exemplary sites of stimulation of V1.

For example, referring to FIG. 5, without limiting the ideas to a theoretical framework, a possible mechanism of action includes that the activation at an intra-nasal 502 or extra-nasal locations 504, 506, 508, 510 may cause action potentials to run antidromically back to the eye (arrow 1) FIG. 2 and/or orthodromically from the activation point to cause sensory input to the brain (arrow 2). Sensory input to the brain reaches the brain stem, after passing several ganglia on the way, as shown by arrow 2. Accordingly, the activation of neural tissue, directly or indirectly, may cause circuitry in the CNS (e.g., brain, potentially the ganglia in the peripheral cranial nervous system) to respond to the input. Output from the brainstem may then send feedback, as shown in FIG. 3 by arrow 2, to the eye and/or ophthalmic artery branches causing increased OBF.

Illustrative embodiments of the invention, in some embodiments thereof, are described herein. It will be apparent to those skilled in the art, that is, to those who have knowledge or experience in this area of technology, that many uses and/or design variations are possible for the devices for V1 stimulation. The following detailed discussion of various alternative and/or preferred features and/or embodiments will illustrate the general principles of the invention, in some embodiments thereof, with reference to non-invasive devices for stimulating V1. It is important to point out that not all features of an actual implementation are described in this specification. In the development of any such actual embodiment, numerous implementation-specific decisions may be made to achieve the design-specific goals, which will vary from one implementation to another. It will be appreciated that such a development effort, while possibly complex and/or time-consuming, would nevertheless be a routine undertaking for persons of ordinary skill in the art having the benefit of this disclosure. Other embodiments suitable for other applications will be apparent to those skilled in the art given the benefit of this disclosure.

In some embodiments, the devices and/or systems may be configured for non-invasive stimulation of branches of V1. The devices may be single mode devices or multi-modal systems Single Mode Devices:

In some variations, the devices may comprise a single mode for ONS. The device delivers one type of ONS include exemplary embodiments of vibrotactile ONSor devices 600, 800, 900, chemical ONSor device 1100, Ultrasonic ONSor device 1400, optical ONSor device 1500, Electrical ONSor device 1900, 2000 and/or Electromagnetic ONSor device. Optionally Single Mode Devices are designed for patients use at home under supervision by experienced eye doctors. Additionally, it can be used in clinics and/or hospitals by professional ophthalmologist and/or medical staff Multimodal Machine:

In some variations the stimulation system described here may comprise two modules, (e.g. vibrotactile and/or chemical module 1300, hybrid electro-optical module 1700 and 1800). In some variations the stimulation system described here may be multimodular 2100, for example comprising three modules or more, (vibrotactile, chemical and/or photic module, ultrasonic, and/or electrical and or hybrid electro-optical module). In some variations the stimulation system described here may comprise of combination of two or more modules that produces vibrotactile, chemical, ultrasonic, light based, electrical, electromagnetic or the like. When the devices and/or systems are used to treat ocular disorders such as RP, CRD, CA, DR, AMD, ischemic optic neuropathy, the methods may comprise stimulating V1 to increase OBF, prevent deterioration of vision, restore lost vision, or improve ocular health. Optionally, Multimodular systems 2100 are designed for hospitals, institutions, and/or clinics for use by professional ophthalmologist or by other medical staff supervised by experienced eye doctors.

Site of Stimulation:

FIG. 5 illustrates some preferred sites for ONS. The site of stimulation includes nasal vestibule 502, nasal bridge 504, forehead and/or eye brows 506, and upper eyelids 508.

The nasal vestibule is the most anterior part of the nasal cavity. The mucosa of the anterior part of nasal cavity 502 receives sensory nerve supply from AEN, a branch of nasociliary nerve of V1.

The nasal bridge 504 is a convenient site for stimulation of V1. It is innervated by infratrochlear nerve, a branch of nasociliary nerve and external nasal nerve, the terminal branch of external branch of anterior ethmoid nerve, which is a branch of nasociliary nerve.

The skin of forehead 506 is innervated by supratrochlear and/or supraorbital nerves, branches of frontal nerve. The latter is a branch of V1. This site of stimulation may be suitable for patients with a history of nasal trauma or nasal septal surgery, and/or probable nerve damage to AEN. The upper eye lid 508 are innervated by lacrimal, supraorbital, and/or supratrochlear and/or infratrochlear nerves.

The Intranasal Pathway

A challenge of intranasal ONS was to make the application head small enough to fit comfortably and/or safely within the restricted size of the nasal vestibule. Intranasal pathway may have many potential advantages which include presence of plenty of different types of receptors on sensory nerve fibers of V1 that make stimulation of these receptors easier and/or more effective. V1 exhibits mechanosensory and/or chemosensory and/or photosensory nerve fibers and/or their specific receptors (e.g. mechanoreceptors, TRPM8, Melanopsin) in the nasal cavity that may makes vibrotactile and/or chemical and/or optical stimulation more selective and/or effective and/or might prove to have synergetic effects. Mechanosensory fibers are represented by large fast-conducting Aβ-fibers. Chemosensory fibers refer to thin and/or slow-conducting unmyelinated C-fibers and/or thin, fast-conducting myelinated Aδ-fibers that are involved in thermoreception (temperature perception) and/or nociception. Electrophysiological data indicate that an area of increased trigeminal chemosensitivity might be found at the anterior third of the septum. The presence of melanopsin containing nerve fiber in the trigeminal nerve makes V1 a natural target for optical stimulation to increase OBF. Furthermore, administration of vibrotactile, chemical, photic, ultrasonic, electrical or hybrid electro-optical stimulation trans-nasally may be advantageous as they may be located closer to important targets to be stimulated. This include AEN, SPG and/or midbrain area where much of the autonomic functions lie, with little barrier in between the source of stimulus and/or the target.

Vibrotactile ONS

The intranasal application head of the vibrotactile stimulator is designed to be small enough to fit comfortably and/or safely within the restricted size of the nasal vestibule and optionally made by polyethyl methacrylate to prevent the warming produced by the vibration of long periods. Intranasal pathway may have many potential advantages which include presence of plenty of mechanoreceptors. In some embodiment, low magnitude high frequency vibration LMHFV may selectively stimulate unmyelinated C nerve fibers containing SP/CGRP. For example, ONS increased SP/CGRP levels in neurovascular tissues of the eye and extra-cerebral blood vessels such as EJV. Therefore, EJV might be a preferential source for preparation of N/PRP for sub-Tenon's injection. Additionally, LMHFV might selectively activate PNS, for example, by using vibrotactile stimulus of approximately 89 Hz frequency and/or approximately 1.9 µm amplitude. Constant mechanical vibration applied to the skin may induces hypoesthesia, specifically, a reversible decrease in the perception of vibration at the stimulated site. This phenomenon may be defined as vibrotactile adaptation and/or is generally characterized by an increase of vibrotactile detection threshold or a reduction of vibrotactile sensibility. Without limiting the invention to a theoretical framework, according to two-channel theory, the transduction of low-frequency vibrations (10-60 Hz) is preferentially achieved by rapidly adapting type I (RA) and/or slowly adapting type I (SAI) mechanoreceptors whereas the transduction of high-frequency vibrations (200-300 Hz) is preferentially achieved by rapidly adapting type II Pacinian (RAII/PC) mechanoreceptors. For example, vibrotactile stimulation with a frequency of 20-90 Hz may be employed for of ONS in order to avoid rapidly adapting type I mechanoreceptors.

Figure 6:
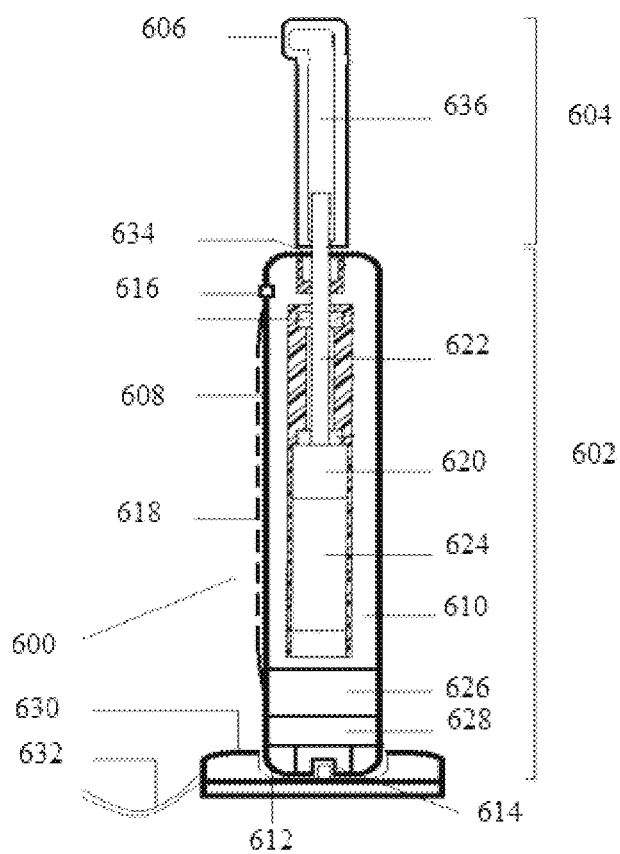
FIG. 6 depicts an exemplary handheld vibrotactile Ophthalmic Nerve stimulator (V-ONS 600).

FIG. 6 shows an exemplary diagram of a hand held VONSor 600. V-ONSor 600 is a single mode hand held device. The devices may comprise a stimulator body 602 and/or a stimulator probe 604 as illustrated in FIG. 6, where the stimulator probe ended with different types of stimulator probe application heads as shown in FIG. 7.B 752, 754, 756, and/or 758. Generally, the stimulator body 602 may be configured to generate a stimulus that may be delivered to the subject. The stimulator body 602 may comprise a front housing, back housing, and/or two side housing 608, which may fit together to define a body cavity 610 and the base 612. The body cavity 610 may contain a vibration power source 620 and/or control subsystem 624 and, which together with the user interface 618 located at the front housing may generate and/or control the vibrotactile stimulus.

Figure 7A:
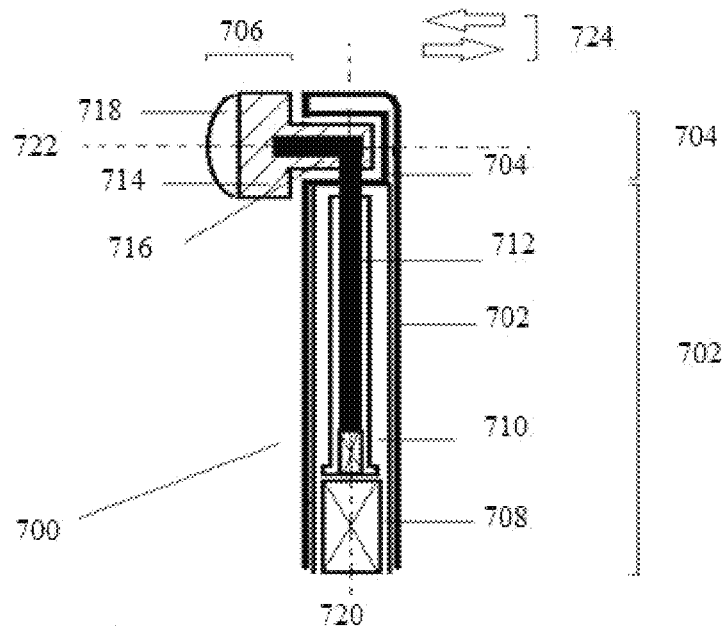
FIG. 7A illustrates distal portion of exemplary stimulator probe 700 for V-ONSor 600. FIGS. B and C illustrate various exemplary embodiments of disposable heads of the stimulator probe 750 and their covering 770.

FIG. 7A illustrates a stimulating probe 700 which may be push-fitted onto the body of the stimulator and/or the drive shaft of the V-ONSor 600. The stimulator probe 700 includes a mounting tube 702 extending in the direction of a longitudinal axis 720. At its free end close to the body of stimulator, the mounting tube 702 has a profile ring 708 with an inside contour 710 complementary with the outside contour of the body of stimulator. The inside and/or outside contours may be of a square, stellate or similar configuration when viewed in cross section, optionally the inside and outside contours are conformed to each other. In this manner, the stimulator probe 700 can be push-fitted onto the body of the stimulator in a manner inhibiting relative movement, while at the same time a secure seat of the stimulator probe 700 on the body of the stimulator is ensured. At its end remote from the body of the stimulator, the mounting tube 702 has a bearing 704 in which a shaft 712 is carried so as to be vibrating at the level vertical to the shaft. The shaft 712 is arranged in the longitudinal axis 720 of the mounting tube 702 and/or is preferably made of metal. The shaft 712 extends from the bearing 704 in the direction close to the body of stimulator approximately up to the center of the mounting tube 702. At its end remote from the body of the stimulator, the mounting tube 702 has a cap structure covering approximately the area by which the shaft 712 projects beyond the bearing 704 and/or thus beyond the mounting tube 702. Further arranged in this area are an application head 706 of the stimulator probe 700 as well as means for coupling the application head structure 706 to the shaft 712 and/or to the mounting tube 702. The application head structure 706 includes a disk-shaped plate 714 and/or a hub 716 and/or is essentially vibrating along the axis 722 disposed at an angle of about 90 degrees to the longitudinal axis 720. On its side facing away from the shaft 712, the plate 714 has a slightly curved smooth surface 718 covered by polymethyl methacrylate. When the V-ONSor is turned on, the drive shaft 622 projecting outwardly from the body of stimulator produces a vibration movement 724 coincides with the axis 722 and/or vertical to the longitudinal axis 720 and/or to the shaft 712 of the stimulating probe. In consequence, the application head executes a vibration movement along the axis 722. This means that the application head 706 performs approximately a forward and/or backward movement. This vibration movement produced by the application head of the stimulator probe 706 is employed to execute mechanical stimulation of the intra-nasal 502 or extra-nasal locations 504, 506 during vibrotactile ONS. The stroke length of the vibrating back-and forth motion 724 may advantageously lie in a range from about 1.5 µm about 3.5 µm. The frequency of the vibration may be between about 20 Hz and/or about 90 Hz.

Figure 7B:
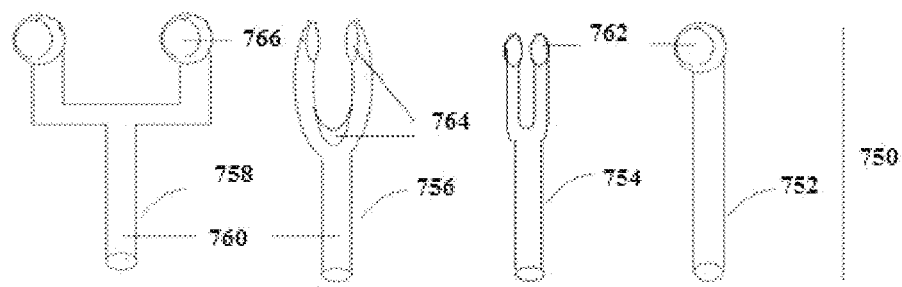

FIG. 7B illustrates exemplary types of stimulator probe for portable handheld V-ONSor 600. In some variations, the intranasal stimulator probe 752 may comprise at least one intranasal head, which may be configured to be easily inserted into the nasal cavity and/or come in contact with the nasal septum of the nasal vestibule of a subject or patient. In the handheld V-ONSor 600, the stimulator probe 754 may comprise two intranasal application heads in a way that the heads come in contact with mucosal lining of the nasal septum of both nasal vestibules.

In some variations, the stimulator probe may comprise a V-shaped head 756 for stimulation of the nasal bridge. Optionally, a facet is present on some arms and/or each arm of the V shaped head. The two limbs with their facets hold and/or contact the nose from sides, while the connecting point of the two arms rest on the nasal bridge.

In some variations the stimulator probe 758 may comprise two or more heads that can be applied simultaneously to touch both sides of the forehead.

Figure 7C:
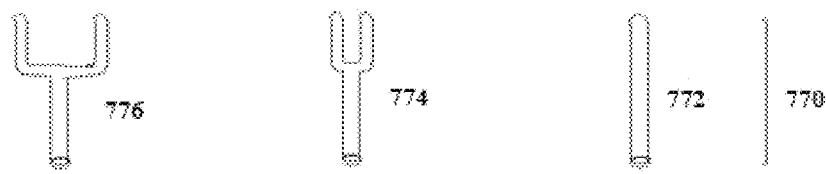

In some variations, the stimulator probe described here may comprise a thin silicone cap to protect the stimulator probe and/or its application head. For example, FIG. 7C show different types of silicone caps that can fit to various types stimulator heads. As shown there, the cap 772 may fit over the stimulator probe 752, while the cap 774 may fit over both the stimulator probe 754 and/or 756. The cap 776 may be suitable for stimulator probe 758. More particularly, for intranasal stimulator probes, it may be desirable for the cap to protect the nasal insertion site from contamination. In some variations, the cap might be impregnated with a TRPM8 agonist such as menthol.

In some embodiments, a stimulator probe 604 may be detachable. The connection 634 between the detachable probe and the rest of the device is optionally made in a manner to facilitate transmission of vibration from the stimulating body 602 to the head 606 of stimulator probe 604.

In some embodiments, a stimulus may be delivered to a subject via the head 606 of stimulator probe 604. The stimulator body 602 and/or stimulator probe 604 may be reversibly attachable. In variations where the stimulator probe and/or the stimulator body are not detachable, the stimulator probe is covered by disposable sterile cap. Detachable stimulator probes are optionally sterile and disposable. The head shape varies according to the site of stimulation. FIG. 7B. shows types of application heads for vibrotactile stimulation 752, 754, 756, 758.

The stimulator body 602 may comprise housing 608, a user interface 616, a control subsystem 624, and/or a power source 628. The user interface 618 comprising one or more operating mechanisms to adjust one or more parameters of the stimulus. For example, the operating mechanisms may allow the user to power the device on or off, start or stop the stimulus, change the frequency of the stimulus, change the duty cycle, change the duration of the stimulus, change the stimulus pattern, or the like. In some variations, the user interface may comprise one or more operating mechanisms, which may allow the user to use a predetermined protocol.

FIG. 6 shows a perspective view, of the stimulator body 602. The stimulator body 602 may have any suitable shape, such as cylindrical or tetragonal with blunted edges. In some variations, it may be desirable for the stimulator body 602 to be shaped such that it can be easily gripped by a user, such that it can be held with one hand. However, it should be appreciated that the stimulator body may have other shapes.

FIG. 6, a stimulator body 602 may have a flat base 512 ends with a circular small tunnel for energy connection 614 and/or a tapered proximal end that gives attachment to the stimulator probe 604. In some variation, the proximal end of the body 602 is continuous with the stimulator probe 604 with no joint between them.

For example, as mentioned above, the stimulator tetragonal body may comprise a housing 608. The front housing may also comprise openings configured to receive a number of small lights 616 (4 lights) that give an indication of status of battery. In some instances, it may be desirable for the stimulator body to be sealed, such that it may be waterproof or the like. In variations in which the housing comprises openings for other elements of the stimulator body (user interface, electrical connection at the base of the body, or the like), the interface between those elements and/or the stimulator housing may be watertight, and/or may comprise seals.

In some variations, housings may comprise a thermoplastic such as acrylonitrile butadiene styrene (ABS), polycarbonate, polyetherimide. However, the housing may comprise any suitable material or materials.

Figure 8:
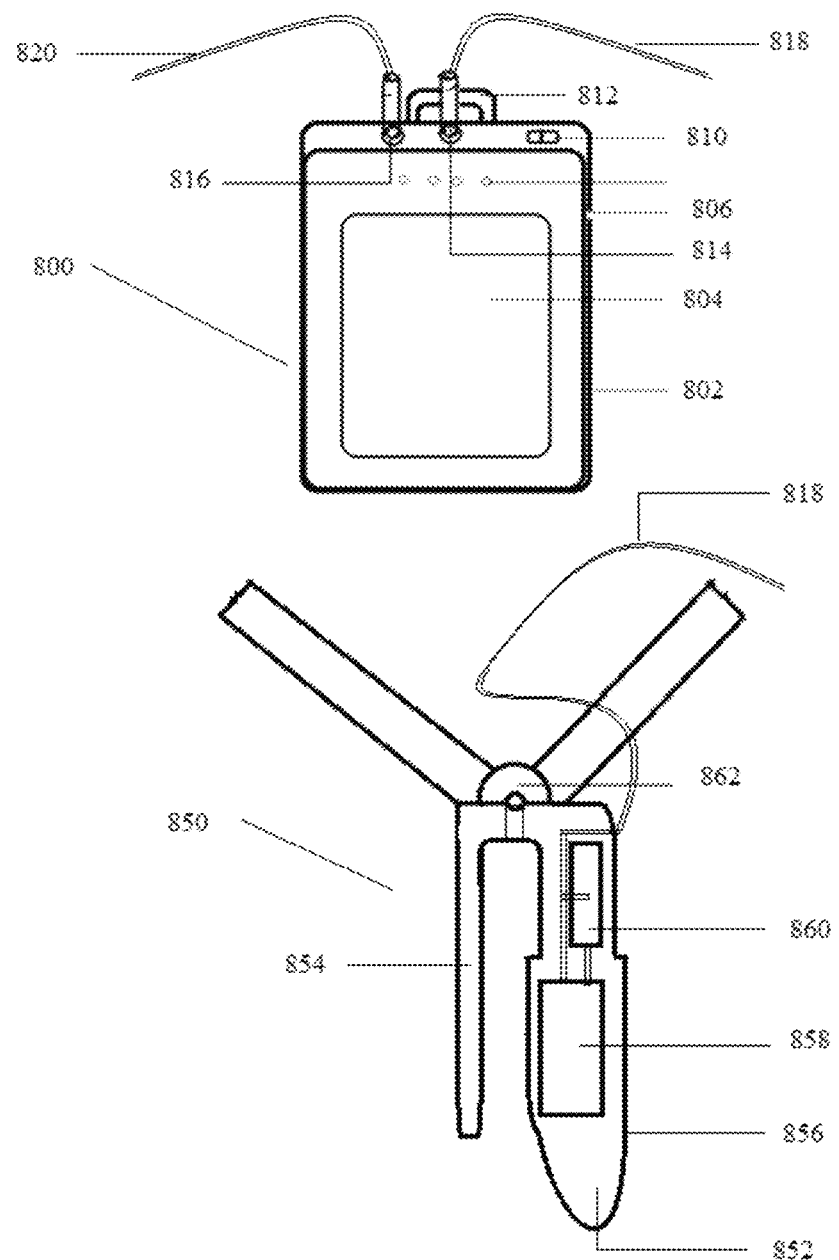
FIG. 8 depicts an exemplary embodiment of a portable V-ONSor 800 with its nasally clipped application head.

Portable V-ONSor 800 with Nasally Clipped Application Heads:

FIG. 8 illustrates one embodiment of the present invention wherein the V-ONSor 800 consists of a portable control unit 800 and/or vibration producing device 850. In this particular embodiment the case or housing of the control unit is equipped with a clip 812 that allows the unit to be worn on the shirt pocket or belt or the like during use. The other side of the case relative to the belt clip is equipped with a display 804 (user interface) which may be a touch screen that allows the user to adjust different parameters of the vibrotactile stimulus such as the frequency, amplitude, pulse width, shape of waveform etc., and/or modulating these parameters or select preset features of the stimulus. In some variations the system 800 delivers vibrotactile stimulation from application head 852 of the vibration producing device 850. The Control unit 800 of the system communicates with the vibration producing system 850 via power coupling 818. In some embodiment there are two vibration producing devices and/or both are connected to the control unit 800 via power coupling 818, 820. The application head 852 is designed to have round shaped tip that can be inserted easily in the nasal cavity and/or can be maintained in contact with nasal mucosa via nasal clips 854.

In some embodiments, the top face of the case 802 is further provided with an on/off switch 810 and/or a two power coupling 818, 820 connecting the vibration producing device 850 and/or the control unit 800 by two power outlets 814, 816 provided on the top face of the case 802. During administration of vibrotactile ONS, typically application head 852 is inserted into one nasal vestibule, touching the nasal mucosa of the septum and/or held in place via nasal clips 854.

In some embodiments, for example as shown in FIG. 8, the vibration producing device 850 comprises an application head 852 for providing vibrotactile stimulation to the nasal cavity in accordance with one embodiment of the present invention. The vibration producing device 850 in this embodiment generally includes a housing 856 and/or a vibration producing motor 558 positioned in or near the housing. The application head 852 is configured to be inserted into a target nasal cavity to stimulate V1 by administration of vibrotactile stimulation to nasal septum.

In some embodiments, housing 856 of the vibrotactile producing device 850 can be held in place by nasal clip 854 for an extended period of time (therapeutic time) without undue effort or discomfort, due to the lightweight, portable design of the device.

As will be appreciated by those skilled in the art, it may be desirable to control variables or control parameters associated with the output of the vibrotactile producing device 850. Examples of such variables include power, timing, frequency, duty cycle, shape of waveform. In one embodiment, the control circuit 860 controls the delivery of power from the power supply through the power coupling 1818 or 1820 to the vibration producing device 850 according to the activation or status of the controller 800. For example, in one embodiment, the control circuit 860 includes a relay, or a transistor. When the button 810 switch of the control unit 800 is pressed on, or activated, power from the power supply is able to flow through the control circuit 860 and/or the vibration producing system 858. For delivering a dose of vibrotactile ONS, a preset of waveform is selected, the application head is inserted into the nasal cavity, and/or the system is activated for specific duration. Vibrotactile ONS may be delivered into the nostrils in succession using single application head, or simultaneously using two application heads, with one application head is inserted into each nostril Portable Self Supported V-ONSor 900

Figure 9A:
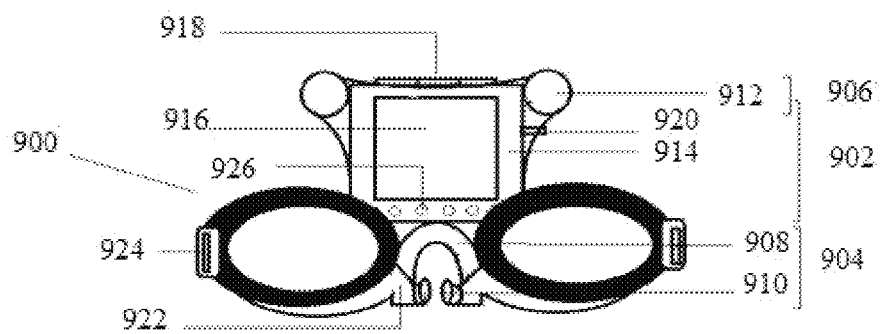
FIGS. 9 A and B depict an exemplary nasal supported version of V-ONSor 900
Figure 9B:
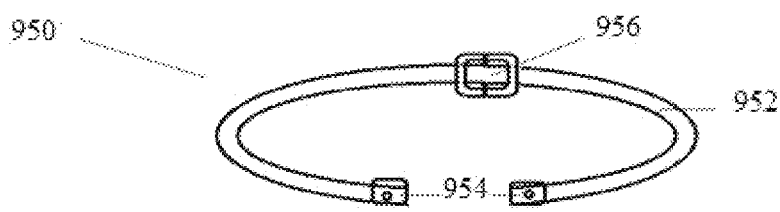

FIGS. 9A, 9B illustrates another version of a portable self supported V-ONSor 900 in the form of a butterfly like a glasses frame. The stimulator comprised two pairs of wings and/or a centrally located simulator body 902. In some variations, it may be desirable for the V-ONSor 900 to be self supported and/or easily adapted over the nasal bridge and/or fixed to the head of the subject using an adjustable elastic band 950 around the head circumference. The stimulator body 902 may comprise housing 914 a user interface 916, a control subsystem connected to control buttons 918 and/or a power source 920.

In some variations, the stimulation might be delivered by an inverted V-shaped application head 908 that rest over and/or stimulate the nasal bridge. The two arms of the V-shaped application head 908 with their facets hold and/or contact the nose from both sides, and/or the connecting point of the two arms rest over the nasal bridge.

In some variations, the V-ONSor 900 might be delivered vibrotactile stimulation intranasally via two intranasal application heads 910. In this case the vibrotactile stimulation is transmitted via two limbs 922 extending from the inferior part of the stimulator body as an extension of inverted V-shaped nasal bridge application head 908. At each end of these two limbs, an application head 910 is located and/or designed in a way to come in contact with the nasal septal mucosa.

In some variations, the V-ONSor 900 might be delivered vibrotactile stimulation to forehead via one or more forehead application heads 912 which are located at the end of the rear wings of the stimulator.

The application heads 908, 910 and/or 912; of V-ONSor 900 are maintained in close contact with sits of stimulation by weight bearing effect the stimulator body 902 on the nasal bridge and/or the tension of an adjustable elastic band 952 that surround the circumference of the head. Ends 954 of the elastic band 952 are attached to the stimulator at an attachment sits 924, and/or its length and/or tension is adjustable using a metallic adjustment unit 956.

The power source may be any suitable power supply capable of powering one or more functions of the stimulator, such as one or more batteries, capacitors, or the like. As shown in FIG. 9A in some variations a number of illuminated status of light indicators 926 may indicate the charging status of any rechargeable battery.

Figure 10B:
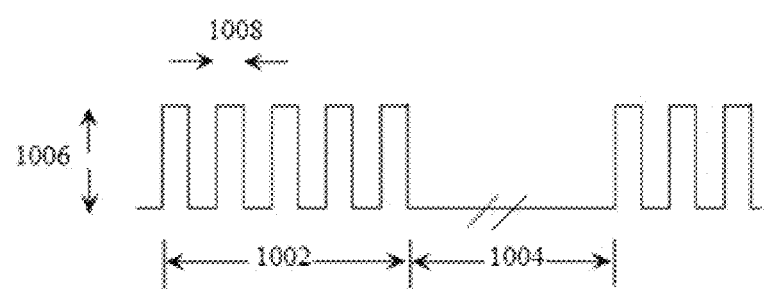
FIG. 10A shows exemplary regular un-modulated waveforms and the features of waveform (amplitude, pulse width, an on time, and off time).
FIG. 10 B shows exemplary shapes of un-modulated waveforms.
FIG. 10C illustrates exemplary amplitude variations over time.
FIG. 10E illustrates exemplary modulations of frequency waveform parameters.
Figure 10B:
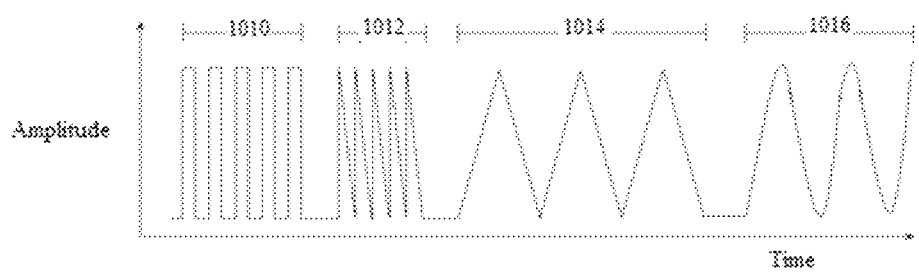

Features of the waveform: FIG. 10A illustrate basic features of square waveform, which include amplitude 1006, pulse width 1008, periods of on time 1002, and/or period of off time 1004. The vibration stimulation waveforms delivered by the stimulators described herein may be having different features and/or specifications. These include the shape, frequency, and/or amplitude, pulse width, with fixed or variable features. The waveform described herein may be having different shapes as shown in FIG. 10B; these include, square wave 1010, the saw tooth wave 1012, the triangular wave 1014, and/or the sine wave 1016.

Modulation of Parameters of waveform: As is described in more detail herein, the employed stimulation waveforms parameters might be fixed or modulated. The shape, frequency, amplitude, and/or the pulse width may be modulated over time. The waveform may be modulated linearly, exponentially at random or in regular basis. Modulation of stimulus parameters is optionally aimed to improve the efficacy of the stimulation and the clinical outcome of ONS and/or to prevent patient habituation to the applied stimulation. In some variations the transition of modulation of the waveform may be gradual such as gradual increase or decrease in the amplitude of stimulus. These increases and/or decreases may have any suitable form, such as linear increases and/or decreases or sinusoidal increases and/or decreases.

Age and/or Duration of Starting Session: The duration of starting sessions in the course of vibrotactile ONS might vary according to the age of the patient. In some instances, it may be desirable to increase the duration of the session per day in older age group of patients compared to children and/or young adults in order to promote the therapeutic effect. The number of mechanoreceptors and/or degree of their sensitivity is decreased by aging.

Duration of Waveform Stimulation: In some instances, the waveform stimulation of V1 described herein may be delivered once or twice daily for few days to few weeks with one day off per week. While in other instances, the waveforms may be delivered once or twice per week. If the treatment course extends to a week or more, the duration of daily sessions might be prolonged progressively. This progressive increment of session duration aimed to overcome patient adaptation that might be produced by mechanoreceptors adaptations.

Figure 10C:
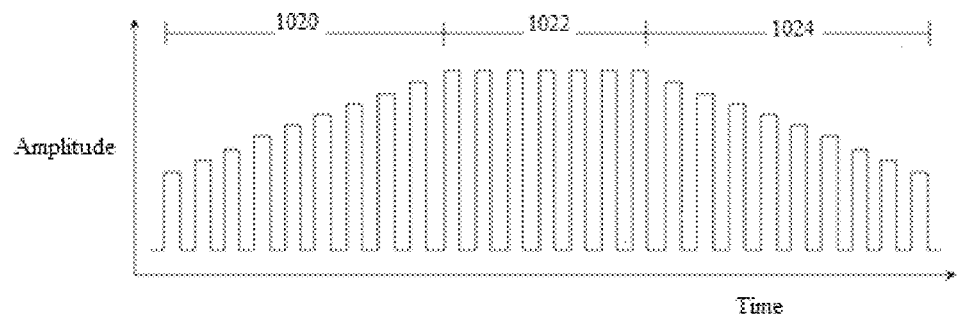

Ramping up and/or ramping down: In some instances, the waveforms described herein may be delivered during the whole session of stimulation without any change in its features as shown in FIG. 10C; 1022. In stimulation bursts may be delivered periodically at regular or irregular intervals. The stimulation amplitude, pulse width, or frequency may be modified during the course of stimulation. For example, the stimulation amplitude may be ramped from low amplitude 1020 to higher amplitude 1022 over a period of time. In other variations, the stimulation amplitude may be ramped from high amplitude 1022 to lower amplitude 1024 over a period of time. The stimulation pulse width 1030 may also be ramped from a low pulse width to a higher pulse width over a period of time as shown in FIG. 10.D. The stimulation pulse width may be ramped from a high pulse width to a lower pulse width over a period of time. The ramp period may be between 5 second and/or 30 seconds. The ramping up or ramping down time might be longer or shorter than this figure.

Frequency: Generally, the frequency is preferably between about 20 Hz and/or about 90 Hz. This frequency is chosen to activate PNS. In some of these variations, the frequency is preferably between about 30 Hz and/or about 60 Hz. In others of these variations, the frequency is preferably between about 50 Hz and/or about 70 Hz. In some variations, the frequency may be about 20 Hz, about 25 Hz, about 30 Hz, about 35 Hz about 40 Hz, about 45 Hz about 50 Hz, about 55 Hz about 60 Hz, about 65 Hz about 70 Hz, about 85 Hz, about 85 Hz, or about 90 Hz. The frequencies described herein may be suitable for stimulating the targeted tissue to initiate a reflex circuit that activates the OBF and/or suitable for directly driving efferent fibers innervating the ophthalmic artery, ciliary and/or choroidal arteries.

Amplitude: The stimulators described herein may be configured to deliver vibration stimulus with suitable amplitude. The sensitivity of mechanoreceptors is decreased by aging. Therefore, the amplitude of vibration stimulus might be higher for older people compared to children. In some variations the amplitude may be between about 1.5 µm and/or about 3.5 µm. In other variations, the amplitude may be variable. For example, the amplitude may vary between about 1.5 µm and/or about 2.0 µm, and 2.5 µm, about 2.5 µm and/or about 3.5 µm. For example, the stimulation amplitude may be ramped from low amplitude 1020 to higher amplitude 1022 over a period of time as shown in FIG. 10.C. In some variations, the amplitude of the pulses may vary according to a sinusoidal profile In some variations in which the amplitude varies over time, the amplitude may vary at a frequency suitable for reducing patient accommodation or increasing patient comfort such as between about 0.1 Hz and/or about 5 Hz, between about 1 Hz and/or about 5 Hz, between about 1 Hz and/or 2 Hz, between about 2 Hz and/or 3 Hz, between about 3 Hz and/or 4 Hz, or about 4 Hz and/or about 5 Hz. Each of these types of amplitude modulation may be implemented alone or in combination with any other type of amplitude modulation, and/or may reduce patient accommodation.

Duty cycle and/or pulse width: A duty cycle is the fraction of one period in which a signal is active. Duty cycle is commonly expressed as a percentage or a ratio. A period is the time it takes for a signal to complete an on-and-off cycle. For ONS protocol, 50% duty cycle is considered. A 50% duty cycle means the signal is on 50% of the time but off 50% of the time. The "on time" for a 50% duty cycle could be a fraction of a second depending on the length of the period.

Figure 10D:
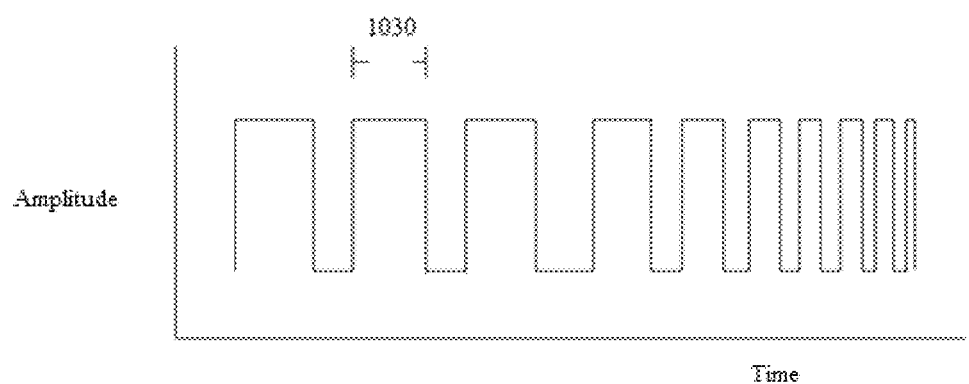
Figure 10E:
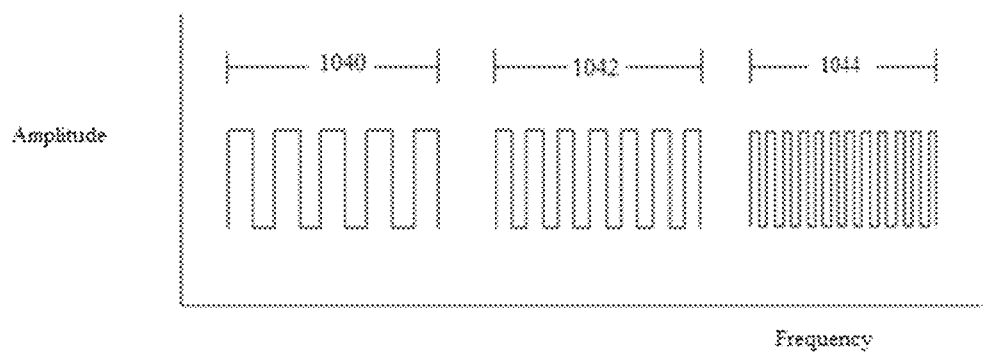

The pulse width duration 1030: the stimulators described herein may be configured to deliver a waveform in which the pulse width lies between 5 ms and/or about 10 ms. The width of stimulus might be used to target specific nerve fibers. Larger-diameter nerve fibers of the trigeminal nerve might be activated by smaller-pulse width, while larger-pulse width might target the smaller nerve fibers (e.g., a-delta fibers, C fibers, sympathetic and/or parasympathetic fibers). In some variations, the pulse width may be constant over time. In other variations, the pulse width may vary over time. Pulse width modulation over time as seen in FIG. 10D may increase the efficacy and/or comfort of the stimulation. In some variations, the pulse width may ramp up from a minimum value to a maximum value, ramp down to the minimum value. In some variations, the pulse width may vary according to a sinusoidal profile.

On/Off Periods: On-time and/or off-time parameters may be used to define an intermittent pattern in which a repeating series of signals is generated for stimulating the V1 during the on-time (such a sequence may be referred to as a "pulse burst"), followed by a period in which no signals are generated and/or the nerve is allowed to recover from the stimulation during the pulse burst. Typically, the ratio off-time/on-time may range from about 0.5 to about 10. Exemplary on/off durations include without limitation, 4 second on/1 second off, 5 seconds on/1 second off, 6 seconds on/1 seconds off, 7 seconds on/1 seconds off.

Exemplary Waveforms: The waveform comprises pulse which may have any suitable frequencies, pulse widths, and/or amplitudes. The stimulation amplitude, pulse width, and/or frequency may be the same from pulse to pulse, or may vary over time. Combinations of these parameters may increase the efficacy and/or comfort of stimulation.

Adjustable Waveform Configuration: In some variations, the treating doctor select the appropriate stimulation waveform and/or these can be configured and/or saved on the device prepared for patient use at home. In variations having such a user interface, the user interface may comprise one or more operating mechanisms, which may allow the user (i.e., the doctor) to control the stimulation waveform prior its use by the patient.

Measurement of OBF

Reduced and/or dysregulated OBF may play an important role in the etiology and/or pathogenesis of various inherited and acquired retinal, choroidal and optic nerve disorders. Thus, qualitative and/or quantitative assessment of OBF is a topic of interest for early disease detection, diagnosis, and/or management. Owing to the rapid improvement in technology, there are several invasive and/or noninvasive techniques available for evaluating OBF, with each of these techniques having their own limitations and/or advantages. Noninvasive techniques include color Doppler imaging (CDI), laser Doppler velocimetry (LDV), laser speckle technique, laser Doppler flowmetry (LDF), retinal vessel analyzer (RVA), retinal oximetry, and/or blue field entopic technique, Fourier domain optical coherence tomography (Doppler FD-OCT) and/or optical coherence tomography-angiography (OCT-A). Invasive techniques include scanning laser ophthalmoscopic angiography with fluorescein and/or indocyanine green (ICG) dye.

OBF Provocation Test

At the beginning of the test, the patient is admitted into a half-light room to have a rest for a time period, for example 15 minutes. Initially, baseline data about various parameters of OBF was measured using CDI and/or OCT angiography, followed by a provocation with ONS via intranasal vibrotactile stimulation for example, approximately 5 minutes on each nostril using standard waveform parameters. The OCT angiography was performed after the 1st round of ONS. A rest period of 30 minutes followed by the second round of ONS, and/or final OCT angiography were performed followed by CDI. OBF response to ONS was calculated. It was represented as an average increase in the OBF in response to the ONS during the two measurement cycles of OCT angio and/or was defined as the percent increase relative to the baseline data. Regarding CDI, the pre-ONS data is compared to post-ONS data. In some embodiments, CDI examinations are performed by an experienced sonographer at the two time points. Each patient was placed in a supine position, and/or the probe was applied to the closed eyelid using sterile coupling gel. The different parameters of OBF in ophthalmic artery CRA, and/or PCA were measured with CDI. When compared to normal age and sex adjusted controls. OBF provocative test is of great value to define the degree of impairment of OBF, and/or to quantify the response after provocation by ONS. The latter might be used as an indicator for therapeutic response to ONS.

Patient-Optimized Waveforms

The method may comprise measuring OBF prior any ONS to determine the degree of impairment of OBF of the said subject compared to normal population, and/or to consider these values of OBF as a baseline data. To measure the effect of different pre-determined sets of waveform parameters such as frequency, amplitude, pulse width, on/off period, or the temporal modulation of these parameters, the OBF is measured again after receiving ONS. Accordingly, the set of parameters that produce the optimal increment of OBF are clarified. It should be appreciated that a similar method may be used to identify one or more patient-optimized waveforms stimulation in different sits of stimulation (intranasal, nasal bridge or forehead region) once a patient-optimized waveform or waveforms are identified, a stimulator may be configured to deliver the waveform(s).

Selective waveform for different stages of the disease: The vibration stimulation waveforms delivered by the stimulators described herein may be tailored for specific treatment regimens according to the staging of the disease and/or specific type ocular disorders. In variations of stimulators configured to deliver vibration, different waveforms may be delivered via stimulator, and/or the delivered waveform may be changed over time. The suitable waveform is defined according to the clinical outcome of these signals.

The application of mechanical stimulation of LMHFV on peri-orbital cranial bone has dual effects on recruitment and proliferation of endogenous bone marrow stem cells EBMSCs. The first effect is mediated by SP expression via ONS, while the second is produced by the direct mechanical stimulation of LMHFV on cranial BMSCs. SP has been identified as a potent injury-inducible messenger that mobilizes ESCs from the bone marrow to the circulation to accelerate tissue repair. It also promotes the migration and differentiation of vascular endothelial cells. SP was found to be as potent as Granulocyte colony-stimulating factor (G-CSF), the primary growth factor responsible for the proliferation and differentiation of bone marrow granulocyte progenitors into mature granulocytes. The efficacy of SP was found identical to that of MSCs transplanted into the vitreous. Additionally, SP improves MSC-mediated RPE regeneration by modulating PDGF-BB. On the other hand, the application of LMHV on peri-orbital cranial bone might initiate ESCs recruitment via expression of SDF1. Expression of SP and SDF-1 in peripheral blood and target tissue on response to application of MHFV is anticipated to be involved in mobilization and recruitment of EMSCs to the diseased retina and/or optic nerve in a similar fashion to that of injured cornea and fractured bone. Interestingly, the human cranial BMSCs have greater tendency to differentiate into neuron-like cells than standard BMSC obtained from iliac crest.

Chemical Ophthalmic Nerve Stimulator

Chemical Ophthalmic Nerve Stimulator-Single Mode, Hand Held Device 1000 (Ch-ONSor 1100): The present invention, in some embodiments thereof, is based on the interesting finding that a TRPM8 agonist can stimulate the V1 and/or further that the same TRPM8 agonist can improve visual function of the retina via a reflex induced increased OBF possibly by parasympathetic activation in a way similar to cold reflex.

The TRPM8 channel is a nonselective cation channel found on lightly myelinated and/or unmyelinated A-delta and/or C primary afferent neurons. They are expressed in trigeminal neurons and/or dorsal root ganglion (DRG) neurons. TRPM8 channels are activated by moderate cold (15-30° C.) and/or by cooling compounds, such as menthol and/or icilin. A low concentration of menthol increased the activity of cool cells, whereas a high concentration caused these neurons to inactivate after a brief period of activity.

Nasal vestibule is a strong reflexogenic and/or preferable site for vibrochemical ONS as this location has the following features; a) easy accessibility b) Increased vibro-chemical sensitivity of mucosa of nasal cavity as indicated by an electrophysiological study, whereas anterior third of nasal septum reacts more to chemical compared to mechanical stimulation of V1. c) Menthol sensitizes peripheral afferents and/or trigeminal neurons to cold stimulation and/or mechanical stimulation. d) Characterization and/or cloning of trigeminal sensory neurons revealed that 55% of these neurons activated by menthol and/or cold. Accordingly, the invention, in some embodiments thereof, as described herein provides methods of treating, preventing or halting progression retinal, choroidal and optic nerve disorders in a subject comprising administering to the nasal mucosa of the vestibule of the subject a composition comprising a pharmaceutically acceptable carrier and/or a pharmaceutically effective amount of a TRPM8 agonist such as of menthol.

Figure 11:
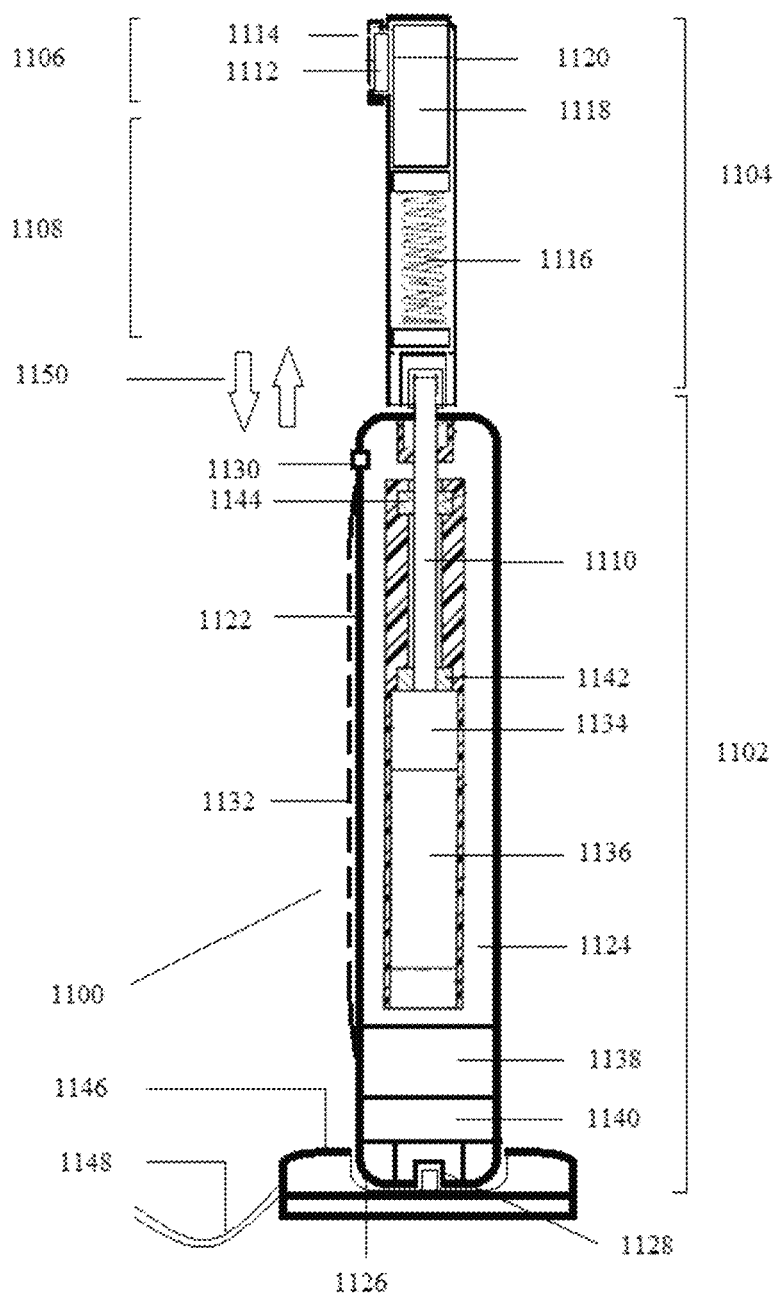
FIG. 11 depicts an exemplary handheld chemical stimulator Ch-ONSor 1100

FIG. 11 illustrates a Ch-ONSor 1100 according to one implementation of the invention. The Ch-ONSor 1100 can be used to provide chemical stimulation to the nasal septal mucosa of the vestibule (AEN) in a pulsatile controlled fashion.

The Ch-ONSor 1100 may comprise a stimulator body 1102 and/or a stimulator probe 1104, where the stimulator probe ended with intranasal application head 1106. Generally, the chemical stimulator is configured to generate a chemical stimulus that may be delivered to the subject. The chemical stimulator probe designed to accommodate a micro pump 1112 for injection of chemical agent to septal mucosa of nose of a subject.

Figures 12A, 12B:
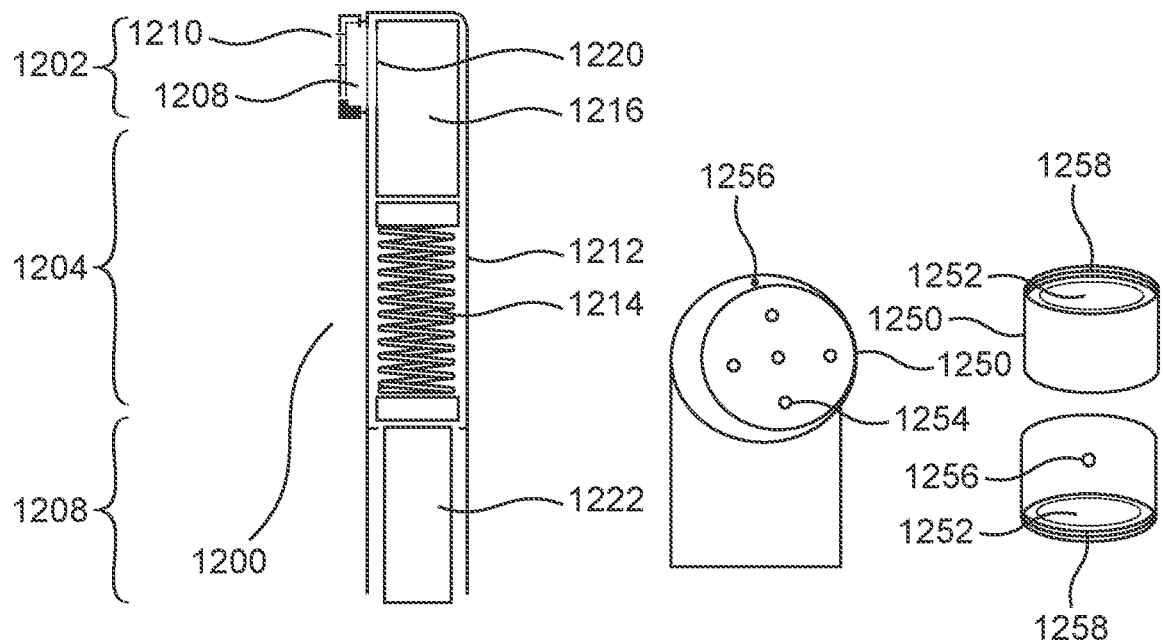
FIG. 12 A-B illustrates an exemplary construction of the chemical stimulator probe 1200

FIGS. 12A and B illustrate stimulator probe 1200 of Ch ONSor 1100. The stimulator probe 1200 comprised detachable, disposable application head 1202, a stainless-steel syringe 1204 with spring like plunger, and/or the shaft of vibrating system 1206. The application head 1202 is cylindrical in shape and/or made of rigid plastic material. It contains a compressible elastic reservoir 1208 with irrigation holes 1210 for releasing its content during the activation of the system. The stainless-steel syringe 1204 is composed of a barrel 1212, which contains spring like plunger 1214 and/or pressure transmitting elastic bag 1216. The plunger and/or pressure transmitting elastic bag are maintained in place by an annular diaphragm 1218, through which the vibrating head 1222 moves up and/or down pushing the spring like plunger forward.

The pressure transmitting bag 1216 is separated from the reservoir by a thin elastic membrane 1220. As this elastic membrane is located between the reservoir 1208 and/or the pressure transmitting bag 1216, its function is to transmit the pressure pulsation from the vibrating head 1222 to the reservoir 1208 in order to release fluids from the irrigation holes 1210 in a pulsatile controlled fashion. Whenever the pressure inside the reservoir is decreased, the elastic membrane 1220 moves toward and/or bulge into the reservoir 1208 to compensate for decreased pressure induced by release of fluid from the reservoir 1208 through the irrigation holes 1210. In this embodiment, the function of the syringe with spring like plunger is to maintain optimal pressure inside the pressure transmitting bag as well as the reservoir after each pulsation.

FIG. 12B illustrates the features of the application head. It is composed of a plastic cylinder 1250 that can be connected to the stimulator probe by means of screw like mechanism 1258 or any other suitable mechanism. It contains a reservoir 1252 filled with chemical stimulant (TRPM 8 agonist) like menthol. On its external face, the application head has a number of irrigation holes 1254, through which reservoir 1252 content is released by pulsatile pressure of the vibrating system.

The stimulator body 1102 may comprise a housing 1122 and/or a defined a body cavity 1124, and/or base 1126. The body cavity 1124 may contain a control subsystem 1136 and/or a vibration power source 1134, and/or the user interface 1132 which together may generate and/or mechanically control the chemical stimulus. The power source may be any suitable power supply capable of powering one or more functions of the stimulator, such as one or more batteries, capacitors, or the like.

The stimulus may be delivered to a subject via the head 1202 of the stimulator probe 1200 which may be configured to be easily inserted into the nasal cavity and/or come in contact with the mucus membrane of nasal septum of a subject, FIGS. 12A and/or B. Stimulator probes are optionally detachable, sterile and/or disposable. The stimulator body 1102 and/or stimulator probe 1104 may be reversibly attachable.

The reservoir 1208 of the micro pump is located in the application head of stimulating probe. The reservoir is filled through an injection port 1256 at the superior end of the head, and/or its contents are released under pulsatile pressure through one or more irrigation holes 1254. In some embodiment, the reservoir 1252 is preloaded with chemical stimulant (TRPM 8 agonist) in the form of soft jell or thick fluid containing TRPM8 agonist such as menthol. A filling kit composed of a syringe preloaded with enough amount of sterile chemical stimulant is used to fill the reservoir of the micro pump through a specially designed cannula. It is appreciated that during filling of reservoir with stimulant solution, the irrigation holes 1254 are facing upward while the syringe is inserted into the injection port via a special cannula at a horizontal plan. Whenever the reservoir is fully filled, and/or the pressure reaches an appropriate level, the fluid will start to leave the reservoir through the irrigation holes. The irrigation holes 1254 are provided with one-way micro valve that let fluid out under pressure but prevented air to come into the reservoir. A similar one-way micro valve is present in the injection port 1256 to prevent outside leak of reservoir content.

On activating the Ch-ONSor 1100, the vertical movement 1150 produced by the head 1110 of vibration producing system will be coupled to the spring like plunger 1116 to transmit this pulsation through the pressure transmitting bag 1118 and/or finally to the reservoir 1112 of micro pump in order to release micro droplets of chemical stimulant from irrigation holes 1114 in a pulsatile way. The released contents will be in the form of very small droplets chemical stimulant for activation of the septal branch of AEN.

The stimulator body 1102 may comprise a user interface 1132 comprising one or more operating mechanisms to adjust one or more parameters of the chemical stimulus. The on/off switch can be connected to an internal controller 1136 located within the handle. The internal controller 1136 can be electrically coupled to the vibrating system 1134 to actuate the release of chemical stimulant by a mechanical movement of the head of vibrating system 1110.

Vibro-Chemical Stimulator (V-Ch-ONSor 1300)

V-Ch ONSor 1300 is bi-modular device in which vibrotactile stimulation, and/or chemical stimulation can be provided through the same stimulator probe 1300 using a common user interface in a hand-held device. Providing two actions on a single system makes it easier for an operator for delivering specific dose of chemical stimulation and/or vibrotactile stimulation simultaneously or in a succession.

Figures 13A, 13B:
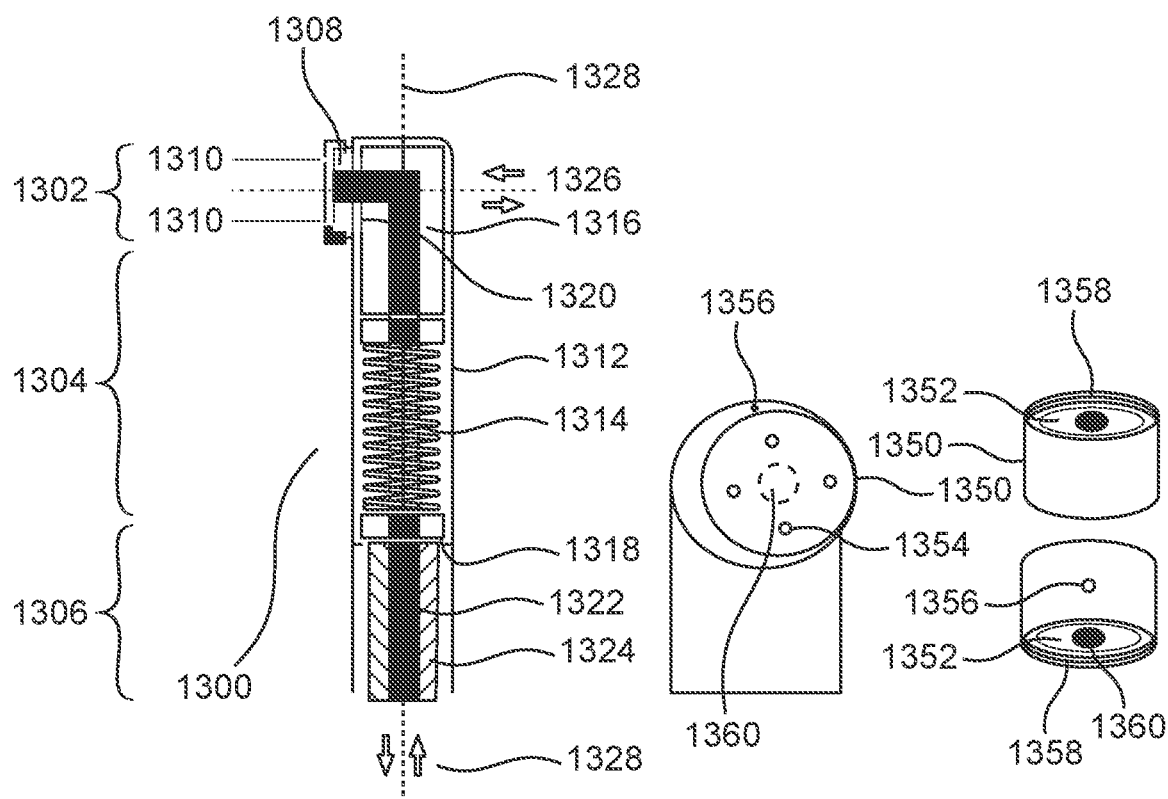
FIG. 13 A-B illustrates an exemplary construction of the vibro-chemical stimulator probe 1300 with disposable chemical micro pump FIG. 14 A-B Depicts an exemplary handheld ultrasonic ONSor (U-ONSor 1400) and its probe

FIGS. 13A and/or 13B demonstrated the basic structure of V-Ch ONSor probe 1300. The micro pump is basically and/or functionally is the same as that had been described previously in a single mode Ch-ONSor 1100. However, some modifications have been made to allocate the chemical pump and/or the vibrotactile probe in the same stimulating head.

In this embodiment, the V-Ch ONSor 1300 is configured to generate vibrotactile stimulation and/or to accommodate a micro pump for pulsatile injection of chemical agent to stimulate septal mucosa of nose of a subject. As shown in FIGS. 13A, 13B, the V-Ch ONSor 1300 probe is basically composed of a modified micro pump traversed at its center by a vibrating shaft 1322. The micro pump comprised an annular reservoir 1308, a pressure transmitting elastic bag of an inverted L shaped annular cylinder 1316, and/or an annular spring like plunger adapting at its center the shaft 1322 of the vibrating probe. The reservoir 1308 and/or pressure transmitting bag 1316 toke an annular shape or the shape of a hollow cylinder surrounding a centrally located vibrating shaft 1322. The irrigation holes 1310 located at the periphery of the application head. The pressure transmitting bag 1316 is separated from the reservoir 1308 by a thin annular shaped elastic membrane 1320. As this elastic membrane is located between the reservoir 1308 and/or the pressure transmitting bag 1316, its function is to transmit the pressure pulsation from the vibrating head 1324 to the reservoir 1308 in order to release fluids containing chemical stimulant through the irrigation holes 1310 in a pulsatile controlled fashion. Whenever the pressure inside the reservoir 1308 is decreased, the annular elastic membrane 1320 moves toward and/or bulge into the reservoir 1308 to compensate for decreased pressure induced by released fluid through the irrigation holes 1310. In this embodiment, the function of the spring like plunger 1314 is to maintain the optimal pressure inside the reservoir 1308 and/or to compensate for pressure loss caused by release of fluid through irrigation holes 1310 after each pulsation.

The stimulator body may comprise a housing and/or a defined a body cavity, and/or base. The body cavity may contain a control subsystem, the user interface and/or two vibration power sources, one for production of vibrotactile stimulation through the shaft 1322, and/or the other 1324 for mechanical pulsatile injection of chemical stimulant. The generated vibrotactile stimulation oscillates along the axis 1326 in order to produce mechanical stimulation of the AEN supplying the nasal septal mucosa of the vestibule. The power source may be any suitable power supply capable of powering one or more functions of the stimulator, such as one or more batteries, capacitors, or the like.

On activating the chemical module of V-Ch-ONSor 1300 the spring like plunger is pushed forward by a cylindrical vibrating shaft 1324 produced by the second vibration producing system. The vibration is transmitted via the pressure transmitting bag 1316, pressurizing the reservoir 1308 to release its content through the irrigation holes 1310 in a pulsating way. The released contents will be in the form of very small droplets of chemical stimulant for activation of the septal branch of AEN.

In instances where the stimulators described here are bi-modular such as vibro-chemical ONSor 1300, the user interface may comprise one or more operating mechanisms, which may allow the user to control the function of both stimulators such as the sequence of stimulation (simultaneous or sequential). For example, the micro pump is delivering the chemical agent in a pulsatile way with a frequency ranging from 0.5 Hz to 2 Hz, and/or 2 second on/13 second off. Programming of vibrotactile and/or chemical stimulation might be in the form of initial 2 second of chemical stimulation followed by 11 second of vibrotactile stimulation, followed by 2 second off for both chemical stimulation and/or vibrotactile stimulation. This pattern can be repeated over the session of treatment.

Hand Held Ultrasonic Ophthalmic Nerve Stimulator 1400 (US-ONSor 1400)

In some embodiments, US-ONSor 1400 relates to pulsed Low Intensity Low Frequency Ultrasound (LILFU) nerve stimulation systems. Generally, the systems are hand held devices with intranasal application head.

LILFU stimulates peripheral neurons by two mechanisms. The first is thermal; where pulsed ultrasound enhances neural activity by increasing temperature of targeted nerve fibers up to 42 degrees C. for short time periods. In the second mechanism is mechanical. LILFU stimulates neuronal activity at least partially by triggering voltage-gated $Na^+$ transients and/or voltage-dependent $Ca^{2+}$ transients, which resulted in the generation of action potentials of the targeted neuron. Additionally, the LILFU induced changes in neuronal activity were sufficient to trigger synaptic vesicle exocytosis and/or synaptic transmission at central synapses thereby driving network activity.

LILFU is typically in the range of 0.3 MHz to 8 MHz or above. A rate of 300 Hz (or lower) causes inhibition (down-regulation). A rate in the range of 500 Hz to 5 MHz causes excitation (up-regulation). Power is generally applied at a level less than 60 $mW/cm^2$. US pulses may be monophasic or biphasic, the choice made based on the specific patient and/or condition. The US transducer is pulsed, typically tone burst durations of (but not limited to) 25 to 500 μsec.

Figure 14A:
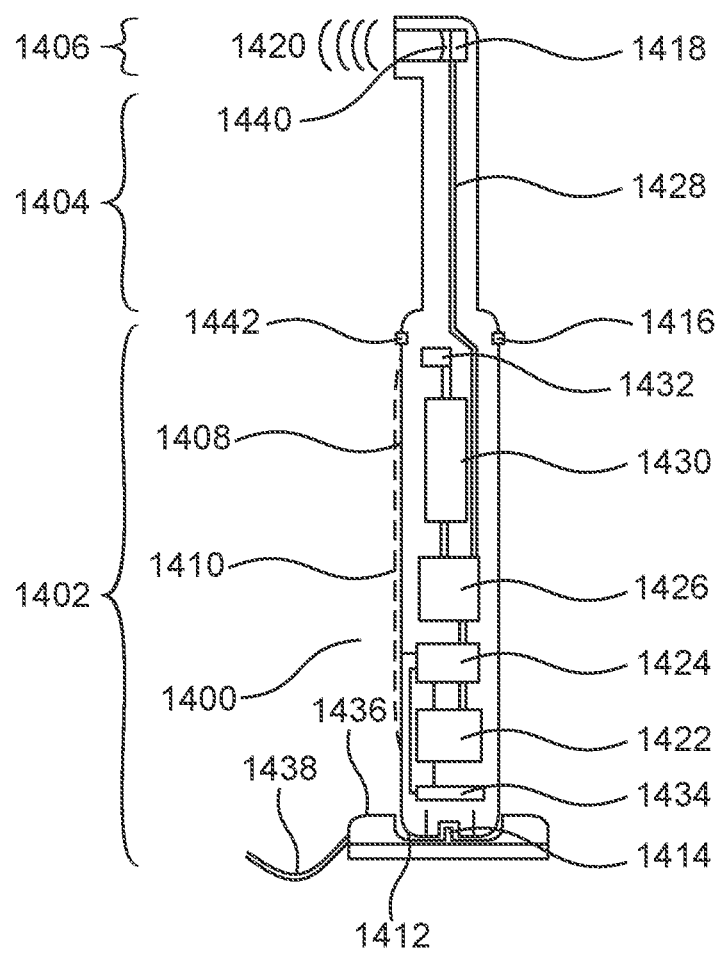

US-ONSor system 1400 in the preferred configuration is shown in FIG. 14. A US-ONSor 1400 comprises of a body of the stimulator 1402, a neck 1404, and/or a head portion 1406 constructed of a rigid plastic material such as Acrylonitrile Butadiene Styrene (ABS). In some variations, the US stimulator probe 1400 may comprise one application head, which is small rounded that enable the user to introduce it easily in the nasal vestibule. The stimulator body 1402 may have a flat base proximal end 1412 with a circular small tunnel 1414 for energy connection and/or a tapered proximal end that gives attachment to the shaft 1404 of the stimulator. The front housing, back housing, and/or side housing might constitute a continuous shell of a tetragonal cylinder, with one rectangular opening at front housing where the user interface 1410 can be adapted. The front housing may also comprise an opening configured to receive a number of small lights 1416 (4 lights) that give an indication of status of battery. In some instances, it may be desirable for the stimulator body to be sealed, such that it may be waterproof or the like.

The selection of the ABS material for the U-ONSor stimulator body 1402, shaft 1404 and/or application head portion 1406 is made due to the excellent acoustic characteristic of ABS, and/or its ability to encapsulate the ultrasound transducer 1418. To increase the efficiency of the ultrasound transducer 1418, closed cell foam filler might be utilized at the back surface of the ultrasound transducer 1418 to redirect the radiation of ultrasonic pressure waves 1420 from the back surface of the ultrasound transducer 1418 toward the application head 1406 surface, thereby significantly increasing the output of the ultrasound transducer 1418 toward the targeted nerve to be stimulated.

The US-ONSor stimulator body 1402 also contains a drive motor 1430 and/or an electronic control module 1424. The output shaft of the drive motor 1430 typically carries an off-center weight 1432. The shaft of the drive motor 1430 and/or the off-center weight 1432 attached to it rotate at least at different frequencies. For example it might rotate at approximately 30,000 rpm, creating a 500 Hertz ultrasonic frequency vibration in the application head 1406. In some variations, the stimulator probe may comprise one intranasal head 1406, which may be configured to be easily inserted into the nasal cavity and/or come in touch with the nasal septum of the nasal vestibule of a subject or patient. The application head 1406 is designed with a weight distribution plan wherein the head portion 1406 is significantly lighter weight than the loaded weight of the stimulator body 1402. The neck portion 1404 is designed to be lightweight and/or flexible, to act as a motion transducer. The weight of the stimulator body 1402 and/or the user's hand dampens the vibration amplitude of the stimulator body 1402, while the flexing neck portion 1404 causes the head portion 1406 to vibrate.

Figure 14B:
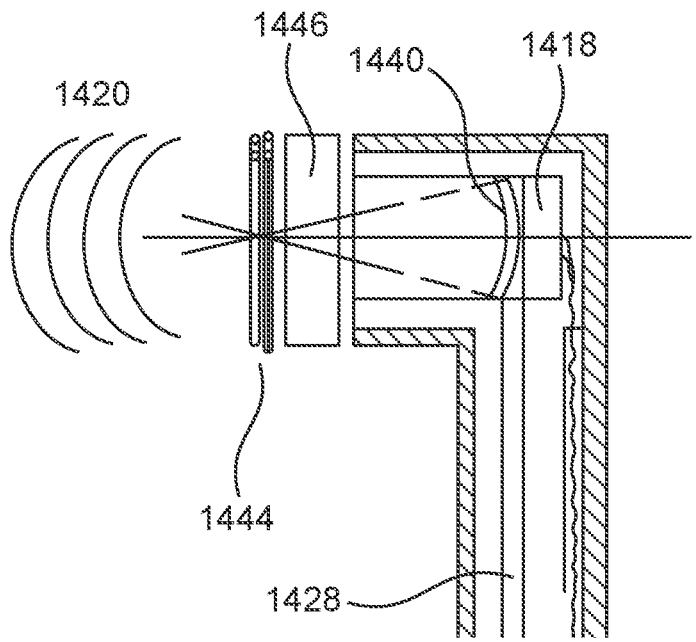

The ultrasound transducer 1418 is typically a PZT-8 piezoelectric ceramic or similar material. FIG. 14B illustrates a side view of US transducer 1418, US-conduction-medium insert 1446 with US field focused on the target nerve bundle 1444. Depending on the focal length of the US field, the length of the US transducer assembly can be increased with a corresponding increase in the length of ultrasound-conduction-medium insert 1446. The focus of US transducer 1418 can be purely adjusted through the physical configuration of its transducer array 1440 (e.g., the radius of the array) or by focus or change of focus by control of phase and/or intensity relationships among the array elements. In an alternative embodiment, the focus is provided by a lens that is bonded to or not-permanently affixed to the transducer. Even though the target for example AEN, is relatively superficial; the transducer can be moved back in the holder to allow a longer focal length. Ultrasound conduction medium will be required to fill the space. Examples of sound-conduction media are Dermasol from California Medical Innovations or silicone oil in a containment pouch.

Upon activating the hand held US-ONSor 1400 by the control switch 1442, the low voltage DC energy supplied by the battery pack 1422 is converted into an ultrasonic frequency DC current by the electronic frequency generator module 1426, which is connected to the ultrasound transducer 1418 by the connecting wiring 1428. Under the influence of the ultrasonic frequency DC current the ultrasound transducer 1418 resonates, expands and/or contracts volumetrically, in tune with the frequency supplied by the electronic frequency generator module 1426 and/or thereby converts the electronic energy into ultrasonic pressure waves 1420. These non-attenuated ultrasonic pressure waves 1420 are impacting nasal septal mucosa and/or stimulate septal branch of AEN.

The time averaged intensity of the ultrasonic pressure waves 1420 is ideally limited to approximately 30 mW/cm$^2$, which is effective for the purpose of nerve stimulation and/or at the same time it is below the tissue heating range. However, higher intensities can be applied with the appropriate safeguards against tissue heating or damage. The ultrasonic pressure waves 1420 could be applied in a pulsed burse mode modality such as 200-microsecond burse width repeated at 1 kilohertz repetition rate to further limit tissue heating. Depending on the final acoustic energy output of the ultrasound transducer, various burse widths and/or repetition rates are possible to assure that no tissue damage occurring. The ideal frequency of the ultrasonic pressure waves 1420 is between 0.44 MHz and/or 0.67 MHz.

The illustrated section of the neck portion 1404 is shown in FIGS. 14 A and/or 14.B explains the motion transducer function of the neck portion 1404. The vibration created by the off-center weight 1432 and/or the motor 1430 in the stimulator body 1402 is a circular vibration. A motion transducer by definition converts one form of vibration into another form of vibration.

The electronic control module 1424 controls the rotation speed of the drive motor 1430. The control switch is a part of user interface 1410 provides on-off signals to the control module 1424 to start the sonic frequency motion of the head portion and/or the application head 1406. The user interface 1410 is also used to send programming impulses to the control module 1424 to create higher or lower ultrasonic frequency vibrations of the head portion 1406 by changing the rotational speeds of the drive motor 1430. The power source may be any suitable power supply capable of powering one or more functions of the stimulator, such as one or more batteries, capacitors, or the like.

Features of the waveform: The US vibration stimulation waveforms delivered by the stimulators described herein may be having different features and/or specifications. These include the shape, frequency, and/or US power, pulse width, with fixed or variable features.

Modulation of Parameters of waveform: As is described in more detail herein, the employed stimulation waveforms parameters might be fixed or modulated. The frequency, US power, and/or the pulse width may be modulated over time. The waveform may be modulated linearly, exponentially at random or regular basis. It should be understood that modulation of stimulus parameters is aimed to improve the efficacy of the stimulation, improve the clinical outcome of ONS and/or to prevent patient habituation to the applied stimulation (i.e., may help to prevent mechanoreceptor adaptation to vibration stimulation)

Frequency: Generally, the frequency is preferably between about 500 Hz and/or about 8 MHz. In some of these variations, the frequency is preferably between about 500 Hz and/or about 1 MHz In others of these variations, the frequency is preferably between about 500 Hz and/or about 2M Hz. In some variations, the frequency may be about 500 Hz, about 600 Hz, about 700 Hz, about 800 Hz, about 900 Hz, about 1 MHz about 1.2 MHz, about 1.4 MHz about 1.6M.

US power: US power is generally applied at a level less than 60 mW/cm$^2$. In some variations the US power may be between about 30 mW/cm$^2$ and/or about 60 mW/cm$^2$. In other variations, the power of US power may be variable. For example, the power may vary between about 30 mW/cm$^2$ and/or about 40 mW/cm$^2$ and/or about 40 mW/cm$^2$ and/or about 50 mW/cm$^2$, about 50 mW/cm$^2$ and/or about 60 mW/cm$^2$. For example, the US stimulation power may be ramped from low power to higher power over a period of time.

Programming of the device: Certain parameters of the US stimuli generated by the U-ONSor 1400 are programmable. Programming the neurostimulator may be performed in a variety of manners, including those known to persons skilled in the art having benefit of the present disclosure.

Saved Waveform Settings:

Some variations of the stimulators described herein may be configured with a number of stimulation waveforms. In some variations, a preferred set of waveforms is selected according to the age of patient, staging of the disease, and/or the history of nasal trauma or surgery. In some variations, a preferred set of waveforms to be saved on a stimulator may be preselected according to results of waveform optimization method. In some variations, random selection of a different waveform each time is employed to decrease the risk of patient's adaptation to any of waveform of particular stimulation pattern. In some variations, the treating doctor select the appropriate stimulation waveform and/or these can be configured and/or saved on the device prepared for patient use at home.

Optical ONSor Systems (Op-ONSor 1500)

This invention, in some embodiments thereof, relates to pulsed optical nerve stimulation systems to V1. The site of stimulation may include; nasal cavity mucosa supplied by AEN. Generally, the systems are portable devices and/or may have portable case, and intranasal stimulating heads. The invention, in some embodiments thereof, relates to a method for increasing OBF to the retina and/or choroid and optic nerve head in subject's dysregulated and/or reduced OBF.

Optical neural stimulation is emerging as an exciting and/or more advantageous alternative to traditional electrical stimulation. The method relies on direct but transient (non-contact, pulsed) irradiation of the nerve surface by using a light source such as lead or laser. The response to optic stimulation is spatially precise, permitting selective targeting of individual nerve fascicles with no observed tissue damage. Genetic modification of neurons to express opsins, i.e. light-sensitive proteins on neuronal membranes, renders neurons sensitive to light of a specific wavelength with millisecond precision.

Transdermal melanopsin-mediated optical stimulation of V1 is a non-invasive alternative approach of optical stimulation of peripheral sensory neurons. It relies on stimulation of subset of neurons of V1 naturally expressing melanopsin and the use of blue light as a source for stimulating these neurons. This technique depends on the concentration of melanopsin in the targeted tissue and/or the optical properties of the intermediate tissues e.g. skin and/or subcutaneous tissue. Melanopsin is a type of photopigment belonging to a larger family of light-sensitive retinal proteins called opsins and/or encoded by the gene Opn4. Melanopsin photoreceptors are sensitive to a range of wavelengths and/or reach peak light absorption at blue light wavelengths around 480 nanometers. In human, TG neurons expressing melanopsin range from 14 to 46 μm, classifying them as C fiber or Aδ fiber neurons. The said melanopsin-expressing neurons also likely express receptors for other sensory stimuli, for example, TRPM8 for temperature and/or evaporation in small (10-30 μm) C fibers or piezo2 for pressure in medium-sized (30-50 µm) Aδ fibers have demonstrated a decrease in corneal mechanical sensitivity in OPN4$^{dta/dta}$ mice, consistent with ablation of melanopsin-expressing mechanoreceptive Aδ fibers. Coincident blue light stimulation of melanopsin-expressing neurons that express also TRPM8 may lead to enhanced SP and CGRP expression and activation of TVS and/or TABRs and/or may decrease the threshold of stimuli for either light, cold stimuli and mechanical stimuli.

Intranasal cavity is a self-contained cavity and/or was chosen for optical stimulation for a number of reasons, these include; the near location of branches of V1 to the surface of nasal mucosa, the relatively thin keratin layer. Additionally, nasal vestibule is richly supplied with unmyelinated C fiber or Aδ fiber neurons of V1 that express melanopsin.

Portable Optical ONSor System 1500

Figure 15:
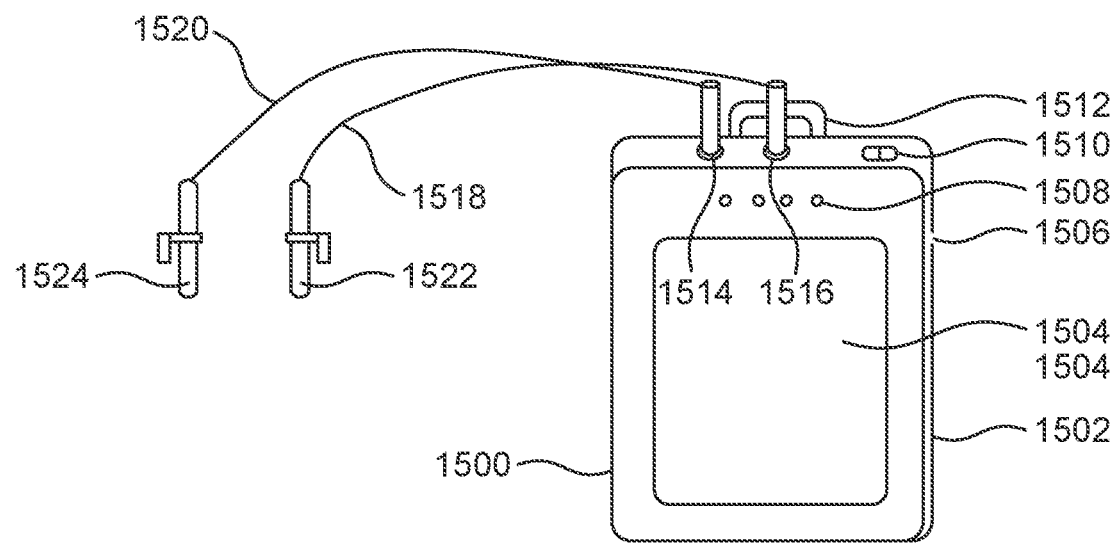
FIG. 15 depicts an exemplary of portable optical ONSor (O-ONSor 1500)

FIG. 15 illustrates one particularly preferred embodiment of the present invention wherein the Op-ONSor 1500 consists of a portable control unit 1500. In this particular embodiment the case or housing 1502 is equipped with a clip 1512 that allows the unit to be worn on the shirt pocket or belt or the like during use. The other side of the case relative to the belt clip is equipped with a display 1504 (user interface) which may be a touch screen that allows the user to adjust different parameters of the optical stimulus such as the frequency, energy, intensity, type of light emitted by the light source, irradiance (25-50 mW/mm$^2$), Pulse width (10 ms), shape of waveform and/or modulating these parameters or select preset features of the stimulus. In some variations the system 1500, delivers pulsed blue light. In other variation the system 1500 delivers pulsed NIR light. The Control unit 1500 of the system communicates with the light delivery device 1522, 1524 via power coupling 1518, 1520. In one embodiment, the stimulating tube is designed to have round shaped tip that can be inserted easily in the nasal cavity.

The top face of the case 1502 is further provided with an on/off switch 1510 and/or a two-power coupling 1518, 1520 connecting the light delivery device and/or the control unit by two power outlets 1414, 1516. During administration of optical ONS, typically stimulating tubes 1522, 1524 are inserted into both nasal vestibules and/or held in place via nasal clips.

Figure 16:
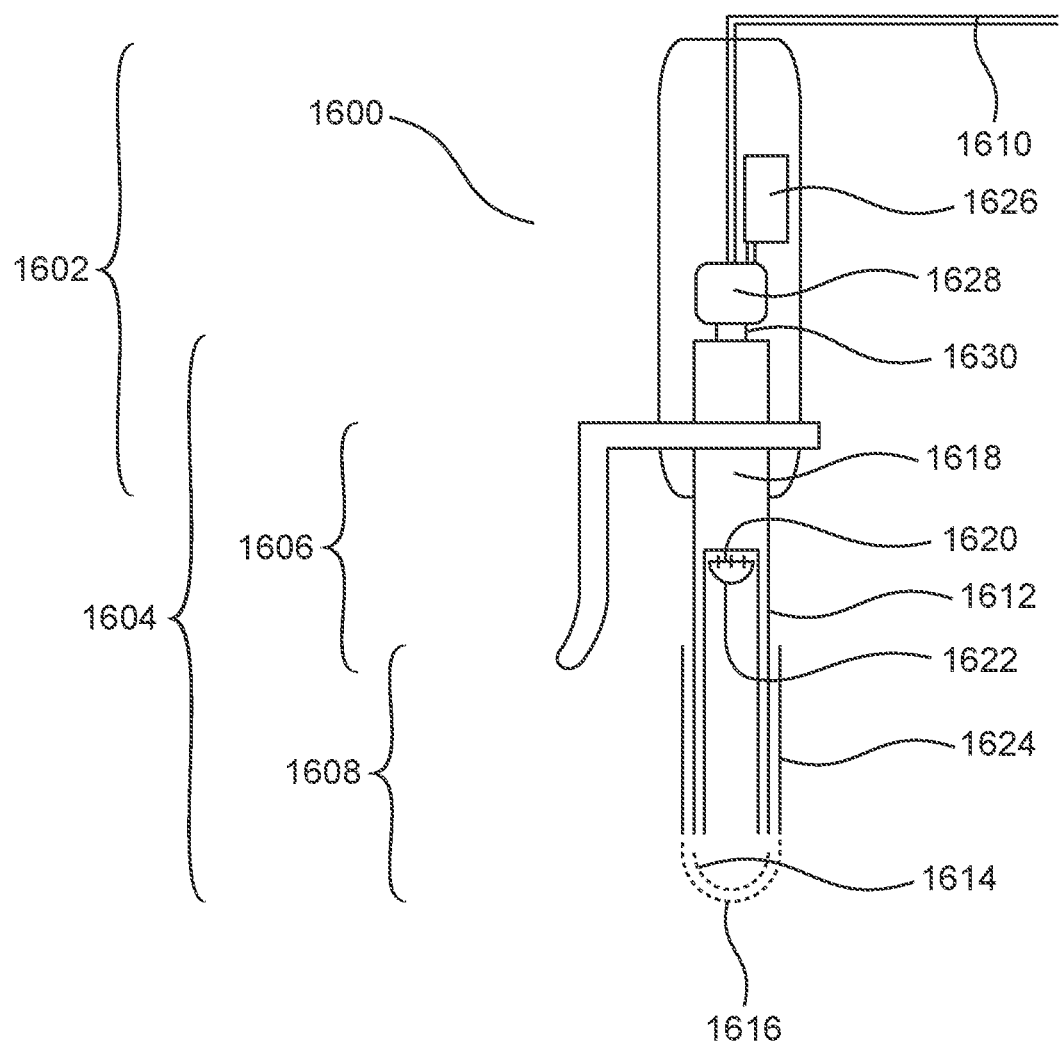
FIG. 16 depicts an exemplary of an exemplary construction of the optical stimulator tube 1600 with disposable sleeve.

As shown in FIG. 16, the light delivery device 1600 comprises a stimulating tube 1604 for providing optical stimulation to the nasal cavity in accordance with one embodiment of the present invention. The light delivery device 1600 in this embodiment generally includes a housing 1602 and/or a light source 1618 positioned in or near the housing. The distal end of the stimulating tube 1604 is configured to be inserted into the nasal cavity to stimulate V1 by administration of pulsed blue or NIR light to the nasal cavity. The frequency of pulsed blue or NIR light might be 10 Hz, 15 Hz, 20 Hz, 25 Hz, 30 Hz, 35 Hz, 40 Hz, 45 Hz, 50 Hz, 55 Hz, 60 Hz. or more.

In some embodiments, the housing of the light delivery device in combination with the light source 1618 are configured to be held in place by nasal clip 1606 for an extended period of time (therapeutic time) without undue effort or discomfort, due to the lightweight, portable design of the device.

In one embodiment, the stimulating tube 1604 comprised of proximal opaque part 1612 and/or distal transparent part 1614. As will be appreciated, optically transparent distal part 1614 comprised of components or materials that are transparent to blue light, (wavelengths between about 400 nm and/or about 500 nm) and/or NIRL (680-830 nm). In some cases, optically transparent part 1614 can refer to more narrow ranges of transparency. For example, optically transparent to blue light can refer to transparency in the range from about 455 nm to 505 nm; more specifically to 480 nm A sleeve 1608 may be provided to at least partially cover the stimulating tube 1604. In one embodiment, the sleeve 1608 is disposable and/or in another embodiment, the sleeve is not disposable. Non-disposable sleeve is sterilizable.

The stimulating tube 1604 is covered by a disposable or re-usable sleeve 1608. The sleeve is made of materials such as aluminum or a plastic coated with aluminum. In this embodiment, the inner material will transmit light with limited or not absorbing the light. These configurations generally allow optical energy, or light, generated by the light source 1618 to travel through the stimulating tube 1604 and/or exit both the tip 1614 of the tube 1614 and/or the tip of the sleeve 1616. At the distal end of the sleeve, there is a transparent window 1616 for the exit of light. The shape of the window defines the targeted area of the nasal cavity to be stimulated by blue light and/or NIR light. In some embodiment the window might be cylindrical in shape and/or include all the distal part of the sleeve. In another embodiment the window takes the shape of an incomplete cylinder with an opaque wall adjacent to the lateral wall of the vestibule. In another embodiment the window represented as a half of cylinder of transparent window facing the nasal septum. The covering sleeve can further control the illumination pattern by using different types of sleeves having different aperture sizes or pattern of the tip. In such embodiments, light energy is emitted from the stimulating tube 1604 to activate V1 within the nasal cavity of the patient.

The proximal end 1612 of the stimulating tube 1604 is coupled to the distal end of the housing 1602 by any of a variety of couplings such as a press-fit connection, a screw, or any other suitable coupling that ensure optimal mechanical, optical, and/or electrical couplings. In some variations, the stimulating tube 1604 may be permanently attached to the housing 1602.

In one embodiment, the housing 1602 of the body includes a light source 1618. Suitable lighting technologies, including, a bulb, an emitter, a light emitting diode (LED), a xenon lamp, a quartz halogen lamp, a standard halogen lamp. As will be appreciated by those skilled in the art, a variety of suitable lighting sources can be employed in the embodiments disclosed herein, without departing from the scope of the invention.

Light source: The Op-ONSor 1500 devices of the embodiments of the invention may include one or more light sources; such as light sources that is solid state or LEDs. Alternatively, the light sources may emit non-coherent light. In still other embodiments, the light sources may be blue light sources that emit non-coherent light in a range from 400 nm to 500 mm and in the range of 680-830 nm for NIR light. In other embodiments, the blue light source may be limited in wavelength to 460 nm to 500 nm. In still other embodiments, the light source may be adapted to emit substantially only blue light with a wave length 480 nm.

In still other embodiments, the light source may be adapted to emit substantially only NIR light with a wave length 820 nm. In some of the embodiments, the light source is located in the housing 1602. In other variation, light source resides outside the housing in the stimulating tube 1604, some of which may reside in the tip 1614 of the stimulating tube 1604. The light sources may each emit light at a different energy or optical power level, or at the same level. The light delivery device 1600 may be configured to provide light from three light sources, each having a different relative output energy, and/or relative energy density level (e.g., fluence) and different wavelengths.

The Op-ONSor devices of the embodiments of the invention can be adapted and/or configured such that the stimulating tube is further adapted to transfer heat proximally when the light source is at the distal end of the stimulating tube. In other embodiments, the stimulating tube can be adapted to focus light from the light source.

As will be appreciated by those skilled in the art, it may be desirable to control variables or control parameters associated with the output of the light delivery device 1600. Examples of such variables include power, timing, frequency, duty cycle, spectral output, and/or illumination pattern. In one embodiment, the control circuit 1626 controls the delivery of power from the power supply 1610 to the light source 1618 according to the activation or status of the controller 1626. For example, in one embodiment, the control circuit 1626 includes a relay, or a transistor, and/or the controller 1626 includes a button, or a switch. When the button or switch of the controller 1626 is pressed or activated, power from the power supply 1610 is able to flow through the control circuit 1576 and/or the light source 1618.

Intranasal transdermal optical stimulation of V1 for both nasal cavities may be simultaneous or alternating. In alternating mode of V1 stimulation, the optical stimulus activate one side for a time (3 seconds) while there is no stimulation of the other side during this period, followed by 3 second stimulation of the non stimulated side with no stimulation of the opposite side, and/or this cycle of alternating stimulation can be continued during the session of optical ONS.

Hybrid Electro-Optical Stimulation

In some embodiments, the present invention provides an apparatus and a method for optical, electrical or by hybrid electro-optical stimulation of neurons of V1 in the nasal cavity to obtain a physiological response in a subject (e.g., increased OBF) and to treat retinal choroidal and optic nerve diseases caused by reduced dysregulated OBF In some embodiments, one or more electrodes are placed adjacent the AEN, a branch of V1 intranasally to provide a sensitizing stimulation signal that by itself, would not be sufficient to trigger a nerve action potential (NAP), but when combined with an optical stimulation signal applied in temporal proximity, enhances the probability of triggering a desired NAP along the V1

In some embodiments, simultaneous application of both an optical stimulation signal and an electrical stimulation signal provides more efficacious generation of NAP responses in the subject than either optical or electrical stimulation alone. In addition, the much higher precision possible when using optical stimulation permits many more channels of ophthalmic nerve pathway such as unmyelinated C nerve fibers and and/or Aδ fiber neurons to be individually and distinctly stimulated than is possible using electrical stimulation alone. In some embodiments, the application of an electrical field before or during the application of the optical stimulation pulse permits more reliable generation of NAP signals than is possible using the optical signal pulse alone, and permits reliable generation of NAP signals. In some embodiments, optical stimulation pulses are also provided at short repeated intervals (called "spikes) shortly after the threshold-level electrical stimulation signal, delivered to certain frequency-specific ophthalmic-nerve pathways in order to enhance the expression of SP and CGRP in neurovascular tissues of the retina, choroid and optic nerve.

As used herein, "light emitter' is the light-emitting end from which a light signal is delivered to assist in, or by itself cause, stimulation of a nerve action potential (NAP). In some embodiments, light emitter is the light-emitting end of an optical fiber or similar waveguide that couples light from a light source such as a laser, or light-emitting diode (LED) or the like, connected to an electrical controller to a location at a distance from the controller (i.e., the light is coupled from where it is generated in or near the controller to the nerve to be stimulated, which is at a distance from the controller), while in other embodiments, the light source is located proximate to the nerve to be stimulated, and is electrically coupled to the distal controller FIG. 17 illustrates a diagram of a noninvasive system of HEOp-ONSor 1700 that uses both electrical stimulation and light stimulation of V1 to obtain ocular vascular response for a subject. In some embodiments, the device 1700 includes an optical portion and an electrical portion for the stimulation In one embodiment, the device comprised stimulating part 1702, housing 1704, and nasal clip 1706. In one embodiment, the optical portion of the device is represented by a stimulating tube 1710 comprised of proximal opaque part and/or distal transparent part. The proximal end of the stimulating tube 1710 is coupled to the distal end of the housing 1704 by any of a variety of couplings 1716. In one embodiment, the housing 1704 of the body includes a light source 1712. In one embodiment, the electrical portion 1708 is represented by a sleeve covering the simulating tube wherein a plurality of electrodes is embedded in the wall sleeve 1718.

The stimulating sleeve 1708 may comprise a plurality of electrodes 1720, 1722 located on the wall 1718 of the stimulating sleeve 1708. Two or more electrodes may be spaced longitudinally along the length of the nasal aspect (in contact of the nasal septum) of the sleeve. The electrodes described herein may comprise any conductive materials, such as hydrogel or metals, conductive ceramics, or the like.

As shown in FIG. 17 B the cut-sectional view of the stimulating sleeve 1708, of HEOp-ONSor 1700, the electrodes 1720 and/or 1722 may be connected to leads 1724 and/or 1726 located within stimulating sleeve 1708. The leads 1724 and 1726 may in turn be connected to connectors 1728 and/or 1730 respectively. Connectors 1728 and 1730 may extend through the proximal part of the housing 1704, and/or may connect directly or indirectly to the control subsystem (not shown) and/or power source 1734. In one variations of HEOp-ONSor 1700, may comprise a return contact 1732 located on the angle and/or inner surface of arm of the nasal clip 1706, and/or configured to be in contact with shin of nostril. As such, the electrical stimulus may travel from the control subsystem (not shown) through the connectors 1728 and 1730, through the leads 1724 and/or 1726, and/or through the electrodes 1720 and/or 1722 stimulating the nasal mucosa of the septum of the subject, activating TVS and/or TABRs for increasing the OBF in eyes with dysregulated reduced OBF.

The proximal end of the stimulating sleeve 1708 is coupled to the distal end of the housing 1704 by any of a variety of couplings 1716 such as a press-fit connection, a screw, or any other suitable coupling that ensure optimal mechanical, optical, and/or electrical couplings. In some variations, the stimulating sleeve 1708 may be permanently attached to the housing 1704. In one embodiment, the sleeve 1708 is disposable and/or in another embodiment, the sleeve is not disposable. Non-disposable sleeve is sterilizable.

In some embodiments, the electro-optical application head of the present invention is used to stimulate selective melanopsin containing nerve fibers by using subthreshold stimulus of blue light energy (480 nm) to sensitize theses fibers combined with subthreshold electrical stimulus. Hybrid electro-optical stimulation of melanopsin containing nerve fibers is configured to produce nerve action potential in melanopsin containing nerve fibers of V1, thereof, enhance expression of SP and CGRP in neurovascular tissues of the eye.

FIG. 18A shows for illustrative purposes only show an example of HEOp-ONSor 1800 perspective longitudinal cut sectional view of one embodiment of the present invention. The said device uses both electrical stimulation and light stimulation of AEN to provide an effective method for increasing OBF in subjects with dysregulated blood flow ocular vascular response for patient. In some embodiments, the HEO-ONSor 1800 includes plurality of optical fibers for optical stimulation and a number of electrodes for electrical stimulation of V1.

As shown in FIG. 18A, device comprised of an application head 1802 which can be held in place by a nasal clip 1804 during the treatment session without undue effort. The optic fibers for example optic fiber 1806, 1808 are incorporated in the application head and run for variable lengths where it ends in a light emitter 1810, 1812. In some embodiments, one or more of the light-delivery options is used in HEO-ONSor 1800. In a first option, a waveguide 1806 ends in an angled facet 1810 and reflects or diffracts the light out in a radial or side 'side firing' direction 1810 of the waveguide 1806 as light/laser beam 1814 toward the nasal septum or lateral nasal wall. In a second option, a waveguide 1808 ends in an bullet like end facet 1820 that transmits the light out in an axial direction 1816 of the waveguide as laser beam 1816, Such that the length of the end of fiber 1808 is perpendicular or at some other steep angle to the nerve fibers of V1 to be stimulated at the nasal cavity. Proximate the proximal end of the housing, the preferred embodiment has a plurality of optic fibers gathered in a single port 1818 and connected to the light source by any connecting cable (not shown) via a suitable coupling 1820.

The intranasal application head 1802 of HEOp ONSor 1800 comprised also of a plurality of electrodes incorporated in the application head 1802 of the device. A plurality of electrodes for example 1822 and 1824 are present on either surface of the application head. The inner surface of the nasal clip 1804 provides a place for return electrode 1826 that come in contact with skin of the lateral wall of the nose. During administration of electric ONS, typically electrodes for both sides of application head are held in contact with mucosal lining of the nasal septum and lateral wall of nasal cavity by the means of clipping 1804 method, while the return contact 1426 touching the skin of nostril.

FIG. 18B shows for illustrative purposes only shows an example of front view of one of the application surfaces of HEO-ONSor 1800 as an embodiment of the present invention. The application head surface 1850 comprised a plurality of optic fibers that end in a light side emitter arranged in horizontal rows of windows; 1852, 1854, 1856, 1858 that deliver pulsed blue and/or NIR light toward the nasal septum and lateral nasal wall, and axial emitters 1860 that dispose light stimulus toward the nasal cavity. In this way, the light signal having a specific wavelength is emitted through window in the horizontal rows 1852. 1854, 1856, and 1858, focused on corresponding areas of the nasal septum or temporal wall of the nasal cavity, while axial emitter 1860 deposits its light signal towards the mucosa of nasal cavity. A number of electrodes 1862, 1864, 1866, 1868 are distributed in a regular manner between the rows of windows for light emitters.

In some embodiments, the light signal used to stimulate a NAP includes wavelengths in the range of 450-480 nm which responsible for activation/sensitization of melanopsin containing nerve fibers and in some particular embodiments wavelengths in the range of 650-850 nm where the red/NIR is suitable wavelength stimulation of unmyelinated nerve fibers at deeper levels. In some embodiment, all light signals having the same wavelength is emitted through all windows and focused on corresponding areas of excitable tissue of the AEN underneath the mucosa. In other embodiment the light emitters dispose subthreshold signal having a wave length of 480 nm and 840. The blue light signal is configured to stimulate the superficially located, electrically sensitized nerve fibers while the NIR light will stimulate nerve fibers at deeper levels preferably unmyelinated C fibers. In some embodiments, a plurality of electrical signals is also generated and applied to the nasal mucosa near the site of optically stimulated tissues, and applied to pre-sensitize the excitable tissue such that a lower-powered optical signal beam can be used to trigger a NAP. In some embodiments, the optical windows in the rows 1852, 1854, and 1856, include micro lenses between the light emitter and the target tissue in collimated, diverging, or converging patterns. In some embodiments, the micro lenses direct light in circular path, or disperse light from 0 to 360 degrees in a radial pattern perpendicular to fiber with set area and divergence angle.

The lower-power optical output of hybrid electro-optical stimulation provides at least some of the following advantages: it reduces the power needed from the battery, it reduces the amount of heat generated by the optical source, and it reduces the possibility of tissue damage from the optical signal. In some embodiments, the present invention is used in applications where there is a need for precise placement of an electrode, but with the requirement to stimulate a large number of nerves, either simultaneously or individually. A single-core optical element allows for extremely precise stimulation but can lack the ability to supply and/or spread enough power to stimulate large areas of nerves. In some embodiments, the electrical portion of the probe lacks specificity (since even with a point source of electricity, the electrical signal will spread across electrically conductive tissue), but can provide sufficient power to stimulate large areas. In some embodiments, the electro-optical application head of the present invention is used in selective stimulation of unmyelinated C nerve fibers where locating the application head at nasal cavity wherein these targeted nerve fibers are pre conditioned by subthreshold electrical stimulation and selectively stimulated by deposition of subthreshold stimulus of blue light.

In some embodiments, the HEOp-ONSOR 1800 all of the light signals haves substantially the same wavelength, since each signal is carried by a separate waveguide from the sources to their respective ends where they emit the respective light beams, each directed at a different target of excitable tissue of AEN. In other embodiments the HEOp-ONSOR 1800 uses a plurality of sources (not shown) that each emit a different wavelength of light and that generate coordinated electrical stimulation signals to sensitize the excitable tissue of AEN. In some embodiments, the wavelength is matched to the desired penetration depth wherein a portion of the emitters distributed in the rows 1852, 1854, 1856, 1858 emit blue light (480 nm) to sensitize/activate superficially located melanopsin containing C unmyelinated nerve and to a lesser extent to sensitize and/activate melanopsin containing C unmyelinated nerve at deeper level. In other embodiments, other portion of emitters within said windows emit NIR light 820 nm) to further sensitize the deeply located melanopsin containing C unmyelinated nerve and to an extent make them selectively activated by sub-threshold electrical stimulus form adjacent electrodes of the application head In some embodiments, the electro-optical application head housing heat sink is made of a heat-conducting biocompatible material that has a relatively large thermal mass that readily absorbs short heat spikes from the light emitters and then dissipates the heat over a longer period of time to the proximal aspect of the stimulator 1802. In some embodiments, the intranasal application head housing heatsink includes an inside layer 1830 of very-high thermal-conductivity material such as copper that readily absorbs short heat spikes from the pulsed signals, and an outer layer 1870 of thinner biocompatible material such as titanium, which has a lower thermal conductivity to dissipate the heat over a longer period of time in order to prevent thermal damage to nasal tissue.

Transdermal Electrical ONSor Devices

It relates to a transdermal electrical nerve stimulation (TENS) apparatus for stimulation to V1. Generally, the devices are handheld or portable devices. The portable version of E-ONSor may have portable case, and/or intranasal heads, extra nasal application heads, upper lid and/or forehead adhesive electrodes.

Described here are methods for treating eye disorders by providing electrical stimulation to an anatomical structure located intranasally (mucosa of the nasal septum) or extra nasally over the nasal bridge, foreheads and/or eyelids. Exemplary anatomical structures include different receptors and/or nerve fibers of V1.

Portable Transdermal Electric ONSor 1900 (E-ONSor 1900)

More specifically, the invention, in some embodiments thereof, relates to an E-TD-ONSor 1900 device that operates in the electrical current range of about 0.7 mA to 3.5 mA for intranasal stimulation and 1-10 mA for extranasal sits of stimulation, using a frequency ranged from 20-60 Hz. The device is configured to deliver a pulse-based electrical waveform, which might be biphasic, alternating monophasic, or monophasic or the like. In some embodiment the device has a portable case (housing) and/or different types of stimulating electrodes. The stimulation waveforms described herein may be delivered via intranasal applicator clips 1804, extra nasal application clips 1850 to the nasal bridge (e.g., nose supported), the foreheads and/or upper eyelids (self supported adhesive electrodes).

Figure 19A:
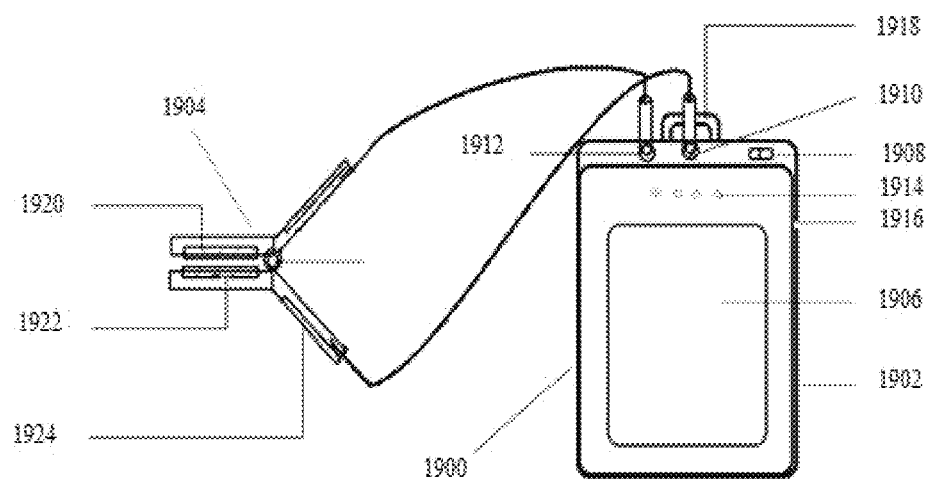
FIG. 19A-B shows schematic illustrations of exemplary configurations of a portable electrical ONSor (E-ONSor 1900)
Figure 19B:
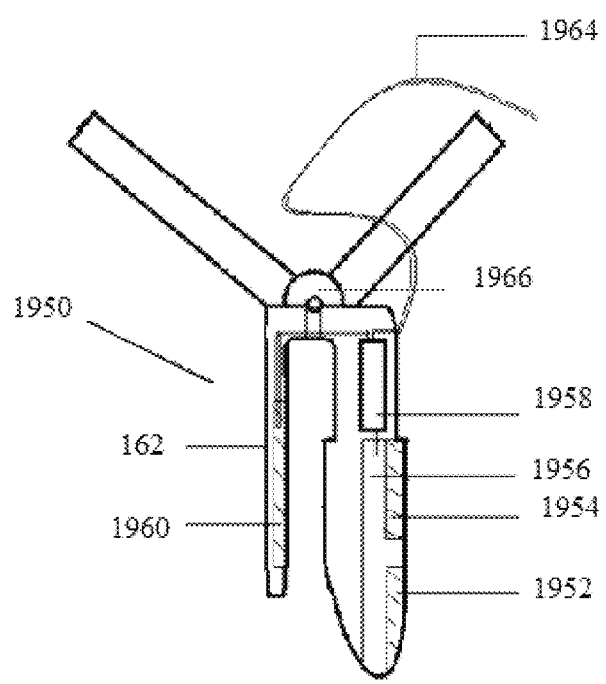

FIG. 19 A illustrates one particularly preferred embodiment of the present invention wherein the E-TD-ONSor 1900 consists of a portable housing 1902 with two external electrodes 1904. In this particular embodiment the case or housing 1902 is equipped with a clip 1918 that allows the unit to be worn on the belt or the like during use. The other side of the case 1902 relative to the clip 1918 is equipped with a user interface 1906 that allows the user to adjust different parameters of the electrical stimulus such as the frequency, amplitude, shape of waveform and/or etc., and/or modulating these parameters or select preset features of the stimulus.

The top face of the case 1902 is further provided with an on/off switch 1908 and/or a monitor light 1914. Also, there are two electrode connector terminals 1910 and/or 1912 provided on the top face of the case 1902. They are connected to electrodes incorporated in the intranasal septal clip applicator 1904. The two inner surfaces of the distal end of the clip 1904 accommodate electrodes 1920, 1922. One or more electrodes are present on the inner surface of the clip. The outer surface of the proximal end of the clip 1904 provides a place for return electrode 1924 that come in contact with the inner lateral wall of the vestibule. During administration of electric ONS, typically electrodes 1920, 1922 for both sides of nostril are held in contact with mucosal lining of the nasal septum by the means of clipping method, while the return contact 1924 touching the skin of nostril.

Intranasal stimulation: In nose supported variations, intra nasal application head 1950 (FIG. 19 B) with nasally supported clips and having two sets of electrodes 1952, 1954 may be used to stimulate one side of the nasal septum, while the return electrode 1960 is configured to touch the skin of exterior of the nose. The electrodes are connected by leads and/or wired to the body of the device 1900. The latter contain user interface 1906, controller, and/or feedback elements for various purposes. The user interface may comprise one or more operating mechanisms to adjust one or more parameters of the stimulus. Additionally or alternatively, the user interface may comprise one or more feedback elements.

When bilateral electrical ONS is required, Intranasal application head 1904 (FIG. 19 A) with two sets of electrodes 1920, 1922 may be used to stimulate either side of the nasal septum of the nose, while the return electrode 1924 is configured to touch the skin of outlet of the nose. The electrodes are connected by leads and/or wired to the body of the device 1900.

Electrical stimulation of V1 in both sides of the nose may be simultaneous or alternating. Whenever simultaneous stimulation of V1 in both sides is considered, and/or the waveform comprises a biphasic pulse, it may be desirable to configure the biphasic pulse to be charge-balanced, so that the net charge delivered by the biphasic pulse is approximately zero. Each phase of biphasic pulse may be either voltage controlled or current controlled.

In this particular illustrated embodiment, a limited number of frequency settings are available to the user (typically 20 Hz, 30 Hz or 40 Hz). As such this particular embodiment is easily operated by the patient. In a more complex embodiment, a greater number of preselected discrete frequency settings are provided with different modulated waveforms.

Hand Held TD-E-ONSor 2000

Figure 20:
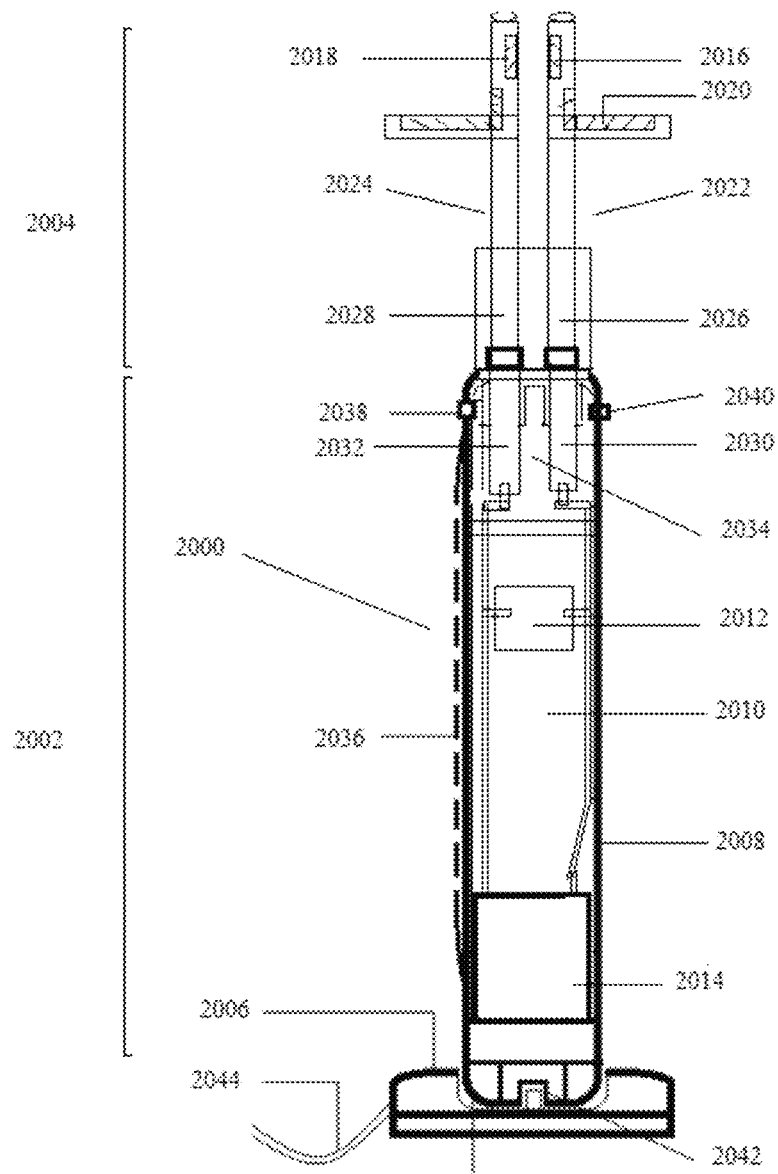
FIG. 20 shows schematic illustrations of exemplary configurations of a portable hand held electrical ONSor (E-ONSor 2000)
Figure 21:
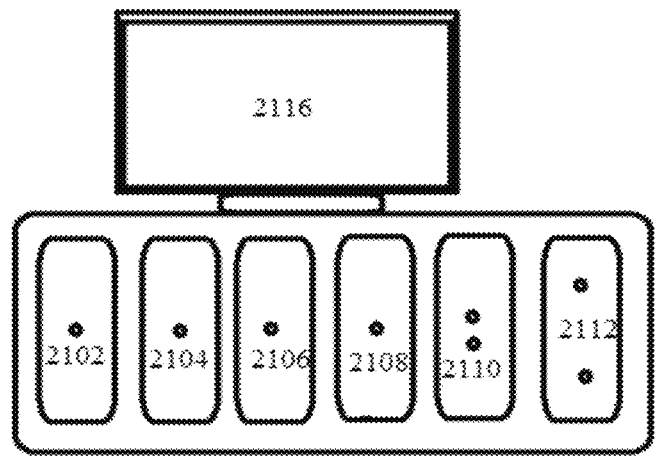
FIG. 21 depicts an exemplary multi-modular system for ONS

Hand Held TD-E-ONSor 2000 is illustrated in FIG. 20. The handheld variations comprising a stimulator body 2002 and/or the stimulator probe 2004. The body of E-ONSor 2000 is generally cylindrical or tetragonal in shape with blunt angles grasped by a hand of a user and/or a disposable, detachable stimulator probe 2004 formed at its top end with one or two L shaped application heads 2022, 2024. The stimulator body 2002 may comprise a housing 2008 with front housing, back housing, side housings and/or proximal housing, which may fit together to define a body cavity 2010. The anterior housing of the body is equipped with a user interface 2036 that allows the user to adjust different parameters of the electrical stimulus such as the frequency, amplitude, shape of waveform, etc., and/or modulating these parameters or select preset features of the stimulus. The top of anterior housing is further provided with monitor lights 2038, while top of posterior housing provided with an on/off switch 2040. The stimulating probe 2004, which may be push-fitted onto the body of the stimulator 2002 in a manner inhibiting relative movement, while at the same time a secure electrical connection between the stimulator probe 2004 and/or the body of 2002 the stimulator is ensured. The stimulator body may comprise a power source 2014 and/or control subsystem 2012 and, which together may generate and/or control the stimulus.

The stimulator probe 2004 may comprise one or two L-shaped intra-nasal application heads 2022, 2024. Each intranasal application head 2022, 2024 may comprise an electrode 2016, 2018 located on the inner surface of the distal end of the application head 2022, 2024. Two or more electrodes may be spaced longitudinally along the length of the inner aspect of the long arm of L-shaped intranasal application head. The electrodes described herein may comprise any conductive materials, such as hydrogel or metals, conductive ceramics, or the like. As shown in the cut-away view of the E-ONSor 2000 in FIG. 20, the electrodes 2016 and/or 2018 may be connected to leads 2026 and/or 2028 located within application head 2022 and/or 2024, respectively. The leads 2026 and/or 2028 may in turn be connected to connectors 2030 and/or 2032, respectively. Connectors 2030 and/or 2032 may extend through lumens in the proximal housing, and/or may connect directly or indirectly to the control subsystem 2012 and/or power source 2014. As such, the electrical stimulus may travel from the control subsystem 2012 through the connectors 2030 and/or 2032, through the leads 2026 and/or 2028, and/or through the electrodes 2016 and/or 2018 stimulating the nasal mucosa of the septum of the subject, activating TVS and/or TABRs for increasing the OBF in eyes with dysregulated reduced OBF.

In some variations of handheld stimulators, may comprise a return contact 2020 located on the angle and/or upper surface of short arm of L shaped application head, and/or configured to be in contact with shin of nostril. The return contact might be placed on the stimulator body, and/or may be configured to be in contact with the hand of the user.

It may be desirable that the electrode 2016, 2018 have smooth rounded edges, to help minimize the risk of tissue damage during advancement of the electrode into the nose. The shape of the electrode may have spherical, ovoid or rectangular design. The electrode may have any suitable length, such as between about 3 mm and/or about 10 mm. The shape and/or size of the electrode is configured to deliver current to the nasal mucosa of the septum of the vestibule in order to stimulate septal branch of AEN, and/or to activate TVS and/or TABRS and/or pancreatic or anti-inflammatory TVR. In some instances, the impedance provided by tissue may be at least partially dependent on the presence or absence of wetting substance such as gel or natural mucous secretion of the nose.

Figure 4:
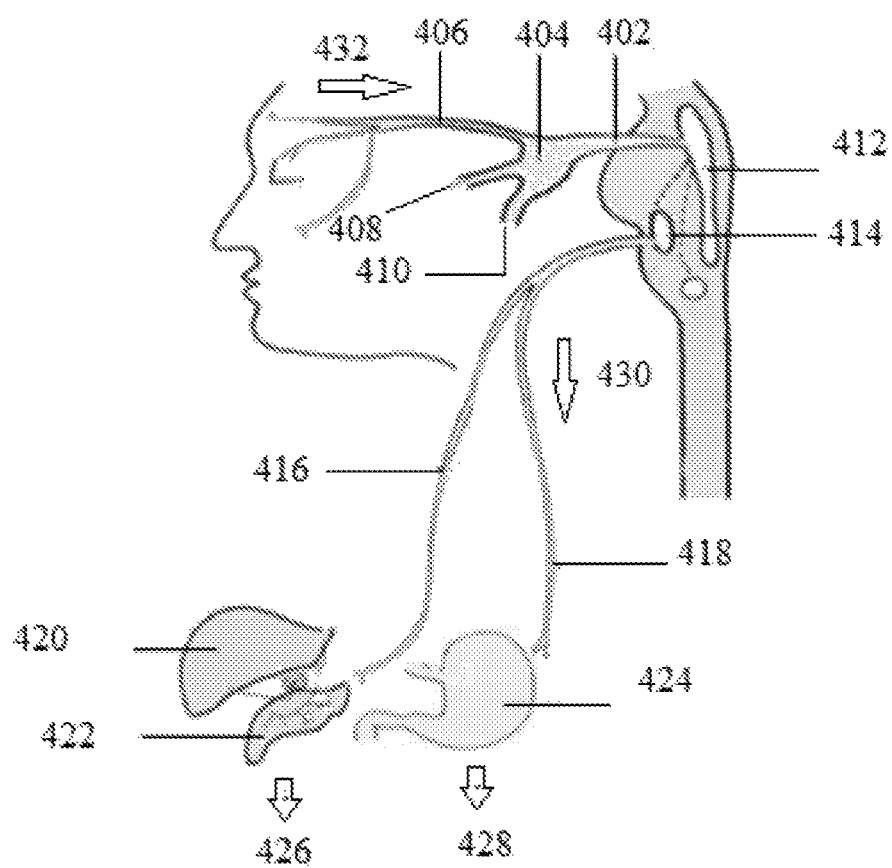
FIG. 4 illustrates a proposed pathway of trigemino-autonomic brain reflex. The vagus nerve presented as the efferent limb of the reflex and pancreas is the organ to be activated.

FIGS. 3-4 show a general scheme of the flow of electrical stimulation to targeted vascular tissues of the ocular circulation or indirectly through the brain. Stimulating the septal branch of AEN, electrical stimulation is provided in the nasal mucosa of the septum (more preferable site of stimulation) and/or from there is transmitted to the AEN, to the nasociliary nerve to trigeminal ganglion, and/or antidromically to short and/or long ciliary nerves causing vasodilatation and/or decreased vascular resistance. In other pathway, the electrical stimulus is transmitted to brain stem, activating the superior salivatory nucleus (SSN), and/or parasympathetic system through SPG and/or causing vasodilation of ophthalmic artery, short and/or long ciliary arteries, and/or choroidal arterioles leading to increased OBF.

The plurality of waveform parameters that define the stimulation waveforms may be selected from the group consisting of on/off duration, frequency, pulse width, amplitude, and/or shape. Other suitable waveform parameters may also be used.

The frequency in some of these variations ranges from about 20 to 60 Hz. In some of these variations, the frequency ranges from about 20 to 50 Hz. In some of these variations, the frequency ranges from about 30 to 40 Hz. In some variations, the frequency is 30 Hz. In some variations, the frequency is 10, 20, 40 Hz. In some variations, the frequency might be fixed or modulated over time.

In some of these variations, the on/off duration ranges from about 0.1 to 5.0 seconds on, and/or about 0.1 to 5.0 seconds off. In some of these variations, the on/off duration is 1.0 second on, and/or 1.0 second off. In some of these variations, the on/off duration is 5.0 seconds on, and/or 5.0 seconds off.

The amplitude ranges from about 0.1 to 10 mA. In some of these variations, the maximum amplitude ranges from about 1 to 3 mA.

A particular combination of the parameters of the waveform, its modulation over time, and/or spatial or temporal patterning may be applied using a stimulator comprising a plurality of combinations stored in memory. Selection of the stored combinations may be random, predetermined, or controlled by a user.

In some variations the methods described herein comprise applying patterned electrical stimulation to an anatomical structure intra-nasally or extra-nasally to stimulate V1, and/or activate the TVS, and/or TABRs, thereby increasing OBF, wherein the patterned electrical stimulation comprises a biphasic waveform having cathodic and/or anodic pulse pairs. In some of these variations, the ratio of duration to amplitude for the cathodic pulse varies over time according to a saw tooth function. In some of these variations, the ratio of duration to amplitude for the cathodic pulse varies over time according to a sinusoidal function.

The frequency, peak-to-peak amplitude, and/or pulse width of the waveforms may be constant, but in some variations the stimulator may be configured to vary the frequency, amplitude, and/or pulse width of the waveform. This variation may occur according to a predetermined plan, or may be configured to occur randomly within given parameters.

In some variations, the electrical stimulus can be one of a plurality of preset waveforms comprising at least a first preset waveform and/or a second preset waveform, and/or changing the electrical stimulus from the first preset waveform to the second preset waveform while delivering the electrical stimulus. The electrical stimulus may be changed from the first preset waveform to the second preset waveform by the patient. In some of these variations, the applied patterned stimulation is randomly selected from the plurality of stored patterned stimulation waveforms. In some of these variations, the plurality of stored patterned stimulation waveforms is patient-optimized waveforms. In some variations, the applied patterned stimulation is stored in memory as a patient-optimized waveform.

In some variations, the methods described herein comprise providing a device to a patient having ocular disorders such as RP, wherein the device is configured to deliver a plurality of electrical waveforms to an anatomical target in a patient, and/or instructing the patient to select one or more of the plurality of waveforms. In some of these variations, the anatomical target may be the nasal mucosa. In some of these variations, the anatomical target may be the nasal bridge. In others of these variations, the anatomical target may be the forehead or upper eyelids. In some of these variations, at least one of the pluralities of waveforms may have a pulse width that varies over time. In some of these variations, the pulse width may vary over time according to an exponential function.

In some variations, the nose supported stimulators are configured for placement on the skin of the nasal bridge. The stimulators, which may for example, comprise two, four, or more active electrodes. In some variations, the systems are configured for activating cutaneous sensors or nerve fibers innervating cutaneous sensors in one side of the nose followed by stimulation of the skin of the other side of the nose on alternate fashion to reduce accommodation.

In some variations, the programmable memory is capable of storing up to 10 patterned stimulation waveforms. In some variations the system further comprises a user interface for selecting one or more of the stored plurality of patterned waveforms. In some variations, the controller is configured to execute a program those cycles through a plurality of waveform parameter options.

In some variations, the devices described herein comprise a handheld stimulator comprising a stimulator body comprising a user interface, and/or a stimulator probe comprising an application head comprising an electrode. The stimulator may be configured to deliver a plurality of electrical waveforms, and/or the user interface may be configured for selection of one of the plurality of electrical waveforms. Each of the waveforms may have at least one of a pulse shape, maximum amplitude, pulse width, or frequency that is modulated over time. In some of these variations, each of the waveforms may have at least two of a pulse shape, maximum amplitude, pulse width, or frequency that is modulated over time. In some variations, each of the waveforms has a pulse shape that is modulated over time. In some variations, the waveform comprises a first period comprising a two-phase current-controlled waveform, and/or a second period comprising a current-controlled phase followed by a voltage-controlled phase.

SP, Platelet Rich Plasma (N/PRP)

Described here are methods for treating ocular disorders by providing sufficient ONS followed by preparation of N/PRP with high SP/CGRP content from EJV blood samples. The N/PRP, when delivered to the subtenon's space in patients with ocular disorders, for example IRDS such as RP, as described herein, is capable of initiating a diverse set of pathways, including those involved in vasodilatation, augmentation of OBF, RPE proliferation, prevention of apoptosis, suppressing neuroinflammation, promoting the migration and differentiation of vascular endothelial cells as well as mobilization of EMSCs from the bone marrow to the circulation to accelerate tissue repair of the diseased retina as in RP.

In some embodiments, the patients received ONS for 6 days in order to enhance SP/CGR expression, followed by collection of blood from EJV. Blood sample of 15 cc is collected in acid/citrate/dextrose and centrifuged with 2500 rpm for 15 minutes at room temperature within 10 minutes after blood collection. Three layers including red blood cells at the bottom, a PRP in the middle layer and platelet poor plasma in the top layer formed in the tube. Middle layer (which mainly contained platelets) was drawn by syringe and ready for immediate use.

In some embodiments, N/PRP is injected immediately in the subtenon's space of the patient. In other embodiments, the N/PRP is used for preparation of sustained release formulation of SP/CGRP. For example, N/PRP-soaked biodegradable collagen matrix (Ologen) such as incorporation with biodegradable collagen is implanted in a deep scleral tunnel in the infero-temporal quadrant of the sclera 9 mm from the limbus as source of SP/CGRP and other growth factors that are naturally present in PRP as a treatment for ocular disorders such as AMD or RP.

Sympatholytic Effect of Intravenous Ascorbic Acid (Vitamin C)

Interestingly, oxidative stress appears to be involved in the enhanced central sympathetic outflow. There are a number of studies supporting the hypothesis that increased oxidative stress may contribute to the pathogenesis of sympathetic overactivity in a number of diseases including essential hypertension. Intravenous administration of vitamin C produces substantially higher plasma concentrations than those achievable with oral administration and/or proved to achieve sympatholytic effects. Therefore, it is reasonable to postulate that intravenous administration of high dose of vitamin C is able to induce centrally mediated sympatholytic effect.

Various embodiments and/or aspects of the present invention as delineated hereinabove and/or as claimed in the claims section below find experimental support in the following examples.

Setting and Examples

Reference is now made to the following settings and examples, which together with the above descriptions illustrate some embodiments of the invention in a non-limiting fashion.

Settings:
Setting 1

Protocol of Intravenous Vitamin C Therapy for Sympatholysis:

For adults, Intravenous administration of AA in a dose of 3 gm dissolved in 100 ml of saline is infused at 5 ml min$^{-1}$ for 20 min in the first day, followed by a drip infusion of 1 g dissolved in 100 ml daily during the rest of the treatment period. For adolescents, AA is administered intravenously in a dose of 0.045 gm per kg body weight. In the first day, 0.015 g per kg body weight thereafter. This dose of AA is given one-hour prior neuromodulation session Setting 2

Vibrotactile ONS is delivered intranasally via intranasal application head of V-ONSor 600, nasal clip of portable V-ONS 800, and/or nasal application heads of V-ONSor 900. Extra nasal stimulation of the nasal bridge and/or forehead is delivered by portable V-ONSor 600. Vibrotactile stimulation frequency is in the range of 20 Hz-90 Hz. with on/off periods of 4 second on and/or 1 seconds off; a minimum stimulation amplitude of 1.5 µm, a maximum stimulation amplitude of 3.5 µm, a variation in stimulation amplitude of 2.0 µm, and/or an amplitude modulation frequency of 2.0 Hz, a minimum pulse width of 0 µm; a maximum pulse width of 300 µm; a pulse width modulation frequency of 1 Hz. The duration of extra-nasal stimulation is 12-20 minutes for nasal bridge and forehead stimulation in both sides. Duration of intranasal stimulation varies between 3-6 minutes for each nostril and/or the duration of whole session of vibrotactile stimulation varies between 20-30 minutes or more.

Settings 3

Vibro-chemical ONS is delivered intranasally via intranasal application head of V-Ch-ONSor 1300. The V-Ch ONSor is a bi-modular device, with one system producing vibrotactile stimulation and/or a second system stimulate V1 chemically by TRPM8 agonist using a specific micro pump for delivering the chemical agent in a pulsatile way with a frequency ranging from 0.5 Hz to 2 Hz, and/or 2 second on/13 second off. Programming of vibrotactile and/or chemical stimulation might be in the form of initial 2 second of chemical stimulation followed by 11 second of vibration stimulation, followed by 2 second off for both chemical stimulation and/or vibrational stimulation. This pattern may be repeated during the session of treatment. The setting of Vibrotactile stimulation might be chosen from any of the above-mentioned parameters for vibrotactile setting.

Setting 4

Ultrasonic ONS is delivered intranasally via intranasal application head of US-ONS 1400. After application of coupling gel on the ultrasound probe, and/or insertion of the probe intranasally opposite the nasal septal mucosa of the vestibule, the US-ONSor 1400 is activated using the following set up; the Ultrasonic stimulation frequency is between 500 Hz to 8 Mhz, with on/off periods of 3 second on and/or 1 seconds off; a minimum ultrasound power 30 mW/cm$^2$, a maximum ultrasound power 60 mW/cm$^2$, a variation in maximum ultrasound power of 30 mW/cm$^2$, and/or an ultrasound power modulation frequency of 2.0 Hz, with average burst time of 200 μs. Duration of intranasal stimulation varies between 3-6 minutes for each nostril and/or the duration of whole session of ultrasonic stimulation varies between 6-12 minutes.

Setting 5

Optical ONS is delivered intranasally via intranasal stimulation tube of O-ONSor 1500. Blue light (wavelength; 480 nm) stimulation is delivered intranasally via O-ONSor 1500. The stimulation frequency is between 10 Hz to 50 Hz, duty cycle 50%, with on/off periods of 10 second on and/or 1 second off; the minimum energy output 10 mW/cm$^2$, and/or maximum energy output 40 mW/cm$^2$. Frequency modulation is 2.0 Hz with average duration of treatment session of 5-10 minutes.

Setting 6

Electrical ONS is delivered intranasally via intranasal application head of portable E-ONSor 1900, or by the use of intranasal head of the hand-held version E-ONS 2000. Extra nasal electrical stimulation of the nasal bridge and/or forehead is delivered by portable E-ONSor 1900. The electrical stimulation features include a frequency of 10 Hz-60 Hz with on/off periods of 4 second on and/or 1 seconds off; a minimum stimulation amplitude of 7.0 mA, a maximum stimulation amplitude of 3.50 mA for intranasal stimulation and rang between 1-10 mA for extra-nasal stimulation, and/or an amplitude modulation frequency of 2.0 Hz, a minimum pulse width of 0 μm; a maximum pulse width of 300 μm; a pulse width modulation frequency of 1.0 Hz. The duration of extra-nasal stimulation (nasal bridge, forehead areas in both sides) varies from 8-12 minutes. Duration of intranasal stimulation varies between 4-8 minutes and/or the duration of whole session of vibration stimulation varies between 14-20 minutes.

EXAMPLES

Example 1

Intranasal Vibrotactile Stimulation: A patterned waveform of ONS is delivered intranasally, to the subjects using intranasal application head of V-ONSor 600, nasally clipped application head of portable V-ONS 800, or nasal application heads of V-ONSor 900. The head of intranasal probe is introduced intranasally to come in contact of the mucosa of the nasal septum. The delivered waveform is square shaped, with frequency of 60-90 Hz, and/or amplitude of 1.5 μm-3.0 μm, with on/off periods of 4 seconds on and/or 1 second off. The session duration is 3-5 minutes on each nostril.

Example 2

Extranasal Vibrotactile Stimulation: A patterned waveform of ONS is delivered extra-nasally, to the subjects over the nasal bridge and/or supraorbital region using a flat topped heads of V-ONSor 600, or extra-nasal application heads of V-ONSor 900. The delivered waveform is square shaped, with frequency of 60-90 Hz, and/or amplitude of 1.5 μm-5.0 μm, with on/off periods of 4 seconds on and/or 2 seconds off. The session duration is 6 minutes.

Example 3

Intranasal Vibro-chemical Stimulation: A patterned waveform of ONS is delivered intranasally, to the subjects using intranasal application head of V-Ch-ONSor 1300. The head of intranasal probe is introduced intranasally to come in contact of the mucosa of the nasal septum. The chemical stimulation might be adjusted regarding timing of stimulation, on/off and/or frequency of injection. For example, the micro pump is delivering the chemical agent for example 2% menthol in a pulsatile way with a frequency ranging from 0.5 Hz to 2 Hz, and/or 2 second on/13 second off. Programming of vibrotactile and/or chemical stimulation might be in the form of initial 2 second of chemical stimulation followed by 11 second of vibrotactile stimulation, followed by 2 second off for both chemical stimulation and/or vibrotactile stimulation. This pattern can be repeated over the session of treatment.

Example 4

Intranasal optical blue light Stimulation: A patterned waveform of ONS is delivered intranasally to the subjects using a device Op-ONSor 1500 as described with respect to FIGS. 15A-B. Semiconductor light emitting diode (LED) is the Light source with Wavelength: 480 nm (blue light), and/or energy output: 10 mW/cm$^2$ to 40 mW/cm$^2$ using a pulse mode of 40 Hz at 50% duty cycle. The stimulating tube is introduced intranasally and/or self supported by a mean of clipping to the lateral nasal wall. A 5-10 minutes session per nostril is delivered once or twice daily for 2 consecutive weeks as a primary treatment or twice weekly as additional treatment with other types of ONS such as vibrotactile ONS Example 5

Intranasal hybrid electro-optical ONS: A patterned waveform of electrical ONS is delivered intranasally to the subjects using a device HEOp-ONSor 1700 as described with respect to FIGS. 17A-B. Preconditioning of the AEN is configured to be performed using subthreshold electrical stimulus of less than 1.0 mA to less than 3.0 mA. Semiconductor light emitting diode (LED) is the Light source with Wavelength: 480 nm (blue light), and/or subthreshold energy output: less than 10 mW/cm$^2$ to less than 40 mW/cm$^2$. Both electrical and optical stimulation are delivered simultaneously in a pulse mode of 40 Hz at 50% duty cycle. The stimulating tube is introduced intranasally and/or self supported by a mean of clipping to the lateral nasal wall. A 5-10 minutes session per nostril is delivered once or twice daily for 2 consecutive weeks as a primary treatment or twice weekly as additional treatment with other types of ONS such as vibrotactile ONS.

Example 6

Preparation of Neuropeptide/Platelet Rich Plasma: A patterned waveform of vibrotactile ONS is delivered intranasally and at extranasal sites daily for 6 days. (One session per day; 20-30 minutes per session). On day 6 and after finishing the last session of ONS, the patient lay in the supine position with the neck slightly extended. The skin of the neck is cleaned by alcohol. Blood sample of 15 cc is collected in acid/citrate/dextrose and centrifuged with 2500 rpm for 15 minutes at room temperature within 10 minutes after blood collection. Three layers including red blood cells at the bottom, a PRP in the middle layer and platelet poor plasma in the top layer formed in the tube. Middle layer (which mainly contained platelets) was drawn by syringe and ready for immediate use. For subtenon's injection of N/PRP, topical anesthesia is installed in the conjunctival sac of the said patient. The lids are opened using a wire speculum. A 27 gauge needle is used to inject 2-3 cc of autologous N/PRP in the sub-tendon space Example 7

Neuromodulation for Treatment of Retinitis Pigmentosa:

Forty-four participants (82 eyes) with rod-cone dystrophy were recruited into an open-label interventional trial. This was a prospective case series in which all subjects received a vibrochemical neuromodulation to determine efficacy and/or safety of this new therapeutic modality.

Following recruitment, all subjects with clinically established diagnosis of RP, the included participants completed baseline vision, ocular assessments, self reported low luminance questionnaire (LLQ), OCTA and VF testing within 2-4 weeks prior to initiating the neuromodulation therapy. Clinical examination includes BCVA, slit lamp examination, and IOP measurement with Goldmann applanation tonometry. Both eyes were dilated with 2.5% phenylephrine and 1% tropicamide. Fundus examination was performed using stereobiomicroscopy, the degree of attenuation of retinal arterioles and their extension, distribution of pigmentary changes as well as the degree of optic nerve disc pallor were evaluated and clinically graded. The severity of the disease is clinically graded into 1-5 stages. During the treatment period, the blood pressure, pulse rate and random blood sugar were measured before initiating the neuromodulation therapy and at the end of each session.

Treatment Protocol: A pre-determined regimen of systemic ascorbic acid was given one hour prior to ONS. The intranasal vibrochemical ONS and extranasal vibrotactile ONS were delivered over a period of two weeks, followed by continuous uptake of AA acid and trans-nasal stimulation of V1 using menthol 2%. All types of smoking were prohibited and passive exposure to smoke was discouraged during the treatment period and thereafter.

A prototype of vibrotactile stimulator with different types of application heads is developed and employed by using modified commercially available micro-vibrators. A patterned of modulated waveform of vibrotactile ONS is delivered to the subjects. The delivered waveform is square shaped, with modulated frequency (60 Hz-90 Hz) and stimulation amplitude (1.5 μm-3.5 μm). During intranasal vibrotactile stimulation, the nasal head of the probe is covered by rubber cape impregnated by 2% of aqueous paste of menthol as a TRPM8.

TABLE 1

| Number of patients | 44 patients |
|---|---|
| Sex distribution | 24 males/20 Females |
| Mean age ± SD in years | 27.3 ± 12.8 years |
| Number of eyes included | 82 eyes |
| Stage of the disease per eye | |
| Stage 2 | 12 eyes (14.6%) |
| Stage 3 | 32 eye (39%) |
| Stage 4 | 26 eyes (31.7%) |
| Stage 5 | 12 eyes (14.6%) |
| Inheritance | |
| Autosomal recessive | 24 patients (55.8) |
| Autosomal dominant | 5 patients (11.6%) |
| X-linked | 1 patient (2.3 %) |
| Simplex cases | 13 patients (30.2%) |
| Type of RP | |
| Classical type | 37 patients (84.1%) |
| Usher disease | 7 patients (15.9%) |

Results: The study included 82 eyes of 44 participants (82 eyes) with mean age of patients at baseline was 27.3±12.8 years. Details of demographic data are illustrated in Table 1. All patients received 2 weeks regimen of vibrochemical ONS. Of these patients, 3 patients received additional Vibro-chemical ONS for one week after 6-9 months, 3 of them received re-treatment after 9-12 months. During the first year, 6 patients (5%) of the patients needed re-treatment among them 5 patients having stage IV or V RP. No clinically significant side effects were encountered during the treatment as regards to pulse, blood pressure, and ECG monitoring or during the follow up period (9-18 months) apart from mild headache developed in 5 patients during the treatment rounds that resolved without treatment. This headache is likely related to increased cerebral blood flow.

Figure 22:
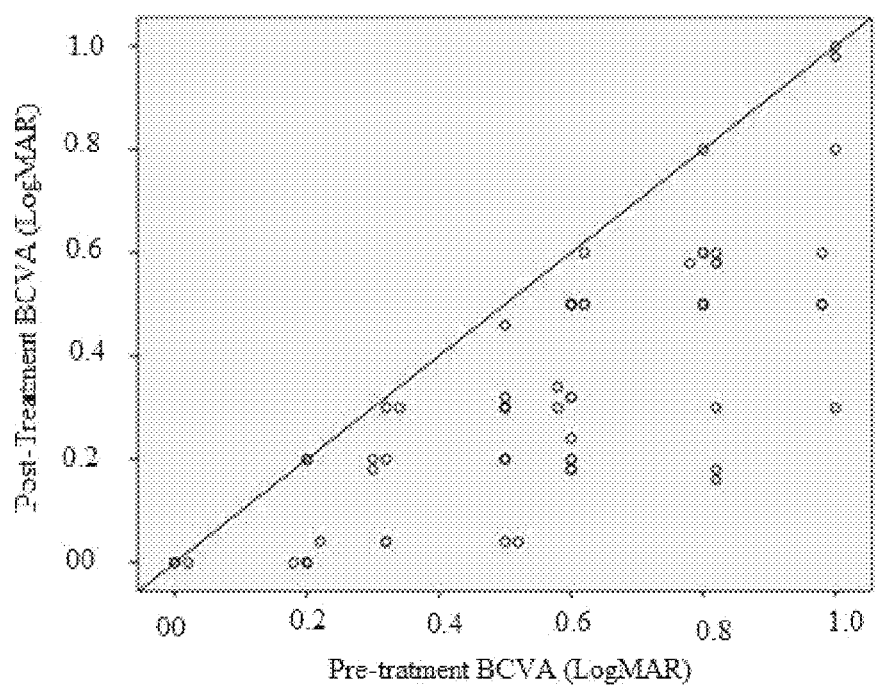
FIG. 22 illustrates the effect of ONS on BCVA
Figure 23:
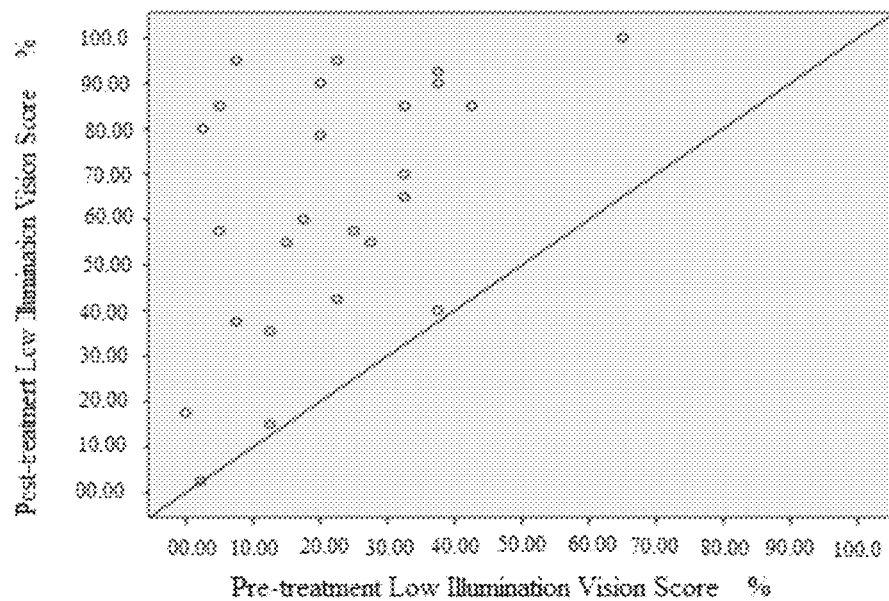
FIG. 23 illustrates the effect of ONS on Night Vision Score
Figure 24:
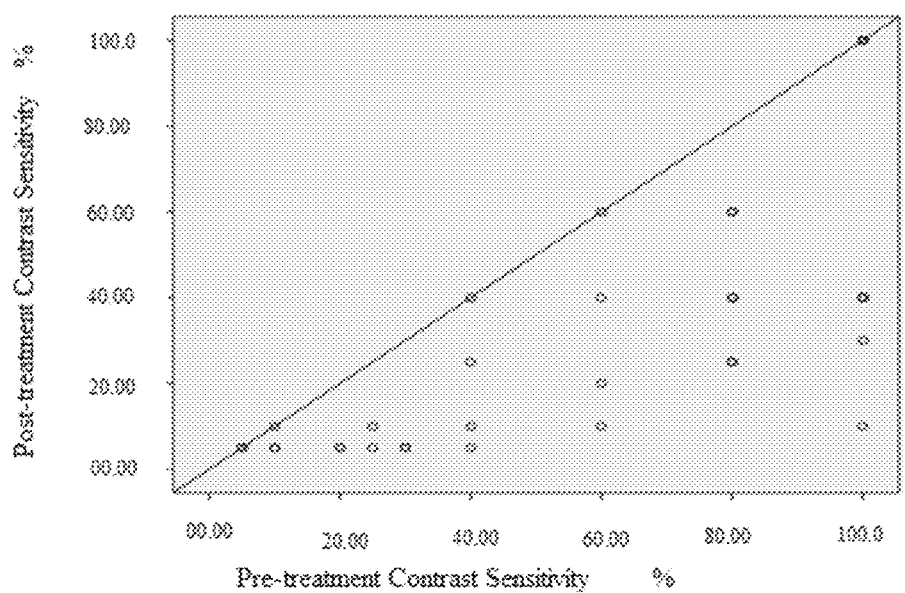
FIG. 24 illustrates the effect of ONS on Contrast sensitivity
Figure 25:
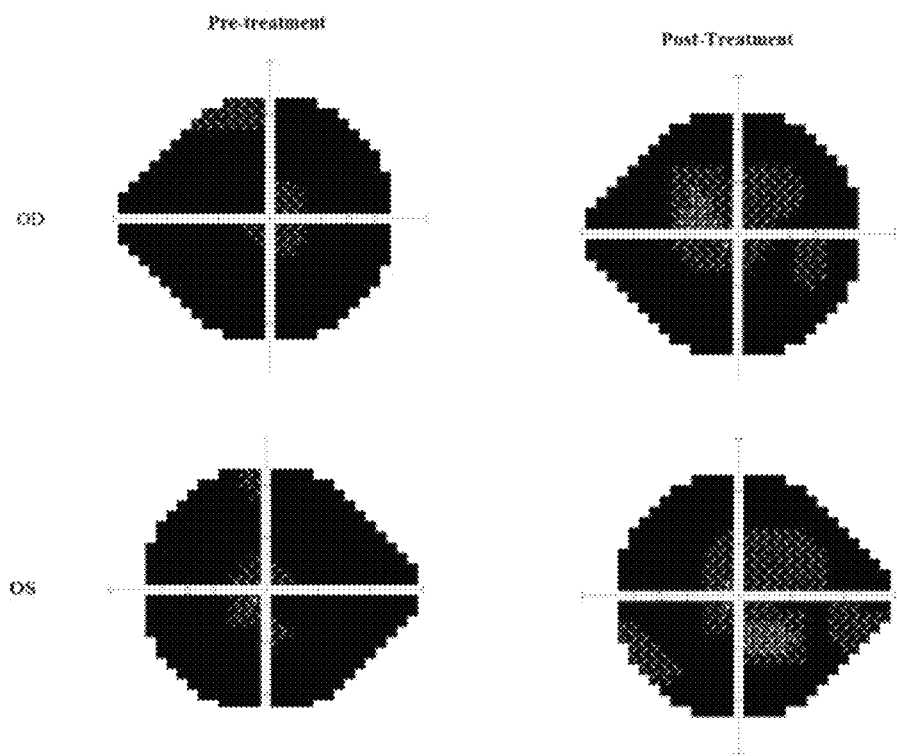
FIG. 25 illustrates the effect of ONS on Visual fields

Table 2, FIG. 22 and FIG. 23 showed the effect of treatment on BCVA and NVS. The mean BCVA of the 82 eyes studied before treatment was 0.62±0.34. It improved to 0.38±0.28 (P value 0.001). The mean night vision score was also improved from 21.67%±15.6% to 63.5%±27.7% (P value 0.001). Changes in CS is also assessed by CVA comparison of pre-treatment and post-treatment values. This was done for 30 eyes that had valid CVA test results available at baseline, 2 weeks and 1, 3, 6, 12 months visits. The measures of CSV are significantly improved after receiving the Vibro-chemical ONS treatment as shown in FIG. 24. FIG. 25 showed visual field changes in OD and/or OS after receiving a protocol of ONS for treatment of RP. Significant enlargement of visual filed is noticed in this figure. For patients receiving ONS therapy, the enlargement of visual field is variable depending on a number of factors including the stage of the disease.

TABLE 2

| | Mean before treatment | Mean after treatment | Mean difference | P-value |
|---|---|---|---|---|
| BCVA in logMAR (82 eye) | 0.62 ± 0.34 | 0.38 ± 0.28 | 0.24 ± 0.19 | 0.001 |
| Night Vision Score (25 patients) | 21.67% ± 15.6% | 63.5% ± 27.7% | 41.8% ± 24.3% | 0.0001 |

While the preceding description contains much specificity, these should not be construed as limitations on the scope of the invention, but rather as an exemplification of a preferred embodiment and/or additional embodiments. Many other variations are possible.

Skilled artisans will readily be able to change dimensions, shapes and/or construction materials of the various components described in the embodiment. Accordingly, the scope of the invention should be determined not by the embodiment illustrated, but by the appended claims and/or their legal equivalents.

The various embodiments described above are provided by way of illustration only and/or should not be construed to limit the invention. Based on the above discussion and/or illustrations, those skilled in the art will readily recognize that various modifications and/or changes may be made to the present invention without strictly following the exemplary embodiments and/or applications illustrated and/or described herein. Such modifications and/or changes do not depart from the true spirit and/or scope of the present invention It is expected that during the life of a patent maturing from this application many relevant technologies will be developed and/or the scope of the terms are intended to include all such new technologies a priori. As used herein the term "about" refers to ±10%

The terms "comprises", "comprising", "includes", "including", "having" and/or their conjugates mean "including but not limited to".

The term "consisting of" means "including and/or limited to".

The term "consisting essentially of" means that the composition, method or structure may include additional ingredients, steps and/or parts, but only if the additional ingredients, steps and/or parts do not materially alter the basic and/or novel characteristics of the claimed composition, method or structure.

As used herein, the singular form "a", "an" and/or "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and/or brevity and/or should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and/or 6. This applies regardless of the breadth of the range.

Whenever a numerical range is indicated herein, it is meant to include any cited numeral (fractional or integral) within the indicated range. The phrases "ranging/ranges between" a first indicate number and/or a second indicate number and/or "ranging/ranges from" a first indicate number "to" a second indicate number are used herein interchangeably and/or are meant to include the first and/or second indicated numbers and/or all the fractional and/or integral numerals therebetween.

As used herein the term "method" refers to manners, means, techniques and/or procedures for accomplishing a given task including, but not limited to, those manners, means, techniques and/or procedures either known to, or readily developed from known manners, means, techniques and/or procedures by practitioners of the chemical, pharmacological, biological, biochemical and/or medical arts.

As used herein, the term "treating" includes abrogating, substantially inhibiting, slowing or reversing the progression of a condition, substantially ameliorating clinical or aesthetical symptoms of a condition or substantially inhibiting the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and/or variations will be apparent to those skilled in the art. Accordingly, it is intended to embrace all such alternatives, modifications and/or variations that fall within the spirit and/or broad scope of the appended claims.

All publications, patents and/or patent applications mentioned in this specification are herein incorporated in their entirety by reference into the specification, to the same extent as if each individual publication, patent or patent application was specifically and/or individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of preventing, suppressing or treating ocular disorders in a subject, wherein the method comprises:
    applying to the subject, Ophthalmic Nerve Stimulation (ONS) via at least one of mechanical, chemical, optical and electrical, and hybrid electro-optical means-stimuli to at least one of branch of an ophthalmic nerve;
    administering to the subject, at least one of pharmacological doses of a freshly prepared Neuropeptides/platelet Rich Plasma (N/PRP), a combination of freshly prepared N/PRP with ascorbic acid as an antioxidant and a combination of freshly prepared N/PRP with a sympatholytic agent,
    wherein the freshly prepared N/PRP is generated from centrifugation of a blood sample taken from an external jugular vein of the subject immediately after receiving a sufficient amount of ascorbic acid,
    wherein said applying and said administering are of an effective amount to for the preventing, suppressing or treating ocular disorders of the subject.

2. The method of claim 1, wherein the ocular disorders include at least one member selected from the set consisting of retinal, choroidal and optic nerve disorders comprising retinitis pigmentosa, Cone Rod Dystrophy (CRD), congenital achromatopsia, acute and chronic central serous chorioretinopathy (CSCR), diabetic retinopathy, diabetic maculopathy, ophthalmic artery occlusion, central and branch retinal artery occlusion (CRAO), central and branch retinal vein occlusion (CRVO), deep retinal capillary ischemia, macular drusen, dry and wet types of age related macular degeneration (AMD), ischemic optic neuropathies, glaucomatous optic neuropathies, traumatic optic neuropathies inflammatory optic neuropathies nutritional optic neuropathies, idiopathic optic neuropathies and hereditary optic neuropathies.

3. The method of claim 1, wherein the ONS is applied to branches of ophthalmic nerve intranasally and at extranasal sites including a nasal bridge, supraorbital region and upper eyelids, wherein stimulated branch of ophthalmic nerve is selected from one or more members of the group consisting of an anterior ethmoid nerve (AEN), a supraorbital nerve, supra-trochlear nerve, infra-trochlear nerve, and branches of nasociliary and frontal nerve.

4. The method of claim 1 wherein chronic ONS activates trigemino-vascular system (TVS) thereby inducing a sustained decreased vascular resistance, enhanced vasodilatation and improved blood flow in an ophthalmic artery (OA), central retinal artery (CRA), posterior ciliary arteries (PCAs), anterior ciliary arteries (ACAs), and choroidal arteries by a release of Substance P (SP), or Calcitonin gene-related peptide (CGRP).

5. The method of claim 1 wherein chronic ONS activates trigemino-autonomic brain reflexes (TABRs) and/or sphenopalatine ganglion, thereof induces sustained activation of parasympathetic nervous system (PNS) including trigemino-vagal reflexes and decreases vascular resistance, enhances vasodilatation and improves blood flow in an ophthalmic artery (OA), central retinal artery (CRA), posterior ciliary arteries (PCAs), anterior ciliary arteries (ACAs) and choroidal arteries.

6. The method of claim 1, wherein the ONS is mechanical stimulation by a portable vibrotactile ophthalmic nerve stimulator device with intranasal and/or extranasal application heads configured to deliver a modulated, low magnitude, high frequency vibrotactile stimulus to activate ophthalmic branches of trigeminal nerve (VI) intranasally and/or at extranasal sites, wherein the stimulus has a frequency of 40 Hz-90 Hz, and, amplitude of 2-5 μm, on daily basis for two weeks or more.

7. The method of claim 1, wherein said N/PRP include substance P rich plasma.

8. A method of treating or preventing ocular disorders in a subject, comprising:
repeated systemic administration of pharmacological doses of ascorbic acid to the subject in conjunction with or prior to ophthalmic nerve stimulation (ONS);
sub-tenon injecting of an effective amount of a freshly prepared Neuropeptides/Platelet Rich Plasma (N/PRP), wherein the freshly prepared N/PRP is generated from centrifugation of a blood sample taken from an external jugular vein of the subject immediately after receiving a sufficient amount of ascorbic acid or substance P degradation inhibitors;
applying at least one application head of ophthalmic a nerve stimulator device on or proximate to a branch of an ophthalmic nerve said applying to at least one of an intranasal site and an extranasal site of the subject; and
activating the at least one application head to apply at least one of mechanical, chemical, optical, electrical, and hybrid electro-optical stimulus to said branch of the ophthalmic nerve.

9. The method of claim 8, wherein the ocular disorders are selected from the group consisting of retinitis pigmentosa, Leber's congenital amaurosis, X-linked choroideraemia, Cone Rod Dystrophy, cone dystrophy, Stargardt disease, congenital achromatopsia, acute and chronic central serous chorioretinopathy, diabetic retinopathy, diabetic maculopathy, acute ophthalmic artery occlusion, acute central and branch retinal artery occlusion, central and branch retinal vein occlusion, deep retinal capillary ischemia, dry and wet types of age related macular degeneration, acute ischemic optic neuropathies and glaucomatous optic neuropathies.

10. The method of claim 8, wherein the ophthalmic nerve stimulation is intranasally delivered to a nasal mucosa, and extra nasally to skin of a nasal bridge, and a forehead for stimulation of the branch of the ophthalmic nerve, including at least one member from the group consisting of anterior ethmoid nerve, supraorbital nerve, supra-trochlear nerve, and infra-trochlear nerve.

11. The method of claim 8, wherein the ONS is configured for selective activation of substance P containing small unmyelinated C fibers and medium-sized Aδ fibers of ophthalmic nerve thereby induces sustained release of substance P in the external jugular vein and neurovascular tissue of an eye.

12. The method of claim 8, further comprising:
repeatedly administrating pharmacological doses of ascorbic acid as an anti-oxidant, sympatholytic and substance P degradation inhibitor in conjunction with or prior to ONS, wherein ascorbic acid is given intravenously in a loading dose of 50-100 mg/kg to the subject in a first day followed by 25-50 mg/kg body weight as a daily maintenance dose thereof over a period of time.

13. The method of claim 8, wherein acute ocular disorders are selected from the group consisting of acute ophthalmic artery occlusion, acute central and branch retinal artery occlusion, acute central and branch retinal vein occlusion and acute ischemic optic neuropathy.

14. The method of claim 8, further comprising delivering ONS sessions for approximately 30 to approximately 60 minutes, one to 4 times daily over a period of 4-14 days.

15. The method of claim 8, further comprising:
repeated local or systemic administration of ascorbic acid as an anti-oxidant, sympatholytic and substance P degradation inhibitor, to the subject in conjunction with or prior to ONS, or combinations thereof; over a period of time;
wherein the subject has subacute or chronic ocular disorders of retina, choroid and optic nerve.

16. The method of claim 8, wherein treating or preventing ocular disorders in a human subject, comprises:
systemic administration of ascorbic acid as anti-oxidants, sympatholytic and substance P degradation inhibitor to the subject in conjunction with or prior to mechanical ONS, wherein mechanical stimulus is delivered in bursts and has modulated frequency of 40 Hz-90 Hz, pulse width of 0-300 μs and, amplitude of 2-20 μm.

17. The method of claim 16, wherein intranasal vibrotactile mechanical stimulation is delivered by a vibrotactile ophthalmic nerve stimulator device comprising a nasal application head, wherein the nasal application head is placed in contact with nasal mucosa of the subject.

18. The method of claim 16, wherein extra-nasal vibrotactile mechanical stimulation is delivered by a vibrotactile ophthalmic nerve stimulator device comprising an extranasal application head, wherein the extranasal application head is placed in contact with skin of a forehead and a nasal bridge of the subject.

19. The method of claim 16, wherein vibrotactile ONS is applied by a portable, handheld, head mounted or nasally supported device.

20. The method of claim 16, wherein vibrotactile ONS is applied by an ophthalmic nerve stimulator device including a user interface configured to adjust at least one parameter of the intranasal and extranasal mechanical stimulation.

21. The method of claim 8, wherein treating or preventing ocular disorders in a human subject, comprising:

repeated systemic administration of ascorbic acid as an anti-oxidant, sympatholytic and substance P degradation inhibitor to the subject in conjunction with or prior to vibro-chemical ONS, wherein pulsatile injection of an effective amount of one or more of cold receptors (TRPM8) agonist is delivered, to a nasal mucosa using an automated micro-pump incorporated in an intranasal application head of vibro-chemical ophthalmic nerve stimulator device in a rate of ½ to 2 Hz.

22. The method of claim 21, further comprising loading a reservoir of a vibro-chemical ophthalmic nerve stimulator device with a composition comprising a pharmaceutically acceptable carrier in a paste form, an ointment, a gel, a liquid, a mist, an emulsion, or a suspension of a TRPM8 agonist.

23. The method of claim 21 wherein TRPM8 agonist include Menthol, Icilin, and Eucalyptol.

24. A system for treating a patient with an ocular disorder, the system comprising:

an effective amount of freshly prepared Neuropeptides/Platelet Rich Plasma (N/PRP) ready for sub-tenon injection, said N/PRP generated from centrifugation of blood sample taken from external jugular vein of a subject immediately after receiving sufficient amount of ascorbic acid as an anti-oxidant or substance P degradation inhibitors combined with ophthalmic nerve stimulation (ONS);

one or more intranasal or extranasal application heads configured to apply the ONS via applying at least one of mechanical, chemical, optical, electrical, or hybrid electro-optical signal, to a branch of an ophthalmic nerve;

a system control unit coupled to said one or more intranasal and/or extranasal application heads to apply the ONS by said mechanical, chemical, optical, electrical, or hybrid electro-optical signal, to said branch of the ophthalmic nerve in accordance with one or more stimulation parameters, wherein the ONS is configured to treat the ocular disorder via overexpression of neurotransmitters form nerve endings and increased ocular blood flow.

* * * * *